(12) United States Patent
Toro et al.

(10) Patent No.: US 9,677,067 B2
(45) Date of Patent: Jun. 13, 2017

(54) COMPOSITIONS AND METHODS FOR SYNTHETIC GENE ASSEMBLY

(71) Applicant: TWIST BIOSCIENCE CORPORATION, San Francisco, CA (US)

(72) Inventors: Esteban Toro, Fremont, CA (US); Sebastian Treusch, San Francisco, CA (US); Siyuan Chen, San Mateo, CA (US); Cheng-Hsien Wu, Burlingame, CA (US)

(73) Assignee: TWIST BIOSCIENCE CORPORATION, San Francisco, CA (US)

( * ) Notice: Subject to any disclaimer, the term of this patent is extended or adjusted under 35 U.S.C. 154(b) by 0 days.

(21) Appl. No.: 15/154,879

(22) Filed: May 13, 2016

(65) Prior Publication Data

US 2016/0264958 A1 Sep. 15, 2016

Related U.S. Application Data

(63) Continuation of application No. PCT/US2016/016636, filed on Feb. 4, 2016.

(60) Provisional application No. 62/112,022, filed on Feb. 4, 2015.

(51) Int. Cl.
*C12N 15/10* (2006.01)
*C12N 15/66* (2006.01)
*C12P 19/34* (2006.01)

(52) U.S. Cl.
CPC ..... *C12N 15/1031* (2013.01); *C12N 15/1027* (2013.01); *C12N 15/66* (2013.01); *C12P 19/34* (2013.01)

(58) Field of Classification Search
None
See application file for complete search history.

(56) References Cited

U.S. PATENT DOCUMENTS

| | | | |
|---|---|---|---|
| 3,549,368 | A | 12/1970 | Robert et al. |
| 3,920,714 | A | 11/1975 | Streck |
| 4,123,661 | A | 10/1978 | Wolf et al. |
| 4,415,732 | A | 11/1983 | Caruthers et al. |
| 4,613,398 | A | 9/1986 | Chiong et al. |
| 4,726,877 | A | 2/1988 | Fryd et al. |

(Continued)

FOREIGN PATENT DOCUMENTS

| | | |
|---|---|---|
| EP | 0090789 A1 | 10/1983 |
| EP | 0126621 B1 | 8/1990 |

(Continued)

OTHER PUBLICATIONS

Abudayyeh et al., C2c2 is a single-component programmable RNA-guided RNA-targeting CRISPR effector. Science, available on line, Jun. 13, 2016, at: http://zlab.mit.edu/assets/reprints/Abudayyeh_OO_Science_2016.pdf, 17 pages.

(Continued)

*Primary Examiner* — Kaijiang Zhang
(74) *Attorney, Agent, or Firm* — Wilson Sonsini Goodrich & Rosati

(57) ABSTRACT

Methods and compositions are provided for assembly of large nucleic acids where the assembled large nucleic acids lack internal sequence modifications made during the assembly process.

25 Claims, 12 Drawing Sheets

(56) References Cited

U.S. PATENT DOCUMENTS

| | | |
|---|---|---|
| 4,808,511 A | 2/1989 | Holmes |
| 4,837,401 A | 6/1989 | Hirose et al. |
| 4,863,557 A | 9/1989 | Kokaku et al. |
| 4,981,797 A | 1/1991 | Jessee et al. |
| 4,988,617 A | 1/1991 | Landegren et al. |
| 5,102,797 A | 4/1992 | Tucker et al. |
| 5,137,814 A | 8/1992 | Rashtchian et al. |
| 5,143,854 A | 9/1992 | Pirrung et al. |
| 5,242,794 A | 9/1993 | Whiteley et al. |
| 5,242,974 A | 9/1993 | Holmes |
| 5,288,514 A | 2/1994 | Ellman |
| 5,299,491 A | 4/1994 | Kawada |
| 5,384,261 A | 1/1995 | Winkler et al. |
| 5,387,541 A | 2/1995 | Hodge et al. |
| 5,395,753 A | 3/1995 | Prakash |
| 5,431,720 A | 7/1995 | Nagai et al. |
| 5,445,934 A | 8/1995 | Fodor et al. |
| 5,449,754 A | 9/1995 | Nishioka |
| 5,459,039 A | 10/1995 | Modrich et al. |
| 5,474,796 A | 12/1995 | Brennan |
| 5,476,930 A | 12/1995 | Letsinger et al. |
| 5,487,993 A | 1/1996 | Herrnstadt et al. |
| 5,494,810 A | 2/1996 | Barany et al. |
| 5,501,893 A | 3/1996 | Laermer et al. |
| 5,508,169 A | 4/1996 | Deugau et al. |
| 5,510,270 A | 4/1996 | Fodor et al. |
| 5,514,789 A | 5/1996 | Kempe |
| 5,527,681 A | 6/1996 | Holmes |
| 5,530,516 A | 6/1996 | Sheets |
| 5,556,750 A | 9/1996 | Modrich et al. |
| 5,586,211 A | 12/1996 | Dumitrou et al. |
| 5,641,658 A | 6/1997 | Adams et al. |
| 5,677,195 A | 10/1997 | Winkler et al. |
| 5,679,522 A | 10/1997 | Modrich et al. |
| 5,700,637 A | 12/1997 | Southern |
| 5,700,642 A | 12/1997 | Monforte et al. |
| 5,702,894 A | 12/1997 | Modrich et al. |
| 5,707,806 A | 1/1998 | Shuber |
| 5,712,124 A | 1/1998 | Walker |
| 5,739,386 A | 4/1998 | Holmes |
| 5,750,672 A | 5/1998 | Kempe |
| 5,780,613 A | 7/1998 | Letsinger et al. |
| 5,830,655 A | 11/1998 | Monforte et al. |
| 5,834,252 A | 11/1998 | Stemmer et al. |
| 5,843,767 A | 12/1998 | Beattie |
| 5,858,754 A | 1/1999 | Modrich et al. |
| 5,861,482 A | 1/1999 | Modrich et al. |
| 5,869,245 A | 2/1999 | Yeung |
| 5,877,280 A | 3/1999 | Wetmur |
| 5,882,496 A | 3/1999 | Northrup et al. |
| 5,922,539 A | 7/1999 | Modrich et al. |
| 5,922,593 A | 7/1999 | Livingston |
| 5,928,907 A | 7/1999 | Woudenberg et al. |
| 6,008,031 A | 12/1999 | Modrich et al. |
| 6,015,674 A | 1/2000 | Woudenberg et al. |
| 6,027,898 A | 2/2000 | Gjerde et al. |
| 6,028,189 A | 2/2000 | Blanchard |
| 6,028,198 A | 2/2000 | Liu et al. |
| 6,040,138 A | 3/2000 | Lockhart et al. |
| 6,077,674 A | 6/2000 | Schleifer et al. |
| 6,103,474 A | 8/2000 | Dellinger et al. |
| 6,107,038 A | 8/2000 | Choudhary et al. |
| 6,110,682 A | 8/2000 | Dellinger et al. |
| 6,114,115 A | 9/2000 | Wagner, Jr. |
| 6,132,997 A | 10/2000 | Shannon |
| 6,136,568 A | 10/2000 | Hiatt et al. |
| 6,171,797 B1 | 1/2001 | Perbost |
| 6,180,351 B1 | 1/2001 | Cattell |
| 6,201,112 B1 | 3/2001 | Ach |
| 6,218,118 B1 | 4/2001 | Sampson et al. |
| 6,221,653 B1 | 4/2001 | Caren et al. |
| 6,222,030 B1 | 4/2001 | Dellinger et al. |
| 6,232,072 B1 | 5/2001 | Fisher |
| 6,235,483 B1 | 5/2001 | Wolber et al. |
| 6,242,266 B1 | 6/2001 | Schleifer et al. |
| 6,251,588 B1 | 6/2001 | Shannon et al. |
| 6,251,595 B1 | 6/2001 | Gordon et al. |
| 6,251,685 B1 | 6/2001 | Dorsel et al. |
| 6,258,454 B1 | 7/2001 | Lefkowitz et al. |
| 6,262,490 B1 | 7/2001 | Hsu et al. |
| 6,284,465 B1 | 9/2001 | Wolber |
| 6,287,776 B1 | 9/2001 | Hefti |
| 6,297,017 B1 | 10/2001 | Schmidt et al. |
| 6,300,137 B1 | 10/2001 | Earhart et al. |
| 6,306,599 B1 | 10/2001 | Perbost |
| 6,309,822 B1 | 10/2001 | Fodor et al. |
| 6,309,828 B1 | 10/2001 | Schleifer et al. |
| 6,319,674 B1 | 11/2001 | Fulcrand et al. |
| 6,323,043 B1 | 11/2001 | Caren et al. |
| 6,329,210 B1 | 12/2001 | Schleifer |
| 6,346,423 B1 | 2/2002 | Schembri |
| 6,365,355 B1 | 4/2002 | McCutchen-Maloney |
| 6,372,483 B2 | 4/2002 | Schleifer et al. |
| 6,375,903 B1 | 4/2002 | Cerrina et al. |
| 6,376,285 B1 | 4/2002 | Joyner et al. |
| 6,384,210 B1 | 5/2002 | Blanchard |
| 6,387,636 B1 | 5/2002 | Perbost et al. |
| 6,399,394 B1 | 6/2002 | Dahm et al. |
| 6,399,516 B1 | 6/2002 | Ayon |
| 6,403,314 B1 | 6/2002 | Lange et al. |
| 6,406,849 B1 | 6/2002 | Dorsel et al. |
| 6,406,851 B1 | 6/2002 | Bass |
| 6,419,883 B1 | 7/2002 | Blanchard |
| 6,428,957 B1 | 8/2002 | Delenstarr |
| 6,440,669 B1 | 8/2002 | Bass et al. |
| 6,444,268 B2 | 9/2002 | Lefkowitz et al. |
| 6,446,642 B1 | 9/2002 | Caren et al. |
| 6,446,682 B1 | 9/2002 | Viken |
| 6,451,998 B1 | 9/2002 | Perbost |
| 6,458,526 B1 | 10/2002 | Schembri et al. |
| 6,458,583 B1 | 10/2002 | Bruhn et al. |
| 6,461,812 B2 | 10/2002 | Barth et al. |
| 6,461,816 B1 | 10/2002 | Wolber et al. |
| 6,469,156 B1 | 10/2002 | Schafer et al. |
| 6,518,056 B2 | 2/2003 | Schembri et al. |
| 6,521,427 B1 | 2/2003 | Evans |
| 6,521,453 B1 | 2/2003 | Crameri et al. |
| 6,558,908 B2 | 5/2003 | Wolber et al. |
| 6,566,495 B1 | 5/2003 | Fodor et al. |
| 6,582,908 B2 | 6/2003 | Fodor et al. |
| 6,582,938 B1 | 6/2003 | Su et al. |
| 6,586,211 B1 | 7/2003 | Staehler et al. |
| 6,587,579 B1 | 7/2003 | Bass |
| 6,589,739 B2 | 7/2003 | Fisher |
| 6,599,693 B1 | 7/2003 | Webb |
| 6,602,472 B1 | 8/2003 | Zimmermann et al. |
| 6,610,978 B2 | 8/2003 | Yin et al. |
| 6,613,513 B1 | 9/2003 | Parce et al. |
| 6,613,523 B2 | 9/2003 | Fischer |
| 6,613,560 B1 | 9/2003 | Tso et al. |
| 6,613,893 B1 | 9/2003 | Webb |
| 6,621,076 B1 | 9/2003 | van de Goor et al. |
| 6,630,581 B2 | 10/2003 | Dellinger et al. |
| 6,632,641 B1 | 10/2003 | Brennan et al. |
| 6,635,226 B1 | 10/2003 | Tso et al. |
| 6,649,348 B2 | 11/2003 | Bass et al. |
| 6,660,338 B1 | 12/2003 | Hargreaves |
| 6,664,112 B2 | 12/2003 | Mulligan et al. |
| 6,670,127 B2 | 12/2003 | Evans |
| 6,670,461 B1 | 12/2003 | Wengel et al. |
| 6,673,552 B2 | 1/2004 | Frey |
| 6,682,702 B2 | 1/2004 | Barth et al. |
| 6,689,319 B1 | 2/2004 | Fisher et al. |
| 6,702,256 B2 | 3/2004 | Killeen et al. |
| 6,706,875 B1 | 3/2004 | Goldberg et al. |
| 6,709,852 B1 | 3/2004 | Bloom et al. |
| 6,709,854 B2 | 3/2004 | Donahue et al. |
| 6,713,262 B2 | 3/2004 | Gillibolian et al. |
| 6,716,629 B2 | 4/2004 | Hess et al. |
| 6,716,634 B1 | 4/2004 | Myerson |
| 6,723,509 B2 | 4/2004 | Ach |
| 6,743,585 B2 | 6/2004 | Dellinger et al. |
| 6,753,145 B2 | 6/2004 | Holcomb et al. |
| 6,770,748 B2 | 8/2004 | Imanishi et al. |

(56) References Cited

U.S. PATENT DOCUMENTS

| | | |
|---|---|---|
| 6,770,892 B2 | 8/2004 | Corson et al. |
| 6,773,676 B2 | 8/2004 | Schembri |
| 6,773,888 B2 | 8/2004 | Li et al. |
| 6,787,308 B2 | 9/2004 | Balasubramanian et al. |
| 6,789,965 B2 | 9/2004 | Barth et al. |
| 6,790,620 B2 | 9/2004 | Bass et al. |
| 6,794,499 B2 | 9/2004 | Wengel et al. |
| 6,796,634 B2 | 9/2004 | Caren et al. |
| 6,800,439 B1 | 10/2004 | McGall et al. |
| 6,814,846 B1 | 11/2004 | Berndt |
| 6,815,218 B1 | 11/2004 | Jacobson et al. |
| 6,824,866 B1 | 11/2004 | Glazer et al. |
| 6,830,890 B2 | 12/2004 | Lockhart et al. |
| 6,833,246 B2 | 12/2004 | Balasubramanian |
| 6,833,450 B1 | 12/2004 | McGall et al. |
| 6,835,938 B2 | 12/2004 | Ghosh et al. |
| 6,838,888 B2 | 1/2005 | Peck |
| 6,841,131 B2 | 1/2005 | Zimmermann et al. |
| 6,845,968 B2 | 1/2005 | Killeen et al. |
| 6,846,454 B2 | 1/2005 | Peck |
| 6,852,850 B2 | 2/2005 | Myerson et al. |
| 6,858,720 B2 | 2/2005 | Myerson et al. |
| 6,879,915 B2 | 4/2005 | Cattell |
| 6,880,576 B2 | 4/2005 | Karp et al. |
| 6,884,580 B2 | 4/2005 | Caren et al. |
| 6,887,715 B2 | 5/2005 | Schembri |
| 6,890,723 B2 | 5/2005 | Perbost et al. |
| 6,890,760 B1 | 5/2005 | Webb |
| 6,893,816 B1 | 5/2005 | Beattie |
| 6,897,023 B2 | 5/2005 | Fu et al. |
| 6,900,047 B2 | 5/2005 | Bass |
| 6,900,048 B2 | 5/2005 | Perbost |
| 6,911,611 B2 | 6/2005 | Wong et al. |
| 6,914,229 B2 | 7/2005 | Corson et al. |
| 6,916,113 B2 | 7/2005 | Van de Goor et al. |
| 6,916,633 B1 | 7/2005 | Shannon |
| 6,919,181 B2 | 7/2005 | Hargreaves |
| 6,927,029 B2 | 8/2005 | Lefkowitz et al. |
| 6,929,951 B2 | 8/2005 | Corson et al. |
| 6,936,472 B2 | 8/2005 | Earhart et al. |
| 6,938,476 B2 | 9/2005 | Chesk |
| 6,939,673 B2 | 9/2005 | Bass et al. |
| 6,943,036 B2 | 9/2005 | Bass |
| 6,946,285 B2 | 9/2005 | Bass |
| 6,950,756 B2 | 9/2005 | Kincaid |
| 6,958,119 B2 | 10/2005 | Yin et al. |
| 6,960,464 B2 | 11/2005 | Jessee et al. |
| 6,969,488 B2 | 11/2005 | Bridgham et al. |
| 6,976,384 B2 | 12/2005 | Hobbs et al. |
| 6,977,223 B2 | 12/2005 | George et al. |
| 6,987,263 B2 | 1/2006 | Hobbs et al. |
| 6,989,267 B2 | 1/2006 | Kim et al. |
| 7,008,037 B2 | 3/2006 | Caren et al. |
| 7,025,324 B1 | 4/2006 | Slocum et al. |
| 7,026,124 B2 | 4/2006 | Barth et al. |
| 7,027,930 B2 | 4/2006 | Cattell |
| 7,028,536 B2 | 4/2006 | Karp et al. |
| 7,029,854 B2 | 4/2006 | Collins et al. |
| 7,034,290 B2 | 4/2006 | Lu et al. |
| 7,051,574 B2 | 5/2006 | Peck |
| 7,052,841 B2 | 5/2006 | Delenstarr |
| 7,062,385 B2 | 6/2006 | White et al. |
| 7,070,932 B2 | 7/2006 | Leproust et al. |
| 7,075,161 B2 | 7/2006 | Barth |
| 7,078,167 B2 | 7/2006 | Delenstarr et al. |
| 7,078,505 B2 | 7/2006 | Bass et al. |
| 7,094,537 B2 | 8/2006 | Leproust et al. |
| 7,097,974 B1 | 8/2006 | Staehler et al. |
| 7,101,508 B2 | 9/2006 | Thompson et al. |
| 7,101,986 B2 | 9/2006 | Dellinger et al. |
| 7,105,295 B2 | 9/2006 | Bass et al. |
| 7,115,423 B1 | 10/2006 | Mitchell |
| 7,122,303 B2 | 10/2006 | Delenstarr et al. |
| 7,125,488 B2 | 10/2006 | Li |
| 7,125,523 B2 | 10/2006 | Sillman |
| 7,128,876 B2 | 10/2006 | Yin et al. |
| 7,129,075 B2 | 10/2006 | Gerard et al. |
| 7,135,565 B2 | 11/2006 | Dellinger et al. |
| 7,138,062 B2 | 11/2006 | Yin et al. |
| 7,141,368 B2 | 11/2006 | Fisher et al. |
| 7,141,807 B2 | 11/2006 | Joyce et al. |
| 7,147,362 B2 | 12/2006 | Caren et al. |
| 7,153,689 B2 | 12/2006 | Tolosko et al. |
| 7,163,660 B2 | 1/2007 | Lehmann |
| 7,166,258 B2 | 1/2007 | Bass et al. |
| 7,179,659 B2 | 2/2007 | Stolowitz et al. |
| 7,192,710 B2 | 3/2007 | Gellibolian et al. |
| 7,193,077 B2 | 3/2007 | Dellinger et al. |
| 7,198,939 B2 | 4/2007 | Dorsel et al. |
| 7,202,264 B2 | 4/2007 | Ravikumar et al. |
| 7,202,358 B2 | 4/2007 | Hargreaves |
| 7,205,128 B2 | 4/2007 | Ilsley et al. |
| 7,205,400 B2 | 4/2007 | Webb |
| 7,206,439 B2 | 4/2007 | Zhou et al. |
| 7,208,322 B2 | 4/2007 | Stolowitz et al. |
| 7,220,573 B2 | 5/2007 | Shea et al. |
| 7,221,785 B2 | 5/2007 | Curry et al. |
| 7,226,862 B2 | 6/2007 | Staehler et al. |
| 7,229,497 B2 | 6/2007 | Stott et al. |
| 7,247,337 B1 | 7/2007 | Leproust et al. |
| 7,247,497 B2 | 7/2007 | Dahm et al. |
| 7,252,938 B2 | 8/2007 | Leproust et al. |
| 7,269,518 B2 | 9/2007 | Corson |
| 7,271,258 B2 | 9/2007 | Dellinger et al. |
| 7,276,336 B1 | 10/2007 | Webb et al. |
| 7,276,378 B2 | 10/2007 | Myerson |
| 7,282,183 B2 | 10/2007 | Peck |
| 7,282,332 B2 | 10/2007 | Caren et al. |
| 7,282,705 B2 | 10/2007 | Brennen |
| 7,291,471 B2 | 11/2007 | Sampson et al. |
| 7,302,348 B2 | 11/2007 | Ghosh et al. |
| 7,314,599 B2 | 1/2008 | Roitman et al. |
| 7,323,320 B2 | 1/2008 | Oleinikov |
| 7,344,831 B2 | 3/2008 | Wolber et al. |
| 7,348,144 B2 | 3/2008 | Minor |
| 7,351,379 B2 | 4/2008 | Schleifer |
| 7,353,116 B2 | 4/2008 | Webb et al. |
| 7,361,906 B2 | 4/2008 | Ghosh et al. |
| 7,364,896 B2 | 4/2008 | Schembri |
| 7,368,550 B2 | 5/2008 | Dellinger et al. |
| 7,371,348 B2 | 5/2008 | Schleifer et al. |
| 7,371,519 B2 | 5/2008 | Wolber et al. |
| 7,371,580 B2 | 5/2008 | Yakhini et al. |
| 7,372,982 B2 | 5/2008 | Le Cocq |
| 7,385,050 B2 | 6/2008 | Dellinger et al. |
| 7,390,457 B2 | 6/2008 | Schembri |
| 7,396,676 B2 | 7/2008 | Robotti et al. |
| 7,399,844 B2 | 7/2008 | Sampson et al. |
| 7,402,279 B2 | 7/2008 | Schembri |
| 7,411,061 B2 | 8/2008 | Myerson et al. |
| 7,413,709 B2 | 8/2008 | Roitman et al. |
| 7,417,139 B2 | 8/2008 | Dellinger et al. |
| 7,422,911 B2 | 9/2008 | Schembri |
| 7,427,679 B2 | 9/2008 | Dellinger et al. |
| 7,435,810 B2 | 10/2008 | Myerson et al. |
| 7,439,272 B2 | 10/2008 | Xu |
| 7,488,607 B2 | 2/2009 | Tom-Moy et al. |
| 7,504,213 B2 | 3/2009 | Sana et al. |
| 7,514,369 B2 | 4/2009 | Li et al. |
| 7,517,979 B2 | 4/2009 | Wolber |
| 7,524,942 B2 | 4/2009 | Wang et al. |
| 7,524,950 B2 | 4/2009 | Dellinger et al. |
| 7,531,303 B2 | 5/2009 | Dorsel et al. |
| 7,534,561 B2 | 5/2009 | Sana et al. |
| 7,534,563 B2 | 5/2009 | Hargreaves |
| 7,537,936 B2 | 5/2009 | Dahm et al. |
| 7,563,600 B2 | 7/2009 | Oleinikov |
| 7,572,585 B2 | 8/2009 | Wang |
| 7,572,907 B2 | 8/2009 | Dellinger et al. |
| 7,572,908 B2 | 8/2009 | Dellinger et al. |
| 7,585,970 B2 | 9/2009 | Dellinger et al. |
| 7,588,889 B2 | 9/2009 | Wolber et al. |
| 7,595,350 B2 | 9/2009 | Xu |
| 7,604,941 B2 | 10/2009 | Jacobson |

(56) References Cited

U.S. PATENT DOCUMENTS

| | | |
|---|---|---|
| 7,608,396 B2 | 10/2009 | Delenstarr |
| 7,618,777 B2 | 11/2009 | Myerson et al. |
| 7,629,120 B2 | 12/2009 | Bennett et al. |
| 7,648,832 B2 | 1/2010 | Jessee et al. |
| 7,651,762 B2 | 1/2010 | Xu et al. |
| 7,659,069 B2 | 2/2010 | Belyaev et al. |
| 7,682,809 B2 | 3/2010 | Sampson |
| 7,709,197 B2 | 5/2010 | Drmanac |
| 7,718,365 B2 | 5/2010 | Wang |
| 7,737,088 B1 | 6/2010 | Staehler et al. |
| 7,737,089 B2 | 6/2010 | Guimil et al. |
| 7,749,701 B2 | 7/2010 | Leproust et al. |
| 7,759,471 B2 | 7/2010 | Dellinger et al. |
| 7,776,021 B2 | 8/2010 | Borenstein et al. |
| 7,790,369 B2 | 9/2010 | Stahler et al. |
| 7,790,387 B2 | 9/2010 | Dellinger et al. |
| 7,807,356 B2 | 10/2010 | Sampson et al. |
| 7,811,753 B2 | 10/2010 | Eshoo |
| 7,816,079 B2 | 10/2010 | Fischer |
| 7,855,281 B2 | 12/2010 | Dellinger et al. |
| 7,867,782 B2 | 1/2011 | Barth |
| 7,875,463 B2 | 1/2011 | Adaskin et al. |
| 7,879,541 B2 | 2/2011 | Kincaid |
| 7,879,580 B2 | 2/2011 | Carr et al. |
| 7,894,998 B2 | 2/2011 | Kincaid |
| 7,919,239 B2 | 4/2011 | Wang |
| 7,919,308 B2 | 4/2011 | Schleifer |
| 7,927,797 B2 | 4/2011 | Nobile et al. |
| 7,927,838 B2 | 4/2011 | Shannon |
| 7,932,025 B2 | 4/2011 | Carr et al. |
| 7,932,070 B2 | 4/2011 | Hogrefe et al. |
| 7,939,645 B2 | 5/2011 | Borns |
| 7,943,046 B2 | 5/2011 | Martosella et al. |
| 7,943,358 B2 | 5/2011 | Hogrefe et al. |
| 7,960,157 B2 | 6/2011 | Borns |
| 7,977,119 B2 | 7/2011 | Kronick et al. |
| 7,979,215 B2 | 7/2011 | Sampas |
| 7,998,437 B2 | 8/2011 | Berndt et al. |
| 7,999,087 B2 | 8/2011 | Dellinger et al. |
| 8,021,844 B2 | 9/2011 | Wang |
| 8,048,664 B2 | 11/2011 | Guan et al. |
| 8,053,191 B2 | 11/2011 | Blake |
| 8,058,001 B2 | 11/2011 | Crameri et al. |
| 8,058,004 B2 | 11/2011 | Oleinikov |
| 8,058,055 B2 | 11/2011 | Barrett et al. |
| 8,067,556 B2 | 11/2011 | Hogrefe et al. |
| 8,073,626 B2 | 12/2011 | Troup et al. |
| 8,076,064 B2 | 12/2011 | Wang |
| 8,076,152 B2 | 12/2011 | Robotti |
| 8,097,711 B2 | 1/2012 | Timar et al. |
| 8,154,729 B2 | 4/2012 | Baldo et al. |
| 8,168,388 B2 | 5/2012 | Gormley et al. |
| 8,173,368 B2 | 5/2012 | Staehler et al. |
| 8,194,244 B2 | 6/2012 | Wang et al. |
| 8,198,071 B2 | 6/2012 | Goshoo et al. |
| 8,202,983 B2 | 6/2012 | Dellinger et al. |
| 8,202,985 B2 | 6/2012 | Dellinger et al. |
| 8,206,952 B2 | 6/2012 | Carr et al. |
| 8,213,015 B2 | 7/2012 | Kraiczek et al. |
| 8,242,258 B2 | 8/2012 | Dellinger et al. |
| 8,247,221 B2 | 8/2012 | Fawcett |
| 8,263,335 B2 | 9/2012 | Carr et al. |
| 8,268,605 B2 | 9/2012 | Sorge et al. |
| 8,283,148 B2 | 10/2012 | Sorge et al. |
| 8,304,273 B2 | 11/2012 | Stellacci et al. |
| 8,309,307 B2 | 11/2012 | Barrett et al. |
| 8,309,706 B2 | 11/2012 | Dellinger et al. |
| 8,309,710 B2 | 11/2012 | Sierzchala et al. |
| 8,314,220 B2 | 11/2012 | Mullinax et al. |
| 8,318,479 B2 | 11/2012 | Domansky et al. |
| 8,357,489 B2 | 1/2013 | Chua et al. |
| 8,357,490 B2 | 1/2013 | Froehlich et al. |
| 8,367,016 B2 | 2/2013 | Quan et al. |
| 8,367,335 B2 | 2/2013 | Staehler et al. |
| 8,380,441 B2 | 2/2013 | Webb et al. |
| 8,415,138 B2 | 4/2013 | Leproust |
| 8,435,736 B2 | 5/2013 | Gibson et al. |
| 8,481,309 B2 | 7/2013 | Zhang et al. |
| 8,491,561 B2 | 7/2013 | Borenstein et al. |
| 8,507,226 B2 | 8/2013 | Carr et al. |
| 8,507,239 B2 | 8/2013 | Lubys et al. |
| 8,507,272 B2 | 8/2013 | Zhang et al. |
| 8,530,197 B2 | 9/2013 | Li et al. |
| 8,552,174 B2 | 10/2013 | Dellinger et al. |
| 8,569,046 B2 | 10/2013 | Love et al. |
| 8,577,621 B2 | 11/2013 | Troup et al. |
| 8,614,092 B2 | 12/2013 | Zhang et al. |
| 8,642,755 B2 | 2/2014 | Sierzchala et al. |
| 8,664,164 B2 | 3/2014 | Ericsson et al. |
| 8,685,642 B2 | 4/2014 | Sampas |
| 8,685,676 B2 | 4/2014 | Hogrefe et al. |
| 8,715,933 B2 | 5/2014 | Oliver |
| 8,716,467 B2 | 5/2014 | Jacobson |
| 8,722,585 B2 | 5/2014 | Wang |
| 8,808,896 B2 | 8/2014 | Choo et al. |
| 8,808,986 B2 | 8/2014 | Jacobson et al. |
| 8,889,851 B2 | 11/2014 | Leproust et al. |
| 9,023,601 B2 | 5/2015 | Oleinikov |
| 9,051,666 B2 | 6/2015 | Oleinikov |
| 9,073,962 B2 | 7/2015 | Fracchia et al. |
| 9,074,204 B2 | 7/2015 | Anderson et al. |
| 9,085,797 B2 | 7/2015 | Gebeyehu et al. |
| 9,133,510 B2 | 9/2015 | Andersen et al. |
| 9,139,874 B2 | 9/2015 | Myers et al. |
| 9,150,853 B2 | 10/2015 | Hudson et al. |
| 9,187,777 B2 | 11/2015 | Jacobson et al. |
| 9,216,414 B2 | 12/2015 | Chu |
| 9,217,144 B2 | 12/2015 | Jacobson et al. |
| 9,279,149 B2 | 3/2016 | Efcavitch et al. |
| 9,286,439 B2 | 3/2016 | Shapiro et al. |
| 9,295,965 B2 | 3/2016 | Jacobson et al. |
| 9,315,861 B2 | 4/2016 | Hendricks et al. |
| 9,376,677 B2 | 6/2016 | Mir |
| 9,388,407 B2 | 7/2016 | Jacobson |
| 9,403,141 B2 | 8/2016 | Banyai et al. |
| 9,409,139 B2 | 8/2016 | Banyai et al. |
| 9,422,600 B2 | 8/2016 | Ramu et al. |
| 2001/0018512 A1 | 8/2001 | Blanchard |
| 2001/0039014 A1 | 11/2001 | Bass et al. |
| 2001/0055761 A1 | 12/2001 | Kanemoto et al. |
| 2002/0012930 A1 | 1/2002 | Rothberg et al. |
| 2002/0076716 A1 | 6/2002 | Sabanayagam et al. |
| 2002/0081582 A1 | 6/2002 | Gao et al. |
| 2002/0094533 A1 | 7/2002 | Hess et al. |
| 2002/0095073 A1 | 7/2002 | Jacobs et al. |
| 2002/0119459 A1 | 8/2002 | Griffiths et al. |
| 2002/0132308 A1 | 9/2002 | Liu et al. |
| 2002/0160536 A1 | 10/2002 | Regnier et al. |
| 2003/0022207 A1 | 1/2003 | Balasubramanian et al. |
| 2003/0022317 A1 | 1/2003 | Jack et al. |
| 2003/0044781 A1 | 3/2003 | Korlach et al. |
| 2003/0058629 A1 | 3/2003 | Hirai et al. |
| 2003/0064398 A1 | 4/2003 | Barnes |
| 2003/0068633 A1 | 4/2003 | Belshaw et al. |
| 2003/0100102 A1 | 5/2003 | Rothberg et al. |
| 2003/0108903 A1 | 6/2003 | Wang et al. |
| 2003/0120035 A1 | 6/2003 | Gao et al. |
| 2003/0138782 A1 | 7/2003 | Evans |
| 2003/0143605 A1 | 7/2003 | Lok et al. |
| 2003/0148291 A1 | 8/2003 | Robotti |
| 2003/0148344 A1 | 8/2003 | Rothberg et al. |
| 2003/0171325 A1 | 9/2003 | Gascoyne et al. |
| 2003/0186226 A1 | 10/2003 | Brennan et al. |
| 2003/0228602 A1 | 12/2003 | Parker et al. |
| 2003/0228620 A1 | 12/2003 | Du |
| 2004/0043509 A1 | 3/2004 | Stahler et al. |
| 2004/0053362 A1 | 3/2004 | De Luca et al. |
| 2004/0086892 A1 | 5/2004 | Crothers et al. |
| 2004/0087008 A1 | 5/2004 | Schembri |
| 2004/0106130 A1 | 6/2004 | Besemer et al. |
| 2004/0106728 A1 | 6/2004 | McGall et al. |
| 2004/0110133 A1 | 6/2004 | Xu et al. |
| 2004/0175710 A1 | 9/2004 | Haushalter |
| 2004/0175734 A1 | 9/2004 | Stahler et al. |

(56) References Cited

U.S. PATENT DOCUMENTS

| | | |
|---|---|---|
| 2004/0191810 A1 | 9/2004 | Yamamoto |
| 2004/0248161 A1 | 12/2004 | Rothberg et al. |
| 2005/0022895 A1 | 2/2005 | Barth et al. |
| 2005/0049796 A1 | 3/2005 | Webb et al. |
| 2005/0053968 A1 | 3/2005 | Bharadwaj et al. |
| 2005/0079510 A1 | 4/2005 | Berka et al. |
| 2005/0100932 A1 | 5/2005 | Lapidus et al. |
| 2005/0112608 A1 | 5/2005 | Grossman et al. |
| 2005/0112636 A1 | 5/2005 | Hurt et al. |
| 2005/0124022 A1 | 6/2005 | Srinivasan et al. |
| 2005/0227235 A1 | 10/2005 | Carr et al. |
| 2005/0255477 A1 | 11/2005 | Carr et al. |
| 2005/0266045 A1 | 12/2005 | Canham et al. |
| 2005/0277125 A1 | 12/2005 | Benn et al. |
| 2005/0282158 A1 | 12/2005 | Landegren |
| 2006/0003381 A1 | 1/2006 | Gilmore et al. |
| 2006/0012784 A1 | 1/2006 | Ulmer |
| 2006/0012793 A1 | 1/2006 | Harris |
| 2006/0019084 A1 | 1/2006 | Pearson |
| 2006/0024678 A1 | 2/2006 | Buzby |
| 2006/0024711 A1 | 2/2006 | Lapidus et al. |
| 2006/0024721 A1 | 2/2006 | Pedersen |
| 2006/0076482 A1 | 4/2006 | Hobbs et al. |
| 2006/0078909 A1 | 4/2006 | Srinivasan et al. |
| 2006/0078927 A1 | 4/2006 | Peck et al. |
| 2006/0078937 A1 | 4/2006 | Korlach et al. |
| 2006/0134638 A1 | 6/2006 | Mulligan et al. |
| 2006/0171855 A1 | 8/2006 | Yin et al. |
| 2006/0202330 A1 | 9/2006 | Reinhardt et al. |
| 2006/0203236 A1 | 9/2006 | Ji et al. |
| 2006/0203237 A1 | 9/2006 | Ji et al. |
| 2006/0207923 A1 | 9/2006 | Li |
| 2006/0219637 A1 | 10/2006 | Killeen et al. |
| 2007/0031857 A1 | 2/2007 | Makarov et al. |
| 2007/0031877 A1 | 2/2007 | Stahler et al. |
| 2007/0054127 A1 | 3/2007 | Hergenrother et al. |
| 2007/0059692 A1 | 3/2007 | Gao et al. |
| 2007/0087349 A1 | 4/2007 | Staehler et al. |
| 2007/0099208 A1 | 5/2007 | Drmanac et al. |
| 2007/0196854 A1 | 8/2007 | Stahler et al. |
| 2007/0207482 A1 | 9/2007 | Church et al. |
| 2007/0207487 A1 | 9/2007 | Emig et al. |
| 2007/0231800 A1 | 10/2007 | Roberts et al. |
| 2007/0238104 A1 | 10/2007 | Barrett et al. |
| 2007/0238106 A1 | 10/2007 | Barrett et al. |
| 2007/0238108 A1 | 10/2007 | Barrett et al. |
| 2007/0259344 A1 | 11/2007 | Leproust et al. |
| 2007/0259345 A1 | 11/2007 | Sampas |
| 2007/0259346 A1 | 11/2007 | Gordon et al. |
| 2007/0259347 A1 | 11/2007 | Gordon et al. |
| 2007/0269870 A1 | 11/2007 | Church et al. |
| 2008/0085514 A1 | 4/2008 | Peck et al. |
| 2008/0087545 A1 | 4/2008 | Jensen et al. |
| 2008/0161200 A1 | 7/2008 | Yu et al. |
| 2008/0182296 A1 | 7/2008 | Chanda et al. |
| 2008/0214412 A1 | 9/2008 | Stahler et al. |
| 2008/0227160 A1 | 9/2008 | Kool |
| 2008/0233616 A1 | 9/2008 | Liss |
| 2008/0287320 A1 | 11/2008 | Baynes et al. |
| 2008/0308884 A1 | 12/2008 | Kalvesten |
| 2009/0036664 A1 | 2/2009 | Peter |
| 2009/0053704 A1 | 2/2009 | Novoradovskaya et al. |
| 2009/0062129 A1 | 3/2009 | McKernan et al. |
| 2009/0087840 A1 | 4/2009 | Baynes et al. |
| 2009/0088679 A1 | 4/2009 | Wood et al. |
| 2009/0105094 A1 | 4/2009 | Heiner et al. |
| 2009/0170802 A1 | 7/2009 | Stahler et al. |
| 2009/0176280 A1 | 7/2009 | Hutchison, III et al. |
| 2009/0181861 A1 | 7/2009 | Li et al. |
| 2009/0194483 A1 | 8/2009 | Robotti et al. |
| 2009/0230044 A1 | 9/2009 | Bek |
| 2009/0238722 A1 | 9/2009 | Mora-Fillat et al. |
| 2009/0239759 A1 | 9/2009 | Balch |
| 2009/0263802 A1 | 10/2009 | Drmanac |
| 2010/0004143 A1 | 1/2010 | Shibahara |
| 2010/0047805 A1 | 2/2010 | Wang |
| 2010/0051967 A1 | 3/2010 | Bradley et al. |
| 2010/0069250 A1 | 3/2010 | White, III et al. |
| 2010/0090341 A1 | 4/2010 | Wan et al. |
| 2010/0160463 A1 | 6/2010 | Wang et al. |
| 2010/0167950 A1 | 7/2010 | Juang et al. |
| 2010/0173364 A1 | 7/2010 | Evans, Jr. et al. |
| 2010/0216648 A1 | 8/2010 | Staehler et al. |
| 2010/0256017 A1 | 10/2010 | Larman et al. |
| 2010/0258487 A1 | 10/2010 | Zelechonok et al. |
| 2010/0300882 A1 | 12/2010 | Zhang et al. |
| 2011/0009607 A1 | 1/2011 | Komiyama et al. |
| 2011/0114244 A1 | 5/2011 | Yoo et al. |
| 2011/0114549 A1 | 5/2011 | Yin et al. |
| 2011/0124049 A1 | 5/2011 | Li et al. |
| 2011/0124055 A1 | 5/2011 | Carr et al. |
| 2011/0126929 A1 | 6/2011 | Velasquez-Garcia et al. |
| 2011/0171651 A1 | 7/2011 | Richmond |
| 2011/0172127 A1 | 7/2011 | Jacobson et al. |
| 2011/0201057 A1 | 8/2011 | Carr et al. |
| 2011/0217738 A1 | 9/2011 | Jacobson |
| 2011/0230653 A1 | 9/2011 | Novoradovskaya et al. |
| 2011/0254107 A1 | 10/2011 | Bulovic et al. |
| 2011/0287435 A1 | 11/2011 | Grunenwald et al. |
| 2012/0003713 A1 | 1/2012 | Hansen et al. |
| 2012/0021932 A1 | 1/2012 | Mershin et al. |
| 2012/0027786 A1 | 2/2012 | Gupta et al. |
| 2012/0028843 A1 | 2/2012 | Ramu et al. |
| 2012/0050411 A1 | 3/2012 | Mabritto et al. |
| 2012/0094847 A1 | 4/2012 | Warthmann et al. |
| 2012/0149602 A1 | 6/2012 | Friend et al. |
| 2012/0164691 A1 | 6/2012 | Eshoo et al. |
| 2012/0184724 A1 | 7/2012 | Sierzchala et al. |
| 2012/0220497 A1 | 8/2012 | Jacobson et al. |
| 2012/0231968 A1 | 9/2012 | Bruhn et al. |
| 2012/0238737 A1 | 9/2012 | Dellinger et al. |
| 2012/0258487 A1 | 10/2012 | Chang et al. |
| 2012/0264653 A1 | 10/2012 | Carr et al. |
| 2012/0270750 A1 | 10/2012 | Oleinikov |
| 2012/0270754 A1 | 10/2012 | Blake |
| 2012/0283140 A1 | 11/2012 | Chu |
| 2012/0288476 A1 | 11/2012 | Hartmann et al. |
| 2012/0289691 A1 | 11/2012 | Dellinger et al. |
| 2012/0315670 A1 | 12/2012 | Jacobson et al. |
| 2012/0322681 A1 | 12/2012 | Kung et al. |
| 2013/0005612 A1 | 1/2013 | Carr et al. |
| 2013/0017642 A1 | 1/2013 | Milgrew et al. |
| 2013/0017977 A1 | 1/2013 | Oleinikov |
| 2013/0017978 A1 | 1/2013 | Kavanagh et al. |
| 2013/0035261 A1 | 2/2013 | Sierzchala et al. |
| 2013/0045483 A1 | 2/2013 | Treusch et al. |
| 2013/0059296 A1 | 3/2013 | Jacobson et al. |
| 2013/0059761 A1 | 3/2013 | Jacobson et al. |
| 2013/0065017 A1 | 3/2013 | Sieber |
| 2013/0109595 A1 | 5/2013 | Routenberg |
| 2013/0109596 A1 | 5/2013 | Peterson et al. |
| 2013/0123129 A1 | 5/2013 | Zeiner et al. |
| 2013/0130321 A1 | 5/2013 | Staehler et al. |
| 2013/0137161 A1 | 5/2013 | Zhang et al. |
| 2013/0137173 A1 | 5/2013 | Zhang et al. |
| 2013/0137174 A1 | 5/2013 | Zhang et al. |
| 2013/0137861 A1 | 5/2013 | Leproust et al. |
| 2013/0225421 A1 | 8/2013 | Li et al. |
| 2013/0244884 A1 | 9/2013 | Jacobson et al. |
| 2013/0252849 A1 | 9/2013 | Hudson et al. |
| 2013/0261027 A1 | 10/2013 | Li et al. |
| 2013/0281308 A1 | 10/2013 | Kung et al. |
| 2013/0296192 A1 | 11/2013 | Jacobson et al. |
| 2013/0296194 A1 | 11/2013 | Jacobson et al. |
| 2013/0309725 A1 | 11/2013 | Jacobson et al. |
| 2013/0323722 A1 | 12/2013 | Carr et al. |
| 2013/0323725 A1 | 12/2013 | Peter et al. |
| 2013/0330778 A1 | 12/2013 | Zeiner et al. |
| 2014/0011226 A1 | 1/2014 | Bernick et al. |
| 2014/0018441 A1 | 1/2014 | Fracchia et al. |
| 2014/0038240 A1* | 2/2014 | Temme et al. ......... C12P 19/34 435/91.53 |
| 2014/0106394 A1 | 4/2014 | Ko et al. |
| 2014/0141982 A1 | 5/2014 | Jacobson et al. |

(56) References Cited

U.S. PATENT DOCUMENTS

| | | |
|---|---|---|
| 2014/0170665 A1 | 6/2014 | Hiddessen et al. |
| 2014/0178992 A1 | 6/2014 | Nakashima et al. |
| 2014/0274729 A1 | 9/2014 | Kurn et al. |
| 2014/0274741 A1 | 9/2014 | Hunter et al. |
| 2014/0303000 A1 | 10/2014 | Armour et al. |
| 2014/0309119 A1 | 10/2014 | Jacobson et al. |
| 2014/0309142 A1 | 10/2014 | Tian |
| 2015/0010953 A1 | 1/2015 | Lindstrom et al. |
| 2015/0012723 A1 | 1/2015 | Park et al. |
| 2015/0031089 A1 | 1/2015 | Lindstrom |
| 2015/0038373 A1 | 2/2015 | Banyai et al. |
| 2015/0065393 A1 | 3/2015 | Jacobson |
| 2015/0159152 A1 | 6/2015 | Allen et al. |
| 2015/0183853 A1 | 7/2015 | Sharma et al. |
| 2015/0191719 A1 | 7/2015 | Hudson et al. |
| 2015/0196917 A1 | 7/2015 | Kay et al. |
| 2015/0203839 A1 | 7/2015 | Jacobson et al. |
| 2015/0211047 A1 | 7/2015 | Borns |
| 2015/0225782 A1 | 8/2015 | Walder et al. |
| 2015/0240232 A1 | 8/2015 | Zamore et al. |
| 2015/0261664 A1 | 9/2015 | Goldman et al. |
| 2015/0321191 A1 | 11/2015 | Kendall et al. |
| 2015/0322504 A1 | 11/2015 | Lao et al. |
| 2015/0344927 A1 | 12/2015 | Sampson et al. |
| 2015/0353921 A9 | 12/2015 | Tian |
| 2015/0353994 A1 | 12/2015 | Myers et al. |
| 2015/0361420 A1 | 12/2015 | Hudson et al. |
| 2015/0361422 A1 | 12/2015 | Sampson et al. |
| 2015/0361423 A1 | 12/2015 | Sampson et al. |
| 2015/0368687 A1 | 12/2015 | Saaem et al. |
| 2015/0376602 A1 | 12/2015 | Jacobson et al. |
| 2016/0001247 A1 | 1/2016 | Oleinikov |
| 2016/0002621 A1 | 1/2016 | Nelson et al. |
| 2016/0002622 A1 | 1/2016 | Nelson et al. |
| 2016/0010045 A1 | 1/2016 | Cohen et al. |
| 2016/0017394 A1 | 1/2016 | Liang et al. |
| 2016/0017425 A1 | 1/2016 | Ruvolo et al. |
| 2016/0024138 A1 | 1/2016 | Gebeyehu et al. |
| 2016/0024576 A1 | 1/2016 | Chee |
| 2016/0026753 A1 | 1/2016 | Krishnaswami et al. |
| 2016/0026758 A1 | 1/2016 | Jabara et al. |
| 2016/0046973 A1 | 2/2016 | Efcavitch et al. |
| 2016/0046974 A1 | 2/2016 | Efcavitch et al. |
| 2016/0089651 A1 | 3/2016 | Banyai |
| 2016/0090592 A1 | 3/2016 | Banyai |
| 2016/0096160 A1 | 4/2016 | Banyai et al. |
| 2016/0097051 A1 | 4/2016 | Jacobson et al. |
| 2016/0102322 A1 | 4/2016 | Ravinder et al. |
| 2016/0108466 A1 | 4/2016 | Nazarenko et al. |
| 2016/0122755 A1 | 5/2016 | Hall et al. |
| 2016/0168611 A1 | 6/2016 | Efcavitch et al. |
| 2016/0229884 A1 | 8/2016 | Indermuhle et al. |
| 2016/0251651 A1 | 9/2016 | Banyai et al. |
| 2016/0264958 A1 | 9/2016 | Toro et al. |
| 2016/0303535 A1 | 10/2016 | Banyai et al. |
| 2016/0310927 A1 | 10/2016 | Banyai et al. |
| 2016/0333340 A1 | 11/2016 | Wu |
| 2016/0339409 A1 | 11/2016 | Banyai et al. |
| 2016/0340672 A1 | 11/2016 | Banyai et al. |
| 2016/0354752 A1 | 12/2016 | Banyai et al. |

FOREIGN PATENT DOCUMENTS

| | | |
|---|---|---|
| EP | 1314783 A1 | 5/2003 |
| EP | 1546387 A2 | 6/2005 |
| EP | 1153127 B1 | 7/2006 |
| EP | 1728860 A1 | 12/2006 |
| EP | 1072010 B1 | 4/2010 |
| EP | 2175021 A2 | 4/2010 |
| EP | 2330216 A1 | 6/2011 |
| EP | 2504449 A1 | 10/2012 |
| EP | 2971034 A1 | 1/2016 |
| EP | 3030682 A2 | 6/2016 |
| WO | WO-9015070 A1 | 12/1990 |
| WO | WO-9210092 A1 | 6/1992 |
| WO | WO-9210588 A1 | 6/1992 |
| WO | WO-9309668 A1 | 5/1993 |
| WO | WO-9525116 A1 | 9/1995 |
| WO | WO-9615861 A1 | 5/1996 |
| WO | WO-9710365 A1 | 3/1997 |
| WO | WO-9822541 A2 | 5/1998 |
| WO | WO-9841531 A2 | 9/1998 |
| WO | WO-9942813 A1 | 8/1999 |
| WO | WO-0013017 A2 | 3/2000 |
| WO | WO-0018957 A1 | 4/2000 |
| WO | WO-0042559 A1 | 7/2000 |
| WO | WO-0042560 A2 | 7/2000 |
| WO | WO-0042561 A2 | 7/2000 |
| WO | WO-0049142 A1 | 8/2000 |
| WO | WO-0210443 A1 | 2/2002 |
| WO | WO-0220537 A2 | 3/2002 |
| WO | WO-0224597 A2 | 3/2002 |
| WO | WO-03040410 A1 | 5/2003 |
| WO | WO-03046223 A1 | 6/2003 |
| WO | WO-03054232 A2 | 7/2003 |
| WO | WO-03064026 A1 | 8/2003 |
| WO | WO-03064027 A2 | 8/2003 |
| WO | WO-03064699 A2 | 8/2003 |
| WO | WO-03065038 A2 | 8/2003 |
| WO | WO-03066212 A2 | 8/2003 |
| WO | WO-03089605 A2 | 10/2003 |
| WO | WO-03100012 A2 | 12/2003 |
| WO | WO-2004024886 A2 | 3/2004 |
| WO | WO-2004029220 A2 | 4/2004 |
| WO | WO-2004029586 A1 | 4/2004 |
| WO | WO-2004031351 A2 | 4/2004 |
| WO | WO-2004031399 A2 | 4/2004 |
| WO | WO-2005051970 A2 | 6/2005 |
| WO | WO-2006076679 A1 | 7/2006 |
| WO | WO-2006116476 A1 | 11/2006 |
| WO | WO-2007120627 A2 | 10/2007 |
| WO | WO-2007137242 A2 | 11/2007 |
| WO | WO-2008006078 A2 | 1/2008 |
| WO | WO-2008027558 A2 | 3/2008 |
| WO | WO-2008054543 A2 | 5/2008 |
| WO | WO-2008109176 A2 | 9/2008 |
| WO | WO-2010025310 A2 | 3/2010 |
| WO | WO-2010025566 A1 | 3/2010 |
| WO | WO-2011053957 A2 | 5/2011 |
| WO | WO-2011056872 A2 | 5/2011 |
| WO | WO-2011066185 A1 | 6/2011 |
| WO | WO-2011066186 A1 | 6/2011 |
| WO | WO-2011085075 A2 | 7/2011 |
| WO | WO-2011143556 A1 | 11/2011 |
| WO | WO-2011150168 A1 | 12/2011 |
| WO | WO-2011161413 A2 | 12/2011 |
| WO | WO-2012061832 A1 | 5/2012 |
| WO | WO-2012078312 A2 | 6/2012 |
| WO | WO-2012149171 A1 | 11/2012 |
| WO | WO-2012154201 A1 | 11/2012 |
| WO | WO-2013032850 A2 | 3/2013 |
| WO | WO-2013036668 A1 | 3/2013 |
| WO | WO-2013101896 A1 | 7/2013 |
| WO | WO-2013177220 A1 | 11/2013 |
| WO | WO-2014004393 A1 | 1/2014 |
| WO | WO-2014035693 A2 | 3/2014 |
| WO | WO-2014093694 A1 | 6/2014 |
| WO | WO-2014151696 A1 | 9/2014 |
| WO | WO-2014160004 A1 | 10/2014 |
| WO | WO-2014160059 A1 | 10/2014 |
| WO | WO-2015017527 A2 | 2/2015 |
| WO | WO-2015021080 A2 | 2/2015 |
| WO | WO-2015021280 A1 | 2/2015 |
| WO | WO-2015081114 A2 | 6/2015 |
| WO | WO-2015090879 A1 | 6/2015 |
| WO | WO-2015120403 A1 | 8/2015 |
| WO | WO-2015160004 A1 | 10/2015 |
| WO | WO-2015175832 A1 | 11/2015 |
| WO | WO-2016007604 A1 | 1/2016 |
| WO | WO-2016022557 A1 | 2/2016 |
| WO | WO-2016053883 A1 | 4/2016 |
| WO | WO-2016065056 A1 | 4/2016 |
| WO | WO-2016126882 A1 | 8/2016 |

(56) References Cited

FOREIGN PATENT DOCUMENTS

| WO | WO-2016126987 A1 | 8/2016 |
|---|---|---|
| WO | WO-2016172377 A1 | 10/2016 |
| WO | WO-2016183100 A1 | 11/2016 |

OTHER PUBLICATIONS

Crick. On protein synthesis. Symp Soc Exp Biol., 12:138-163,1958.
Doudna et al. Genome editing. The new frontier of genome engineering with CRISPR-Cas9. Science 346(6213):1258096-1-1258096-9, 2014.
Genomics 101. An Introduction to the Genomic Workflow. 2016 edition, 64 pages. Available at: http://www.frontlinegenomics.com/magazine/6757/genomics-101/.
Hughes et al. Principles of early drug discovery. Br J Pharmacol 162(2):1239-1249, 2011.
Liu et al., Comparison of Next-Generation Sequencing Systems. Journal of Biomedicine and Biotechnology, 11 pages, 2012.
PCT Patent Application No. PCT/US2016/028699 International Search Report and Written Opinion dated Jul. 29, 2016.
PCT Patent Application No. PCT/US2016/031674 International Search Report and Written Opinion dated Aug. 11, 2016.
Pirrung. How to make a DNA chip. Angew. Chem. Int. Ed., 41:1276-1289, 2002.
Poster. Reimagine Genome Scale Research. 2016, 1 page. Available at http://www2.twistbioscience.com/Oligo_Pools_CRISPR_poster.
Powers et al. Optimal strategies for the chemical and enzymatic synthesis of bihelical deoxyribonucleic acids. J Am Chem Soc., 97(4):875-884, 1975.
Sierzchala, Agnieszka B. et al., "Solid-phase oligodeoxynucleotide synthesis : a two-step cycle using peroxy anion eprotection." J. Am. Chem. Soc., vol. 125, No. 44, 13427-13441 (2003).
Reimagine SequenceSpace, Reimagine Research, Twist Bioscience, Product Brochure, Published Apr. 6, 2016 online at: www2.twistbioscience.com/TB_Product_Brochure_04.2016, 8 pages.
Saaem et al., In situ synthesis of DNA microarray on functionalized cyclic olefin copolymer substrate ACS Applied Materials & Interfaces, 2(2):491-497, 2010.
Singh-Gasson, Sangeet et al., Maskless fabrication of light-directed olxyonucleotide microarrays using a digital micromirror array, Nature Biotechnology, vol. 17, 974-978 (Oct. 1999).
Taylor et al., Impact of surface chemistry and blocking strategies on DNA microarrays. Nucleic Acids Research, 31(16):e87, 19 pages, 2003.
U.S. Appl. No. 14/452,429 Notice of Allowance dated Jun. 7, 2016.
U.S. Appl. No. 14/885,962 Office Action dated Sep. 8, 2016.
U.S. Appl. No. 14/885,963 Notice of Allowance dated May 24, 2016.
U.S. Appl. No. 14/885,963 Office Action dated Feb. 5, 2016.
U.S. Appl. No. 14/885,965 Office Action dated Jul. 7, 2016.
ATDBio, "Nucleic Acid Structure," Nucleic Acids Book, 9 pages, published on Jan. 22, 2005. from: http://www.atdbio.com/content/5/Nucleic-acid-structure.
ATDBio, "Solid-Phase Oligonucleotide Synthesis," Nucleic Acids Book, 20 pages, Published on Jul. 31, 2011. from: http://www.atdbio.com/content/17/Solid-phase-oligonucleotide-synthesis.
Barton et al., A desk electrohydrodynamic jet printing system. Mechatronics, 20:611-616, 2010.
Blanchard, et al., "High-Density Oligonucleotide Arrays," Biosensors & Bioelectronics, 11(6/7):687-690, 1996.
Buermans et al., "Next Generation sequencing technology: Advances and applications," Biochimica et Biophysica Acta (BBA)—Molecular Basis of Disease, 1842:1931-1941, 2014.
Cleary et al., "Production of complex nucleic acid libraries using highly parallel in situ oligonucleotide synthesis," Nature Methods, 1(13):241-248, 2004.
Fodor et al. "Light-Directed, Spatially Addressable Parallel Chemical Synthesis," Science, 251(4995):767-773, 1991.

Kim et al., High-resolution patterns of quantum dots formed by electrohydrodynamic jet printing for light-emitting diodes. Nano Letters, 15:969-973, 2015.
Kosuri and Church, "Large-scale de novo DNA synthesis: technologies and applications," Nature Methods, 11:499-507, 2014. Available at: http://www.nature.com/nmeth/journal/v11/n5/full/nmeth.2918.html.
Krayden, Inc., A Guide to Silane Solutions. Silane coupling agents. 7 pages. Published on May 31, 2005 at: http://krayden.com/pdf/xia_silane_chemistry.pdf.
Lausted et al., "POSaM: a fast, flexible, open-source, inkjet oligonucleotide synthesizer and microarrayer," Genome Biology, 5:R58, 17 pages, 2004. available at https://www.ncbi.nlm.nih.gov/pmc/articles/PMC507883/.
Leproust et al., "Synthesis of high-quality libraries of long (150mer) oligonucleotides by a novel depurination controlled process," Nucleic Acids Research, 35(8):2522-2540, 2010.
McBride & Caruthers, "An investigation of several deoxynucleoside phosphoramidites useful for synthesizing deoxyoligonucleotides." Tetrahedron Lett. 24: 245-248, 1983.
PCT Patent Application No. PCT/US2016/052336 International Search Report and Written Opinion dated Dec. 7, 2016.
Pray. "Discovery of DNA Structure and Function: Watson and Crick," Nature Education, 2008, 6 pages. available at: http://www.nature.com/scitable/topicpage/discovery-of-dna-structure-and-function-watson-397.
Quan et al., "Parallel on-chip gene synthesis and application to optimization of protein expression," Nature Biotechnology, 29(5):449-452, 2011.
Raje and Murma, A Review of electrohydrodynamic-inkjet printing technology. International Journal of Emerging Technology and Advanced Engineering, 4(5):174-183, 2014.
The Hood Laboratory, "Beta Group." Assembly Manual for the POSaM: The ISB Piezoelelctric Oligonucleotide Synthesizer and Microarrayer, Inkjet Microarrayer Manual Version 1.2, 50 pages, May 28, 2004.
U.S. Appl. No. 15/233,835 Restriction Requirement dated Nov. 4, 2016.
U.S. Appl. No. 15/245,054 Office Action dated Oct. 19, 2016.
Wijshoff, Herman. Structure and fluid-dynamics in Piezo inkjet printheads. Thesis. Venio, The Netherlands, published 2008, p. 1-185.
Xiong et al., Chemical gene synthesis: Strategies, softwares, error corrections, and applications. FEMS Microbiol. Rev., 32:522-540, 2008.
Adessi, et al. Solid phase DNA amplification: characterisation of primer attachment and amplification mechanisms. Nucleic Acids Res. Oct. 15, 2000;28(20):E87.
Alexeyev, Mikhail F. et al., "Gene synthesis, bacterial expression and purification of the Rickettsia prowazekii ATP/ADP translocase", Biochimica et Biophysics Acta, vol. 1419, 299-306 (1999).
Al-Housseiny et al., Control of interfacial instabilities using flow geometry. Nature Physics, 8:747-750 (2012); Published online at: DOI:10.1038/NPHYS2396.
Amblard, Francois et al., "A magnetic manipulator for studying local rheology and micromechanical properties of biological systems", Rev. Sci.Instrum., vol. 67, No. 3, 818-827, Mar. 1996.
Arkles, et al. The Role of Polarity in the Structure of Silanes Employed in Surface Modification. Silanes and Other Coupling Agents. 2009; 5:51-64.
Arkles, Hydrophobicity, Hydrophilicity. Reprinted with permission from the Oct. 2006 issue of Paint & Coatings Industry magazine, Retrieved on Mar. 19, 2016, 10 pages.
Assi, Fabiano et al., "Massive-parallel adhesion and reactivity-measurements using simple and inexpensive magnetic tweezers", J. Appl. Phys., vol. 92, No. 9, 5584-5586, Nov. 1, 2002.
Au, Lo-Chun et al. "Gene synthesis by a LCR-based approach: high level production of Leptin-L54 using synthetic gene in *Escherichia coli*", Biochemical and Biophysical Research Communications, vol. 248, 200-203 (1998).

(56) References Cited

OTHER PUBLICATIONS

Baedeker, Mathias et al., Overexression of a designed 2.2kb gene of eukaryotic phenylalanine ammonialyase in *Escherichia coli*•. FEBS Letters, vol. 457, 57-60 (1999).
Barbee, et al. Magnetic Assembly of High-Density DNA Arrays for Genomic Analyses. Anal Chem. Mar. 15, 2008; 80(6): 2149-2154.
Beaucage, et al. Advances in the synthesis of oligonucleotides by the phosphoramidite approach. Tetrahedron. 1992; 48:2223-2311.
Beaucage, et al. Deoxynucleoside phosphoramidites—A new class of key intermediates for deoxypolynucleotide synthesis. Tetrahedron Lett. 1981; 22(20):1859-1862.
Beaulieu, Martin et al., "PCR candidate region mismatch scanning adaptation to quantitative, highthroughput genotyping", Nucleic Acids Research, vol. 29, No. 5, 1114-1124 (2001).
Beigelman, et al. Base-modified phosphoramidite analogs of pyrimidine ribonucleosides for RNA structure-activity studies. Methods Enzymol. 2000;317:39-65.
Biswas, Indranil et al., "Identification and characterization of a thermostable MutS homolog from Thennus aquaticus", The Journal of Biological Chemistry, vol. 271, No. 9, 5040-5048 (Mar. 1, 1996).
Biswas, Indranil et al., "Interaction of MutS/crotein with the major and minor grooves of a heteroduplex DNA", The Journal of Biological Chemistry, vol. 272, No. 20, 13355-13364 (May 1, 1997).
Bjornson, Keith P. et al., "Differential and simultaneous adenosine Di- and Tri~hosphate binding by MutS", The Journal of Biological Chemistry, vol. 278, No. 20, 18557-18562 (May 16, 2003).
Blanchard, et al. High-Density Oligonucleotide Arrays. Biosens. & Bioelectronics. 1996; 11:687-690.
Blanchard, in: *Genetic Engineering, Principles and Methods*, vol. 20, Ed. J. Sedlow, New York: Plenum Press, p. 111-124, 1979.
Butler, et al. In situ synthesis of oligonucleotide arrays by using surface tension. J Am Chem Soc. Sep. 19, 2001;123(37):8887-94.
Carr, et al. Protein-mediated error correction for de novo DNA synthesis. Nucleic Acids Res. Nov. 23, 2004;32(20):e162.
Caruthers, Chemical synthesis of deoxyoligonucleotides by the phosphoramidite method. In Methods in Enzymology, Chapter 15, 154:287-313 (1987).
Caruthers. Gene synthesis machines: DNA chemistry and its uses. Science. Oct. 18, 1985;230(4723):281-5.
Casmiro, Danilo R. et al., "PCR-based gene synthesis and protein NMR spectroscopy", Structure, vol. 5, No. 11, 1407-1412 (1997).
Cello, et al. Chemical synthesis of poliovirus cDNA: generation of infectious virus in the absence of natural template. Science. Aug. 9, 2002;297(5583):1016-8. Epub Jul. 11, 2002.
Chalmers, et al. Scaling up the ligase chain reaction-based approach to gene synthesis. Biotechniques. Feb. 2001;30(2):249-52.
Chan, et al. Natural and engineered nicking endonucleases—from cleavage mechanism to engineering of strand-specificity. Nucleic Acids Res. Jan. 2011; 39(1): 1-18.
Chen, et al. Chemical modification of gene silencing oligonucleotides for drug discovery and development. Drug Discov Today. Apr. 15, 2005;10(8):587-93.
Cheng, et al. High throughput parallel synthesis of oligonucleotides with 1536 channel synthesizer. Nucleic Acids Res. Sep. 15, 2002;30(18):e93.
Cho, et al. Capillary passive valve in microfluidic systems. NSTI-Nanotech. 2004; 1:263-266.
Chrisey et al., Fabrication of patterned DNA surfaces. Nucleic Acids Research, 24(15):3040-3047 (1996).
Chung et al., One-step preparation of competent*Escherichia coli*:Transformation and storage of bacterial cells in the same solution. Proc Natl Acad Sci U S A. Apr. 1989;86(7):2172-2175.
Cleary, et al. Production of complex nucleic acid libraries using highly parallel in situ oligonucleotide synthesis. Nat Methods. Dec. 2004;1(3):241-8. Epub Nov. 18, 2004.
Cutler, David J. ef al., "High-throughput variation detection and genotyping using microarrays", Genome Research, vol. 11, 1913-19 (2001).

Dahl, et al. Circle-to-circle amplification for precise and sensitive DNA analysis. Proc Natl Acad Sci U S A. Mar. 30, 2004;101(13):4548-53.
De Mesmaeker, et al. Backbone modifications in oligonucleotides and peptide nucleic acid systems. Curr Opin Struct Biol. Jun. 1995;5(3):343-55.
Deamer, David W. et al., "Characterization of nucleic acids by nanopore analysis", Ace. Cham. Res., vol. 35, No. 10, 817-825 (2002).
Deaven, The Human Genome Project: Recombinant clones for mapping and sequencing DNA. Los Alamos Science, 20:218-249, 1992.
Deng et al., Targeted bisulfite sequencing reveals changes in DNA methylation associated with nuclear reprogramming. Nature Biotechnology, 27:352-360 (2009)—http://www.nature.com/nbt/journal/v27/n4/abs/nbt.1530.html.
Dietrich, Rudiger.et al., "Gene assembly based on blunt-ended double-stranded DNA-modules", Biotechnology Techniques, vol. 12, No. 1, 49-54 (Jan. 1998).
Dower et al., High efficiency transformation of *E.coli* by high voltage electroporation. Nucleic Acids Res. 16(13):6127-45 (1988).
Dressman, et al. Transforming single DNA molecules into fluorescent magnetic particles for detection and enumeration of genetic variation. Proc Natl Acad Sci U S A. Jul. 22, 2003;100(15):8817-22.
Drmanac, et al. Human genome sequencing using unchained base reads on self-assembling DNA nanoarrays. Science. Jan. 1, 2010;327(5961):78-81. doi: 10.1126/science.1181498.
Droege and Hill, The Genome Sequencer FLXTM System—Longer reads, more applications, straight forward bioinformatics and more complete data sets. Journal of Biotechnology, 136:3-10, 2008.
Duffy, et al. Rapid Prototyping of Microfluidic Systems in Poly(dimethylsiloxane). Anal Chem. Dec. 1, 1998;70(23):4974-84. doi: 10.1021/ac980656z.
Duggan, et al. Expression profiling using cDNA microarrays. Nat Genet. 1999 21(1 Suppl):10-14.
Eadie, et al. Guanine modification during chemical DNA synthesis. Nucleic Acids Res. Oct. 26, 1987;15(20):8333-49.
Eisen, Jonathan A., "A phylogenomic study of the MutS family of proteins", Nucleic Acids Research, vol. 26, No. 18, 4291-4300 (1998).
Ellis, et al. DNA assembly for synthetic biology: from parts to pathways and beyond. Integr Biol (Camb). Feb. 2011;3(2):109-18. doi: 10.1039/c0ib00070a. Epub Jan. 19, 2011.
El-Sagheer, et al. Biocompatible artificial DNA linker that is read through by DNA polymerases and is functional in *Escherichia coli*. Proc Natl Acad Sci U S A. Jul. 12, 2011;108(28):11338-43. doi: 10.1073/pnas.1101519108. Epub Jun. 27, 2011.
Elsner et al., 172 nm excimer VUV-triggered photodegradation and micropatterning of aminosilane films, Thin Solid Films, 517:6772-6776 (2009).
Engler, et al. A one pot, one step, precision cloning method with high throughput capability. PLoS One. 2008;3(11):e3647. doi: 10.1371/journal.pone.0003647. Epub Nov. 5, 2008.
Engler, et al. Golden gate shuffling: a one-pot DNA shuffling method based on type IIs restriction enzymes. PLoS One. 2009;4(5):e5553. doi: 10.1371/journal.pone.0005553. Epub May 14, 2009.
Evans et al., DNA Repair Enzymes. Current Protocols in Molecular Biology. 84:III:3.9:3.9.1-3.9.12—http://www.ncbi.nlm.nih.gov/pubmed/18972391 (Published online Oct. 1, 2008) Abstract only provided.
Fahy, et al. Self-sustained sequence replication (3SR): an isothermal transcription-based amplification system alternative to PCR. PCR Methods Appl. Aug. 1991;1(1):25-33.
Fedoryak, Olesya D. et al., "Brominated hydroxyquinoline as a photolabile protecting group with sensitivity to multiphoton excitation", Org. Lett., vol. 4, No. 2 , 3419-3422 (2002).
Ferretti et al., Total synthesis of a gene for bovine rhodopsin. PNAS, 83:599-603 (1986).
Fodor, et al. Light-directed, spatially addressable parallel chemical synthesis. Science. Feb. 15, 1991;251(4995):767-73.
Foldesi, et al. The synthesis of deuterionucleosides. Nucleosides Nucleotides Nucleic Acids. Oct.-Dec. 2000;19(10-12):1615-56.

(56) References Cited

OTHER PUBLICATIONS

Frandsen, et al. Efficient four fragment cloning for the construction of vectors for targeted gene replacement in filamentous fungi. BMC Molecular Biology 2008, 9:70.
Frandsen. Experimental setup. Dec. 7, 2010, 3 pages. http://www.rasmusfrandsen.dk/experimental_setup.htm.
Frandsen. The USER Friendly technology. USER cloning. Oct. 7, 2010, 2 pages. http://www.rasmusfrandsen.dk/user_cloning.htm.
Fullwood et al., Next-generation DNA sequencing of paired-end tags [PET] for transcriptome and genome analysis Genome Research, 19:521-532, 2009.
Galneder. et al., Microelectrophoresis of a bilayer-coated silica bead in an optical trap: application to enzymology. Biophysical Journal, vol. 80, No. 5, 2298-2309 (May 2001).
Gao, et al. A flexible light-directed DNA chip synthesis gated by deprotection using solution photogenerated acids. Nucleic Acids Res. Nov. 15, 2001;29(22):4744-50.
Gao, et al. Thermodynamically balanced inside-out (TBIO) PCR-based gene synthesis: a novel method of primer design for high-fidelity assembly of longer gene sequences. Nucleic Acids Res. Nov. 15, 2003;31(22):e143.
Garaj, et al. Graphene as a subnanometre trans-electrode membrane. Nature. Sep. 9, 2010;467(7312):190-3. doi: 10.1038/nature09379.
Garbow, Norbert et al., "Optical tweezing electroghoresis of isolated, highly charged colloidal spheres", Colloids and Surfaces A: Physiochem. Eng. Aspects, vol. 195, 227-241 (2001).
Geu-Flores, et al. USER fusion: a rapid and efficient method for simultaneous fusion and cloning of multiple PCR products. Nucleic Acids Res. 2007;35(7):e55. Epub Mar. 27, 2007.
Gibson, et al. Complete chemical synthesis, assembly, and cloning of a Mycoplasma genitalium genome. Science. Feb. 29, 2008;319(5867):1215-20. doi: 10.1126/science.1151721. Epub Jan. 24, 2008.
Gosse, Charlie et al. "Magnetic tweezers: micromanipulation and force measurement at the molecular level", Biophysical Journal, vol. 8, 3314-3329 (Jun. 2002).
Grovenor. Microelectronic materials. Graduate Student Series in Materials Science and Enginering. Bristol, England: Adam Hilger, 1989; p. 113-123.
Haber, Charbel et al., Magnetic tweezers for DNA micromanipulation, Rev. Sci. Instrum., vol. 71, No. 12, 4561-4570 (Dec. 2000).
Hanahan and Cold Spring Harbor Laboratory, Studies on transformation of *Escherichia coli* with plasmids. J. Mol. Biol. 166:557-580 (1983).
Hanahan et al., Plasmid transformation of *Escherichia coli* and other bacteria. Methods Enzymol, vol. 204, p. 63-113 (1991).
Harada, et al. Unexpected substrate specificity of T4 DNA ligase revealed by in vitro selection. Nucleic Acids Res. May 25, 1993;21(10):2287-91.
Heckers Karl H. et al., "Error analysis of chemically synthesized polynucleotides", BioTechniques, vol. 24, No. 2, 256-260 (1998).
Herzer et al.: Fabrication of patterned silane based self-assembled monolayers by photolithography and surface reactions on silicon-oxide substrates Chem. Commun., 46:5634-5652 (2010).
Hoover et al., "DNAWorks: an automated method for designing oligonucleotides for PCR-based gene synthesis", Nucleic Acids Research, vol. 30, No. 10, e43, 7 pages (2002).
Hosu, Basarab G. et al., "Magnetic tweezers for intracellular applications", Rev. Sci. Instrum., vol. 74, No. 9, 4158-4163 (Sep. 2003).
Huang, Hayden et al., "Three-dimensional cellular deformation analysis with a two-photon magnetic manipulator workstation", Biophysical Journal, vol. 82, No. 4, 2211-2223 (Apr. 2002).
Hughes, et al. Expression profiling using microarrays fabricated by an ink-jet oligonucleotide synthesizer. Nat Biotechnol. Apr. 2001;19(4):342-7.
Hutchison, et al. Cell-free cloning using phi29 DNA polymerase. Proc Natl Acad Sci U S A. Nov. 29, 2005;102(48):17332-6. Epub Nov. 14, 2005.
Jackson, Brian A. et al., "Recognition of DNA base mismatches by a rhodium intercalator", J. Am. Chem. Soc., vol. 19, 12986-12987 (1997).
Jacobs and Schar, DNA glycosylases: In DNA repair and beyond. Chromosome, 121:1-20 (2012)—http://www.ncbi.nlm.nih.gov/pmc/articles/PMC3260424/.
Jeffrey M. Calvert, Lithographically patterned self-assembled films. In:*Organic Thin Films and Surfaces: Directions for the Nineties*, vol. 20, p. 109, ed. By Abraham Ulman, San Diego: Academic Press, 1995.
Karagiannis and Ei-Osta, RNA interference and potential therapeutic applications of short interfering RNAs Cancer Gene Therapy, 12:787-795, 2005.
Ke, Song-Hua et al., "Influence of neighboring base pairs on the stability of single base bulges and base pairs in a DNA fragment", Biochemistry, Vo. 34, 4593-4600 (1995).
Kelley, Shana, et al. Single-base mismatch detection based on charge transduction through DNA, Nucleic Acids Research, vol. 27, No. 24, 4830-4837 (1999).
Kim, Yang-Gyun et al., "Chimeric restriction endonuclease", Proc. Natl. Acad. Sci. USA, vol. 91, 883-887 (Feb. 1994).
Kim, Yang-Gyun, "The interaction between Z-ONA and the Zab domain of double-stranded RNA adenosine deaminase characterized using fusion nucleases", The Journal of Biological Chemistry, vol. 274, No. 27, 19081-19086 (1999).
Kim, Yan-Gyun et al., "Site-specific cleavage of DNA-RNA hybrids by zinc finger/Fok I cleavage domain fusions" Gene, vol. 203, 43-49 (1997).
Kinde et al., Detection and quantification of rare mutations with massively parallel sequencing PNAS, 108(23):9530-9535, 2011.
Kodumal, et al. Total synthesis of long DNA sequences: synthesis of a contiguous 32-kb polyketide synthase gene cluster. Proc Natl Acad Sci U S A. Nov. 2, 2004;101(44):15573-8. Epub Oct. 20, 2004.
Kong et al., Parallel gene synthesis in a microfluidic device. Nucleic Acids Res., 35(8):e61 (2007).
Kong. Microfluidic Gene Synthesis. MIT Thesis. Submitted to the program in Media Arts and Sciences, School of Architecture and Planning, in partial fulfillment of the requirements for the degree of Doctor of Philosophy in Media Arts and Sciences at the Massachusetts Institute of Technology. 143 pages Jun. 2008.
Kopp, Martin U. et al., "Chemical amplification: continuous-flow PCR on a chip", Science, vol. 280, 1046-1048 (May 15, 1998).
Kosuri et al., A scalable gene synthesis platform using high-fidelity DNA microchips Nat.Biotechnol., 28(12):1295-1299, 2010.
Lagally, E.T. et al., "Single-molecule DNA amplification and analysis in an integrated microfluidic device" Anal. Chem., vol. 73, No. 565-570 (Feb. 1, 2001).
Lahue, R.S. et. al., "DNA mismatch correction in a defined system", Science, vol. 425; No. 4914, 160-164 (Jul. 14, 1989).
Lambrinakos, A. et al., "Reactivity of potassium permanganate and tetraethylammonium chloride with mismatched bases and a simple mu ation detection protoco",Nucleic Acids Research, vol. 27, No. 8, 1866-1874 (1999).
Landegren, et al. A ligase-mediated gene detection technique. Science. Aug. 26, 1988;241(4869):1077-80.
Lang, Matthew J. et al., "An automated two-dimensional optical force clamp for single molecule studies", Biophysical Journal, vol. 83, 491•501 (Jul. 2002).
Lashkari, et al. An automated multiplex oligonucleotide synthesizer: development of high-throughput low-cost DNA synthesis. Proc Natl Acad Sci U S A. Aug. 15, 1995;92(17):7912-5.
Leamon, et al. A massively parallel PicoTiterPlate based platform for discrete picoliter-scale polymerase chain reactions. Electrophoresis. Nov. 2003;24(21):3769-77.
Lee, Covalent end-immobilization of oligonucleotides onto solid surfaces. Thesis submitted to the Department of Chemical Engineering in Partial Fulfillment of the Requirements for the Degree of Doctor of Philosophy in Chemical Engineering at the Massachusetts Institute of Technology. Aug. 2001, 315 pages.
Lee, C.S. et al., "Microelectromagnets for the control of magnetic nanoparticles", Appl. Phys. Lett., vol. 79, No. 20, 3308-3310 (Nov. 12, 2001).

(56) References Cited

OTHER PUBLICATIONS

Lee, et al. A microfluidic oligonucleotide synthesizer. Nucleic Acids Research 2010 vol. 38(8):2514-2521. DOI: 10.1093/nar/gkq092.
Leproust, et al. Agilent's Microarray Platform: How High-Fidelity DNA Synthesis Maximizes the Dynamic Range of Gene Expression Measurements. 2008; p. 1-12. http://www.miltenyibiotec.com/~/media/Files/Navigation/Genomic%20Services/Agilent_DNA_Microarray_Platform.ashx.
Leproust, et al. Synthesis of high-quality libraries of long (150mer) oligonucleotides by a novel depurination controlled process. Nucleic Acids Research. 2010; 38(8):2522-2540.
Lesnikowski, et al. Nucleic acids and nucleosides containing carboranes. J Organometallic Chem. 1999; 581:156-169.
Leumann. DNA analogues: from supramolecular principles to biological properties. Bioorg Med Chem. Apr. 2002;10(4):841-54.
Levene, et al. Zero-mode waveguides for single-molecule analysis at high concentrations. Science. Jan. 31, 2003;299(5607):682-6.
Lipshutz, Robert J. et al., "High density synthetic oligonucleotide arrays", Nature Genetics Supplement, vol. 21, 20-24 (Jan. 1999).
Lishanski, Alia et al., "Mutation detection by mismatch binding protein, MutS, in amplified DNA: application to the cystic fibrosis gene", Proc. Natl. Acad. Sci. USA, vol. 91, 2674-2678 (Mar. 1994).
Liu, et al. Enhanced Signals and Fast Nucleic Acid Hybridization by Microfluidic Chaotic Mixing. Angew. Chem. Int. Ed. 2006; 45:3618-3623.
Lizardi, et al. Mutation detection and single-molecule counting using isothermal rolling-circle amplification. Nat Genet. Jul. 1998;19(3):225-32.
Li, Lin et al., "Functional domains in Fok I restriction endonuclease", Proc. Natl. Acad. Sci. USA, vol. 89, 4275-4279 (May 1992).
Lu, A.-Lien et al., "Methyl-directed repair of DNA base-pair mismatches in vitro",Proc. Natl. Acad. Sci. USA, vol. 80, 4639-4643 (Aug. 1983).
Lund, et al. A validated system for ligation-free uracilexcision based assembly of expression vectors for mammalian cell engineering. DTU Systems of Biology. 2011. 1 page. http://www.lepublicsystemepco.com/files/modules/gestion_rubriques/REF-B036-Lund_Anne%20Mathilde.pdf.
Ma, et al. DNA synthesis, assembly and application in synthetic biology. Current Opinion in Chemical Biology. 2012; 16:260-267.
Ma et al., Versatile surface functionalization of cyclic olefin copolymer (COC) with sputtered SiO2 thin film for potential BioMEMS applications. Journal of Materials Chemistry, DOI: 10.1039/b904663a, 11 pages (2009).
Mahato et al., Modulation of gene expression by antisense and antigene oligodeoxynucleotides and small interfering RNA Expert Opin. Drug Delivery, 2(1):3-28, 2005.
Margulies, et al. Genome sequencing in open microfabricated high-density picolitre reactors. Nature. Sep. 15, 2005;437(7057):376-80. Epub Jul. 31, 2005.
Matteucci, et al. Synthesis of deoxyoligonucleotides on a polymer support. J. Am. Chem. Soc. 1981; 103(11):3185-3191.
Matzas et al., Next generation gene synthesis by targeted retrieval of bead-immobilized, sequence verified DNA clones from a high throughput pyrosequencing device. Nat.Biotechnol., 28(12):1291-1294, 2010.
McGall, et al. Light-directed synthesis of high-density oligonucleotide arrays using semiconductor photoresists. Proc Natl Acad Sci U S A. Nov. 26, 1996;93(24):13555-60.
McGall, et al. The Efficiency of Light-Directed Synthesis of DNA Arrays on Glass Substrates. J. Am. Chem. Soc. 1997; 119(22):5081-5090.
Mei et al., Cell-free protein synthesis in microfluidic array devices Biotechnol.Prog., 23(6):1305-1311, 2007.
Mendel-Hartvig. Padlock probes and rolling circle amplification. New possibilities for sensitive gene detection. Comprehensive Summaries of Uppsala Dissertations from the Faculty of Medicine 1175. Uppsala University. 2002, 39 pages. http://www.diva-portal.org/smash/get/diva2:161926/FULLTEXT01.pdf.

Meyers and Friedland, Knowledge-based simulation of genetic regulation in bacteriophage lambda Nucl.Acids Research, 12(1):1-16, 1984.
Mitra, et al. In situ localized amplification and contact replication of many individual DNA molecules. Nucleic Acids Res. Dec. 15, 1999;27(24):e34.
Muller, Caroline et al. "Protection and labelling of thymidine by a fluorescent photolabile group", Helvetica Chimica Acta, vol. 84, 3735-3741 (2001).
Nakatani, Kazuhiko et al., "Recognition of a single guanine bulge by 2-Acylamino-1,8-naphthyridine", J. Am. Chem. Soc., vol. 122, 2172-2177 (2000).
Nishikura, A short primer on RNAi: RNA-directed RNA polymerase acts as a key catalyst Cell, 107:415-418, 2001.
Nour-Eldin, et al. USER Cloning and USER Fusion: The Ideal Cloning Techniques for Small and Big Laboratories. Plant Secondary Metabolism Engineering. Methods in Molecular Biology vol. 643, 2010, pp. 185-200.
Ochman, et al. Genetic applications of an inverse polymerase chain reaction. Genetics. Nov. 1988;120(3):621-3.
Pan, et al. An approach for global scanning of single nucleotide variations. Proc Natl Acad Sci U S A. Jul. 9, 2002;99(14):9346-51.
Pankiewicz. Fluorinated nucleosides. Carbohydr Res. Jul. 10, 2000;327(1-2):87-105.
PCT Patent Application No. PCT/US14/049834 International Preliminary Report on Patentability dated Feb. 18, 2016.
PCT Patent Application No. PCT/US2015/043605 International Search Report and Written Opinion dated Jan. 6, 2016.
PCT Patent Application No. PCT/US2015/043605 "Invitation to Pay Additional Fees and, where applicable, protest fee," dated Oct. 28, 2015.
PCT Patent Application No. PCT/US2016/016459 International Search Report and Written Opinion dated Apr. 13, 2016.
PCT Patent Application No. PCT/US2016/016636 International Search Report and Written Opinion dated May 2, 2016.
PCT Patent Application No. PCT/US2014/049834 International Search Report and Written Opinion mailed Mar. 19, 2015.
PCT Patent Application No. PCT/US2014/049834, "Invitation to Pay Additional Fees and, where applicable, protest fee," mailed Jan. 5, 2015.
Pease, et al. Light-generated oligonucleotide arrays for rapid DNA sequence analysis. Proc Natl Acad Sci U S A. May 24, 1994;91(11):5022-6.
Peisajovich, et al. BBF RFC 28: A method for combinatorial multi-part assembly based on the type-lis restriction enzyme aarl. Sep. 16, 2009, 7 pages.
Pellois, et al. "Individually addressable parallel peptide synthesis on microchips", Nature Biotechnology, vol. 20, 922-926 (Sep. 2002).
Petersen, et al. LNA: a versatile tool for therapeutics and genomics. Trends Biotechnol. Feb. 2003;21(2):74-81.
Pierce, et al. Linear-after-the-exponential polymerase chain reaction and allied technologies. Real-time detection strategies for rapid, reliable diagnosis from single cells. Methods Mol Med. 2007;132:65-85.
Pon. Solid-phase supports for oligonucleotide synthesis. Methods Mol Biol. 1993;20:465-96.
Prodromou, et al. Recursive PCR: a novel technique for total gene synthesis. Protein Eng. Dec. 1992;5(8):827-9.
Quan, et al. Parallel on-chip gene synthesis and application to optimization of protein expression. Nature Biotechnology. 2011; 29:449-452.
RF Electric discharge type excimer lamp. Products Catalog. Excimer lamp light source "flat excimer," 16 pages dated Jan. 2016. From: http://www.hamamatsu.com/jp/en/product/category/1001/3026/index.html.
Richmond, et al. Amplification and assembly of chip-eluted DNA (AACED): a method for high-throughput gene synthesis. Nucleic Acids Res. Sep. 24, 2004;32(17):5011-8. Print 2004.
Roche. Restriction Enzymes from Roche Applied Science—A Tradition of Premium Quality and Scientific Support. FAQS and Ordering Guide. Roche Applied Science. Accessed Jan. 12, 2015, 37 pages.

(56) References Cited

OTHER PUBLICATIONS

Ruminy, et al., "Long-range identification of hepatocyte nuclear factor-3 (FoxA) high and low-affinity binding Sites with a chimeric nuclease", J. Mol. Bioi., vol. 310, 523-535 (2001).
Saboulard, et al. High-throughput site-directed mutagenesis using oligonucleotides synthesized on DNA chips. Biotechniques. Sep. 2005;39(3):363-8.
Sacconi, L. et al., Three-dimensional magneto-optic trap for micro-object manipulation, Optics Letters, vol. 26, No. 17, 1359-1361 (Sep. 1, 2001).
Saiki et al. Analysis of enzymatically amplified beta-globin and HLA-DQ alpha DNA with allele-specific oligonucleotide probes Nature 324:163-166 (1986).
Sandhu, et al. Dual asymmetric PCR: one-step construction of synthetic genes. Biotechniques. Jan. 1992;12(1):14-6.
Schaller, et al. Studies on Polynucleotides. XXV.1 The Stepwise Synthesis of Specific Deoxyribopolynucleotides (5). Further Studies on the Synthesis of Internucleotide Bond by the Carbodiimide Method. The Synthesis of Suitably Protected Dinucleotides as Intermediates in the Synthesis of Higher Oligonucleotides. J. Am. Chem. Soc. 1963; 85(23):3828-3835.
Schmalzing, Dieter et al., "Microchip electrophoresis: a method for high-speed SNP detection", Nucleic Acids Research, vol. 28, No. 9, i-vi (2000).
Smith, et al. Generating a synthetic genome by whole genome assembly: phiX174 bacteriophage from synthetic oligonucleotides. Proc Natl Acad Sci U S A. Dec. 23, 2003;100(26):15440-5. Epub Dec. 2, 2003.
Smith, et al. Generation of cohesive ends on PCR products by UDG-mediated excision of dU, and application for cloning into restriction digest-linearized vectors. PCR Methods Appl. May 1993;2(4):328-32.
Smith, Jane et al., "Mutation detection with MutH, MutL, and MutS mismatch repair proteins", Proc. Natl. Acad. Sci. USA, vol. 93, 4374-4379 (Apr. 1996).
Smith Jane et al., "Removal of Polymerase-Produced mutant sequences from PCR products", Proc. Natl. Acad. Sci. USA, vol. 94, 6847-6850 (Jun. 1997).
Smith, Steven B. et al., "Direct mechanical measurements of the elasticity of single DNA molecules using magnetic beads", Science, vol. 258, 1122-1126 (Nov. 13, 1992).
Soni, et al. Progress toward ultrafast DNA sequencing using solid-state nanopores. Clin Chem. Nov. 2007;53(11):1996-2001. Epub Sep. 21, 2007.
Southern, et al. Analyzing and comparing nucleic acid sequences by hybridization to arrays of oligonucleotides: evaluation using experimental models. Genomics. Aug. 1992;13(4):1008-17.
Sproat, et al. An efficient method for the isolation and purification of oligoribonucleotides. Nucleosides & Nucleotides. 1995; 14(1 &2):255-273.
Steel, The Flow-Thru Chip A Three-dimensional biochip platform. In: Schena, Microarray Biochip Technology, Chapter 5, Natick, MA: Eaton Publishing, 2000, 33 pages.
Stemmer, et al. Single-step assembly of a gene and entire plasmid from large numbers of oligodeoxyribonucleotides. Gene. Oct. 16, 1995;164(1):49-53.
Stryer. "DNA Probes and genes can be synthesized by automated solid-phase methods." Biochemistry, 3rd edition, New York: W.H. Freeman and Company, 1988; 123-125.
Stutz, et al. Novel fluoride-labile nucleobase-protecting groups for the synthesis of 3'(2')-O-amino-acylated RNA sequences. Helv. Chim. Acta. 2000; 83(9):2477-2503.
Takahashi, Cell-free cloning using multiply-primed rolling circle amplification with modified RNA primers. Biotechniques. Jul. 2009;47(1):609-15. doi: 10.2144/000113155.
Tanase, M. et al., "Magnetic trapping of multicomponent nanowires", The Johns Hopkins University, Baltimore, Maryland, p. 1-3 (Jun. 25, 2001).
Tian, et al. Accurate multiplex gene synthesis from programmable DNA microchips. Nature. Dec. 23, 2004;432(7020):1050-4.

Tsai et al., Dimeric CRISPR RNA-guided Fokl nucleases for highly specific genome editing Nat. Biotechnol., 32(6):569-576, 2014.
Unger, et al. Monolithic microfabricated valves and pumps by multilayer soft lithography. Science. Apr. 7, 2000;288(5463):113-6.
U.S. Appl. No. 14/452,429 Office Action mailed Apr. 9, 2015.
U.S. Appl. No. 14/452,429 Restriction Requirement mailed Dec. 12, 2014.
U.S. Appl. No. 14/452,429 Office Action mailed Oct. 21, 2015.
U.S. Appl. No. 14/885,962 Restriction Requirment mailed Mar. 1, 2016.
U.S. Appl. No. 14/885,965 Office Action mailed Feb. 18, 2016.
Vaijayanthi, et al. Recent advances in oligonucleotide synthesis and their applications. Indian J Biochem Biophys. Dec. 2003;40(6):377-91.
Van Den Brulle, et al. A novel solid phase technology for high-throughput gene synthesis. Biotechniques. 2008; 45(3):340-343.
Vargeese, et al. Efficient activation of nucleoside phosphoramidites with 4,5-dicyanoimidazole during oligonucleotide synthesis. Nucleic Acids Res. Feb. 15, 1998;26(4):1046-50.
Verma, et al. Modified oligonucleotides: synthesis and strategy for users. Annu Rev Biochem. 1998;67:99-134.
Vincent, et al. Helicase-dependent isothermal DNA amplification. EMBO Rep. Aug. 2004;5(8):795-800.
Visscher et al., "Construction of multiple-beam optical traps with nanometer-resolution position sensing", IEEE Journal of Selected Topics in Quantum Electronics, vol. 2, No. 4, 1066-1076 (Dec. 1996).
Voldmans Joel et al., "Holding forces of single-particle dielectrophoretic traps." Biophysical Journal, vol. 80, No. 1, 531-541 (Jan. 2001).
Vos, et al. AFLP: A new technique for DNA fingerprinting. Nucleic Acids Res. Nov. 11, 1995;23(21):4407-14.
Wah, David A. et al., "Structure of Fok I has implications for DNA cleavage", Proc. Natl. Acad. Sci. USA, vol. 95, 10564-10569 (Sep. 1998).
Wah, David A. et al., "Structure of the multimodular endonuclease Fok I bound to DNA", Nature, vol. 388, 97-100 ( Jul. 1997).
Walker, et al. Strand displacement amplification—an isothermal, in vitro DNA amplification technique. Nucleic Acids Res. Apr. 11, 1992;20(7):1691-6.
Weber, et al. A modular cloning system for standardized assembly of multigene constructs. PLoS One. Feb. 18, 2011;6(2):e16765. doi: 10.1371/journal.pone.0016765.
Welz, et al. 5-(Benzylmercapto)-1H-tetrazole as activator for 2'-O-TBDMS phosphoramidite building blocks in RNA synthesis. Tetrahedron Lett. 2002; 43(5):795-797.
Westin et al., Anchored multiplex amplification on a microelectronic chip array Nature Biotechnology, 18:199-202 (2000) (abstract only).
Whitehouse, Adrian et al. "Analysis of the mismatch and insertion/deletion binding properties of Thermus thermophilus, HB8, MutS", Biochemical and Biophysical Research Communications, vol. 233, 834-837 (1997).
Wirtz, Denis, "Direct measurement of the transport properties of a single DNA molecule", Physical Review Letters, vol. 75, No. 12, 2436-2439 (Sep. 18, 1995).
Withers-Martinez, Chrislaine et al., "PCR-based gene synthesis as an efficient approach for expression of the A+ T-rich malaria genome", Protein Engineering, vol. 12, No. 12, 1113-1120 (1999).
Wood, Richard D. et al., "Human DNA repair genes", Science, vol. 291, 1284-1289 (Feb. 16, 2001).
Wosnick, et al. Rapid construction of large synthetic genes: total chemical synthesis of two different versions of the bovine prochymosin gene. Gene. 1987;60(1):115-27.
Wu, et al. RNA-mediated gene assembly from DNA arrays. Angew Chem Int Ed Engl. May 7, 2012;51(19):4628-32. doi: 10.1002/anie. 201109058.
Wu, et al. Specificity of the nick-closing activity of bacteriophage T4 DNA ligase. Gene. 1989;76(2):245-54.
Wu, Xing-Zheng et al., "An improvement of the on-line electrophoretic concentration method for capillary electrophoresis of proteins an experimental factors affecting he concentration effect", Analytical Sciences, vol. 16, 329-331 (Mar. 2000).

(56) References Cited

OTHER PUBLICATIONS

Xiong, et al. A simple, rapid, high-fidelity and cost-effective PCR-based two-step DNA synthesis method for long gene sequences. Nucleic Acids Res. Jul. 7, 2004;32(12):e98.

Xiong, et al. Non-polymerase-cycling-assembly-based chemical gene synthesis: Strategies, methods, and progress. Biotechnology Advances. 2008; 26(2):121-134.

Yang, et al "Purification, cloning, and characterization of the CEL I nuclease", Biochemistry, vol. 39, No. 13, 3533-351 (2000).

Yehezkel et al., De novo DNA synthesis using single molecule PCR Nucleic Acids Research, 36(17):e107, 2008.

Youil, Rima et al., "Detection of 81 of 81 known mouse Beta-Giobin promoter mutations with T4 Endonuclease VII• The EMC Method", Genomics, vol. 32, 431-435 (1996).

Young, et al. Two-step total gene synthesis method. Nucleic Acids Res. Apr. 15, 2004;32(7):e59.

Zheleznaya, et al. Nicking endonucleases. Biochemistry (Mosc). Dec. 2009;74(13):1457-66.

Zhou et al., Microfluidic PicoArray synthesis of oligodeoxynucleotides and simultaneous assembling of multiple DNA sequences Nucleic Acids Research, 32(18):5409-5417, 2004.

Church et al., Next-generation digital information storage in DNA. Science, 337:6102, 1628-1629, 2012.

PCT Patent Application No. PCT/US2016/052916 International Search Report and Written Opinion dated Dec. 30, 2016.

U.S. Appl. No. 14/885,962 Office Action dated Dec. 16, 2016.

U.S. Appl. No. 15/187,721 Notice of Allowance dated Dec. 7, 2016.

U.S. Appl. No. 15/187,721 Office Action dated Oct. 14, 2016.

\* cited by examiner

SEQUENCE LISTING

```
<160> NUMBER OF SEQ ID NOS: 83

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(11)
<223> OTHER INFORMATION: a, c, t, g, unknown or other
<220> FEATURE:
<221> NAME/KEY: misc_feature
<222> LOCATION: (2)..(11)
<223> OTHER INFORMATION: This region may encompass 1-10 nucleotides

<400> SEQUENCE: 1
annnnnnnnn nt                                                          12

<210> SEQ ID NO 2
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(5)
<223> OTHER INFORMATION: a, c, t, g, unknown or other

<400> SEQUENCE: 2 annnnt                                                                  6

<210> SEQ ID NO 3
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
``` aagtct                                                                          6

<210> SEQ ID NO 4
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4 aagtcu                                                                          6

<210> SEQ ID NO 5
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 5 agactu                                                                          6

<210> SEQ ID NO 6
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6 agactt                                                                          6

<210> SEQ ID NO 7
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 7 aatgcu                                                                          6

<210> SEQ ID NO 8
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 8 agcatu                                                                          6

```
<210> SEQ ID NO 9
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9 aatgct                                                                    6

<210> SEQ ID NO 10
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10 agcatt                                                                    6

<210> SEQ ID NO 11
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(5)
<223> OTHER INFORMATION: a, c, t, u, g, unknown or other

<400> SEQUENCE: 11 annnnu                                                                    6

<210> SEQ ID NO 12
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(5)
<223> OTHER INFORMATION: a, c, t, u, g, unknown or other

<400> SEQUENCE: 12 gnnnnu                                                                    6

<210> SEQ ID NO 13
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
```

-continued

<221> NAME/KEY: modified_base
<222> LOCATION: (2)..(11)
<223> OTHER INFORMATION: a, c, t, u, g, unknown or other
<220> FEATURE:
<221> NAME/KEY: misc_feature
<222> LOCATION: (2)..(11)
<223> OTHER INFORMATION: This region may encompass 1-10 nucleotides

<400> SEQUENCE: 13
annnnnnnnn nu                                                    12

<210> SEQ ID NO 14
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(11)
<223> OTHER INFORMATION: a, c, t, u, g, unknown or other
<220> FEATURE:
<221> NAME/KEY: misc_feature
<222> LOCATION: (2)..(11)
<223> OTHER INFORMATION: This region may encompass 1-10 nucleotides

<400> SEQUENCE: 14
annnnnnnnn nu                                                    12

<210> SEQ ID NO 15
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(11)
<223> OTHER INFORMATION: a, c, t, u, g, unknown or other
<220> FEATURE:
<221> NAME/KEY: misc_feature
<222> LOCATION: (2)..(11)
<223> OTHER INFORMATION: This region may encompass 1-10 nucleotides

<400> SEQUENCE: 15
annnnnnnnn nu                                                    12

<210> SEQ ID NO 16
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(11)
<223> OTHER INFORMATION: a, c, t, g, unknown or other
<220> FEATURE:
<221> NAME/KEY: misc_feature
<222> LOCATION: (2)..(11)
<223> OTHER INFORMATION: This region may encompass 1-10 nucleotides

<400> SEQUENCE: 16
gnnnnnnnnn nc                                                                  12

<210> SEQ ID NO 17
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(5)
<223> OTHER INFORMATION: a, c, t, g, unknown or other

<400> SEQUENCE: 17 gnnnnc                                                                          6

<210> SEQ ID NO 18
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(11)
<223> OTHER INFORMATION: a, c, t, u, g, unknown or other
<220> FEATURE:
<221> NAME/KEY: misc_feature
<222> LOCATION: (2)..(11)
<223> OTHER INFORMATION: This region may encompass 1-10 nucleotides

<400> SEQUENCE: 18
annnnnnnnn nu                                                                  12

<210> SEQ ID NO 19
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(11)
<223> OTHER INFORMATION: a, c, t, u, g, unknown or other
<220> FEATURE:
<221> NAME/KEY: misc_feature
<222> LOCATION: (2)..(11)
<223> OTHER INFORMATION: This region may encompass 1-10 nucleotides

<400> SEQUENCE: 19
annnnnnnnn nu                                                                  12

<210> SEQ ID NO 20
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:

```
<221> NAME/KEY: modified_base
<222> LOCATION: (2)..(11)
<223> OTHER INFORMATION: a, c, t, u, g, unknown or other
<220> FEATURE:
<221> NAME/KEY: misc_feature
<222> LOCATION: (2)..(11)
<223> OTHER INFORMATION: This region may encompass 1-10 nucleotides

<400> SEQUENCE: 20
annnnnnnnn nu                                                              12

<210> SEQ ID NO 21
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(11)
<223> OTHER INFORMATION: a, c, t, u, g, unknown or other
<220> FEATURE:
<221> NAME/KEY: misc_feature
<222> LOCATION: (2)..(11)
<223> OTHER INFORMATION: This region may encompass 1-10 nucleotides

<400> SEQUENCE: 21
annnnnnnnn nu                                                              12

<210> SEQ ID NO 22
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22 cctcagc                                                                     7

<210> SEQ ID NO 23
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23 gaattc                                                                      6

<210> SEQ ID NO 24
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, c, t, g, unknown or other

<400> SEQUENCE: 24
gccnnnnngg c                                                               11
```

```
<210> SEQ ID NO 25
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25 cctcagc                                                                    7

<210> SEQ ID NO 26
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26 ctgaag                                                                     6

<210> SEQ ID NO 27
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, c, t, g, unknown or other

<400> SEQUENCE: 27
cgannnnnnt gc                                                              12

<210> SEQ ID NO 28
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28 cctcagc                                                                    7

<210> SEQ ID NO 29
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29 gctgagg                                                                    7

<210> SEQ ID NO 30
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

-continued

```
<222> LOCATION: (7)..(7)
<223> OTHER INFORMATION: a, c, t, g, unknown or other

<400> SEQUENCE: 30 gaatgcn                                                                    7

<210> SEQ ID NO 31
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other

<400> SEQUENCE: 31 ngcattc                                                                    7

<210> SEQ ID NO 32
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: a, c, t, g, unknown or other

<400> SEQUENCE: 32 gcaatgnn                                                                   8

<210> SEQ ID NO 33
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, t, g, unknown or other

<400> SEQUENCE: 33 nncattgc                                                                   8

<210> SEQ ID NO 34
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: a, c, t, g, unknown or other

<400> SEQUENCE: 34 gcagtgnn                                                                   8

<210> SEQ ID NO 35
<211> LENGTH: 8
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, t, g, unknown or other

<400> SEQUENCE: 35 nncactgc                                                                    8

<210> SEQ ID NO 36
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(10)
<223> OTHER INFORMATION: a, c, t, g, unknown or other

<400> SEQUENCE: 36 ggatcnnnnn                                                                 10

<210> SEQ ID NO 37
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(5)
<223> OTHER INFORMATION: a, c, t, g, unknown or other

<400> SEQUENCE: 37 nnnnngatcc                                                                 10

<210> SEQ ID NO 38
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38 cctcagc                                                                     7

<210> SEQ ID NO 39
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39 gctgagg                                                                     7

<210> SEQ ID NO 40
<211> LENGTH: 7
<212> TYPE: DNA
<213> ORGANISM: Artificial Sequence
<220> FEATURE:
```

-continued

```
<223> OTHER INFORMATION: Description of Artificial Sequence: Synthetic
      oligonucleotide
<220> FEATURE:
<221> NAME/KEY: modified_base
<222> LOCATION: (6)..(7)
<223> OTHER INFORMATION: a, c, t, g, unknown or other

<400> SEQUENCE: 40 gtctcnn                                                                 7

<210> SEQ ID NO 41
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, t, g, unknown or other

<400> SEQUENCE: 41 nngagac                                                                 7

<210> SEQ ID NO 42
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: a, c, t, g, unknown or other

<400> SEQUENCE: 42 gctcttcn                                                                8

<210> SEQ ID NO 43
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other

<400> SEQUENCE: 43 ngaagagc                                                                8

<210> SEQ ID NO 44
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(10)
<223> OTHER INFORMATION: a, c, t, g, unknown or other

<400> SEQUENCE: 44 gagtcnnnnn                                                             10
```

<210> SEQ ID NO 45
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(5)
<223> OTHER INFORMATION: a, c, t, g, unknown or other

<400> SEQUENCE: 45 nnnnngactc                                                          10

<210> SEQ ID NO 46
<211> LENGTH: 3
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46 ccd                                                                  3

<210> SEQ ID NO 47
<211> LENGTH: 3
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47 hgg                                                                  3

<210> SEQ ID NO 48
<211> LENGTH: 1042
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
cagcagttcc tcgctcttct cacgacgagt tcgacatcaa caagctgcgc taccacaaga     60
tcgtgctgat ggccgacgcc gatgttgacg ccagcacat cgcaacgctg ctgctcaccc    120
tgcttttccg cttcatgcca gacctcgtcg ccgaaggcca cgtctacttg gcacagccac    180
ctttgtacaa actgaagtgg cagcgcggag agccaggatt cgcatactcc gatgaggagc    240
gcgatgagca gctcaacgaa ggccttgccg ctggacgcaa gatcaacaag gacgacggca    300
tccagcgcta cagggtctc ggcgagatga cgccagcga gctgtgggaa accaccatgg     360
acccaactgt tcgtattctg cgccgcgtgg acatcaccga tgctcagcgt gctgatgaac    420
tgttctccat cttgatgggt gacgacgttg tggctcgccg cagcttcatc acccgaaatg    480
ccaaggatgt tcgtttcctc gatatctaaa gcgccttact taacccgccc ctggaattct    540
gggggcgggt tttgtgattt ttagggtcag cactttataa atgcaggctt ctatggcttc    600
aagttggcca atacgtgggg ttgatttttt aaaaccagac tggcgtgccc aagagctgaa    660 cttttcgctag tcatgggcat tcctggccgg tttcttggcc ttcaaaccgg acaggaatgc    720
ccaagttaac ggaaaaaccg aaagaggggc acgccagtct ggttctccca aactcaggac    780

```
aaatcctgcc tcggcgcctg cgaaaagtgc cctctcctaa atcgtttcta agggctcgtc    840
agaccccagt tgatacaaac atacattctg aaaattcagt cgcttaaatg ggcgcagcgg    900
gaaatgctga aaactacatt aatcaccgat accctagggc acgtgacctc tactgaaccc    960
accaccacag cccatgttcc actacctgat ggatcttcca ctccagtcca aatttgggcg    1020
tacactgcga gtccactacg at                                             1042
```

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (8)..(8)
<223> OTHER INFORMATION: ideoxy-U

<400> SEQUENCE: 49

```
cagcagtucc tcgctcttct                                                20
```

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (8)..(8)
<223> OTHER INFORMATION: ideoxy-U

<400> SEQUENCE: 50

```
atcgtagugg actcgcagtg ta                                             22
```

<210> SEQ ID NO 51
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-Phos

<400> SEQUENCE: 51

```
tacgctcttc ctcagcagtg gtcatcgtag t                                   31
```

<210> SEQ ID NO 52
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(7)
<223> OTHER INFORMATION: Phosphorothioate linkage

<400> SEQUENCE: 52
accactgctg aggaagagcg tacagcagtt                                              30

<210> SEQ ID NO 53
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(5)
<223> OTHER INFORMATION: a, c, u, g, unknown or other

<400> SEQUENCE: 53 annnnu                                                                         6

<210> SEQ ID NO 54
<211> LENGTH: 34
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (18)..(18)
<223> OTHER INFORMATION: ideoxy-U

<400> SEQUENCE: 54
tgatcggcaa tgatatguct ggaaagaaca tgtg                                          34

<210> SEQ ID NO 55
<211> LENGTH: 38
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (18)..(18)
<223> OTHER INFORMATION: ideoxy-U

<400> SEQUENCE: 55
tgatcggcaa tgatggcuta taatgcgaca aacaacag                                      38

<210> SEQ ID NO 56
<211> LENGTH: 34
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (18)..(18)
<223> OTHER INFORMATION: ideoxy-U

<400> SEQUENCE: 56
tgatcggcaa tgatatgucg ctggaaagaa catg                               34

<210> SEQ ID NO 57
<211> LENGTH: 38
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (18)..(18)
<223> OTHER INFORMATION: ideoxy-U

<400> SEQUENCE: 57
tgatcggcaa tgatggcucg tataatgcga caaacaac                           38

<210> SEQ ID NO 58
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58 tgatcg                                                              6

<210> SEQ ID NO 59
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59 gcaatg                                                              6

<210> SEQ ID NO 60
<211> LENGTH: 3087
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
agccatatga ccatgattac ggattcactg gccgtcgttt tacaacgtcg tgactgggaa    60
aaccctggcg ttacccaact taatcgcctt gcagcacatc cccctttcgc cagctggcgt   120
aatagcgaag aggcccgcac cgatcgccct tcccaacagt tgcgcagcct gaatggcgaa   180
tggcgctttg cctggtttcc ggcaccagaa gcggtgccgg aaagctggct ggagtgcgat   240
cttcctgagg ccgatactgt cgtcgtcccc tcaaactggc agatgcacgg ttacgatgcg   300
cccatctaca ccaacgtgac ctatcccatt acggtcaatc cgccgtttgt tcccacggag   360
aatccgacgg gttgttactc gctcacattt aatgttgatg aaagctggct acaggaaggc   420
cagacgcgaa ttatttttga tggcgttaac tcggcgtttc atctgtggtg caacgggcgc   480
tgggtcggtt acggccagga cagtcgtttg ccgtctgaat ttgacctgag cgcatttttta   540 cgcgccggag aaaaccgcct cgcggtgatg gtgctgcgct ggagtgacgg cagttatctg   600

```
gaagatcagg atatgtggcg gatgagcggc attttccgtg acgtctcgtt gctgcataaa    660
ccgactacac aaatcagcga tttccatgtt gccactcgct ttaatgatga tttcagccgc    720
gctgtactgg aggctgaagt tcagatgtgc ggcgagttgc gtgactacct acgggtaaca    780
gtttctttat ggcagggtga aacgcaggtc gccagcggca ccgcgccttt cggcggtgaa    840
attatcgatg agcgtggtgg ttatgccgat cgcgtcacac tacgtctgaa cgtcgaaaac    900
ccgaaactgt ggagcgccga aatcccgaat ctctatcgtg cggtggttga actgcacacc    960
gccgacggca cgctgattga agcagaagcc tgcgatgtcg gtttccgcga ggtgcggatt   1020
gaaaatggtc tgctgctgct gaacggcaag ccgttgctga ttcgaggcgt taaccgtcac   1080
gagcatcatc ctctgcatgg tcaggtcatg gatgagcaga cgatggtgca ggatatcctg   1140
ctgatgaagc agaacaactt taacgccgtg cgctgttcgc attatccgaa ccatccgctg   1200
tggtacacgc tgtgcgaccg ctacggcctg tatgtggtgg atgaagccaa tattgaaacc   1260
cacggcatgg tgccaatgaa tcgtctgacc gatgatccgc gctggctacc ggcgatgagc   1320
gaacgcgtaa cgcgaatggt gcagcgcgat cgtaatcacc cgagtgtgat catctggtcg   1380
ctggggaatg aatcaggcca cggcgctaat cacgacgcgc tgtatcgctg gatcaaatct   1440
gtcgatcctt cccgcccggt gcagtatgaa ggcggcggag ccgacaccac ggccaccgat   1500
attatttgcc cgatgtacgc gcgcgtggat gaagaccagc ccttcccggc tgtgccgaaa   1560
tggtccatca aaaatggct ttcgctacct ggagagacgc gcccgctgat cctttgcgaa    1620
tacgcccacg cgatgggtaa cagtcttggc ggtttcgcta atactggca ggcgtttcgt    1680
cagtatcccc gtttacaggg cggcttcgtc tgggactggg tggatcagtc gctgattaaa   1740
tatgatgaaa acggcaaccc gtggtcggct tacggcggtg attttggcga tacgccgaac   1800
gatcgccagt tctgtatgaa cggtctggtc tttgccgacc gcacgccgca tccagcgctg   1860
acggaagcaa acaccagca gcagtttttc cagttccgtt tatccgggca aaccatcgaa   1920
gtgaccagcg aatacctgtt ccgtcatagc gataacgagc tcctgcactg gatggtggcg   1980
ctggatggta agccgctggc aagcggtgaa gtgcctctgg atgtcgctcc acaaggtaaa   2040
cagttgattg aactgcctga actaccgcag ccggagagcg ccgggcaact ctggctcaca   2100
gtacgcgtag tgcaaccgaa cgcgaccgca tggtcagaag ccgggcacat cagcgcctgg   2160
cagcagtggc gtctggcgga aaacctcagt gtgacgctcc ccgccgcgtc ccacgccatc   2220
ccgcatctga ccaccagcga aatggatttt tgcatcgagc tgggtaataa gcgttggcaa   2280
tttaaccgcc agtcaggctt tctttcacag atgtggattg cgataaaaa acaactgctg    2340
acgccgctgc gcgatcagtt cacccgtgca ccgctggata cgacattgg cgtaagtgaa    2400
gcgacccgca ttgaccctaa cgcctgggtc gaacgctgga aggcggcggg ccattaccag   2460
gccgaagcag cgttgttgca gtgcacggca gatacacttg ctgatgcggt gctgattacg   2520
accgctcacg cgtggcagca tcaggggaaa accttattta tcagccggaa aacctaccgg   2580
attgatggta gtggtcaaat ggcgattacc gttgatgttg aagtggcgag cgatacaccg   2640
catccggcgc ggattggcct gaactgccag ctggcgcagg tagcagagcg ggtaaactgg   2700
ctcggattag ggccgcaaga aaactatccc gaccgcctta ctgccgcctg ttttgaccgc   2760
tgggatctgc cattgtcaga catgtatacc ccgtacgtct tcccgagcga aaacggtctg   2820
cgctgcggga cgcgcgaatt gaattatggc ccacaccagt ggcgcggcga cttccagttc   2880
aacatcagcc gctacagtca acagcaactg atggaaacca gccatcgcca tctgctgcac   2940
gcggaagaag gcacatggct gaatatcgac ggtttccata tggggattgg tggcgacgac   3000
```

```
tcctggagcc cgtcagtatc ggcggaattc cagctgagcg ccggtcgcta ccattaccag    3060
ttggtctggt gtcaaaaata aatatgt                                        3087

<210> SEQ ID NO 61
<211> LENGTH: 1017
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
atgaccatga ttacggattc actggccgtc gttttacaac gtcgtgactg ggaaaaccct     60
ggcgttaccc aacttaatcg ccttgcagca catcccccTT tcgccagctg gcgtaatagc    120
gaagaggccc gcaccgatcg cccttcccaa cagttgcgca gcctgaatgg cgaatggcgc    180
tttgcctggt ttccggcacc agaagcggtg ccggaaagct ggctggagtg cgatcttcct    240
gaggccgata ctgtcgtcgt cccctcaaac tggcagatgc acggttacga tcgcgccatc    300
tacaccaacg tgacctatcc cattacggtc aatccgccgt tgttcccac ggagaatccg     360 acgggttgtt actcgctcac atttaatgtt gatgaaagct ggctacagga aggccagacg    420
cgaattattt ttgatggcgt taactcggcg tttcatctgt ggtgcaacgg cgctgggtc     480 ggttacggcc aggacagtcg tttgccgtct gaatttgacc tgagcgcatt tttacgcgcc    540
ggagaaaacc gcctcgcggt gatggtgctg cgctggagtg acggcagtta tctggaagat    600
caggatatgt ggcggatgag cggcattttc cgtgacgtct cgttgctgca taaaccgact    660
acacaaatca gcgatttcca tgttgccact cgctttaatg atgatttcag ccgcgctgta    720
ctggaggctg aagttcagat gtgcggcgag ttgcgtgact acctacgggt aacagtttct    780
ttatggcagg gtgaaacgca ggtcgccagc ggcaccgcgc ctttcggcgg tgaaattatc    840
gatgagcgtg tggttatgc cgatcgcgtc acactacgtc tgaacgtcga aaacccgaaa     900
ctgtggagcg ccgaaatccc gaatctctat cgtgcggtgg ttgaactgca caccgccgac    960
ggcacgctga ttgaagcaga agcctgcgat gtcggttTcc gcgaggtgcg gattgaa     1017

<210> SEQ ID NO 62
<211> LENGTH: 1010
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
ctgctgctgc tgaacggcaa gccgttgctg attcgaggcg ttaaccgtca cgagcatcat     60
cctctgcatg gtcaggtcat ggatgagcag acgatggtgc aggatatcct gctgatgaag    120
cagaacaact taacgccgt cgctgttcg cattatccga accatccgct gtggtacacg      180
ctgtgcgacc gctacggcct gtatgtggtg atgaagcca atattgaaac ccacggcatg     240
gtgccaatga atcgtctgac cgatgatccg cgctggctac cggcgatgag cgaacgcgta    300
acgcgaatgt gcagcgcga tcgtaatcac ccgagtgtga tcatctggtc gctggggaat    360
gaatcaggcc acggcgctaa tcacgacgcg ctgtatcgct ggatcaaatc tgtcgatcct    420
tcccgcccgg tgcagtatga aggcggcgga gccgacacca cggccaccga tattatttgc    480
ccgatgtacg cgcgcgtgga tgaagaccag cccttcccgg ctgtgccgaa atggtccatc    540
```

-continued

| | | |
|---|---|---|
| aaaaaatggc tttcgctacc tggagagacg cgcccgctga tcctttgcga atacgcccac | 600 | |
| gcgatgggta acagtcttgg cggtttcgct aaatactggc aggcgtttcg tcagtatccc | 660 | |
| cgtttacagg gcggcttcgt ctgggactgg gtggatcagt cgctgattaa atatgatgaa | 720 | |
| aacggcaacc cgtggtcggc ttacggcggt gattttggcg atacgccgaa cgatcgccag | 780 | |
| ttctgtatga acggtctggt cttttgccgac cgcacgccgc atccagcgct gacggaagca | 840 | |
| aaacaccagc agcagttttt ccagttccgt ttatccgggc aaaccatcga agtgaccagc | 900 | |
| gaatacctgt tccgtcatag cgataacgag ctcctgcact ggatggtggc gctggatggt | 960 | |
| aagccgctgg caagcggtga agtgcctctg gatgtcgctc cacaaggtaa | 1010 | |

<210> SEQ ID NO 63
<211> LENGTH: 1036
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63

| | | |
|---|---|---|
| gattgaactg cctgaactac cgcagccgga gagcgccggg caactctggc tcacagtacg | 60 | |
| cgtagtgcaa ccgaacgcga ccgcatggtc agaagccggg cacatcagcg cctggcagca | 120 | |
| gtggcgtctg gcgaaaaacc tcagtgtgac gctccccgcc gcgtcccacg ccatcccgca | 180 | |
| tctgaccacc agcgaaatgg atttttgcat cgagctgggt aataagcgtt ggcaatttaa | 240 | |
| ccgccagtca ggctttcttt cacagatgtg gattggcgat aaaaaacaac tgctgacgcc | 300 | |
| gctgcgcgat cagttcaccc gtgcaccgct ggataacgac attggcgtaa gtgaagcgac | 360 | |
| ccgcattgac cctaacgcct gggtcgaacg ctggaaggcg gcgggccatt accaggccga | 420 | |
| agcagcgttg ttgcagtgca cggcagatac acttgctgat gcggtgctga ttacgaccgc | 480 | |
| tcacgcgtgg cagcatcagg ggaaaaacctt atttatcagc cggaaaacct accggattga | 540 | |
| tggtagtggt caaatggcga ttaccgttga tgttgaagtg gcgagcgata caccgcatcc | 600 | |
| ggcgcggatt ggcctgaact gccagctggc gcaggtagca gagcgggtaa actggctcgg | 660 | |
| attagggccg caagaaaact atcccgaccg ccttactgcc gcctgttttg accgctggga | 720 | |
| tctgccattg tcagacatgt ataccccgta cgtcttcccg agcgaaaacg gtctgcgctg | 780 | |
| cgggacgcgc gaattgaatt atggcccaca ccagtggcgc ggcgacttcc agttcaacat | 840 | |
| cagccgctac agtcaacagc aactgatgga aaccagccat cgccatctgc tgcacgcgga | 900 | |
| agaaggcaca tggctgaata tcgacggttt ccatatgggg attggtggcg acgactcctg | 960 | |
| gagcccgtca gtatcggcgg aattccagct gagcgccggt cgctaccatt accagttggt | 1020 | |
| ctggtgtcaa aaataa | 1036 | |

<210> SEQ ID NO 64
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64

| | | |
|---|---|---|
| aatggt | 6 | |

<210> SEQ ID NO 65
<211> LENGTH: 6

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65 acagtt                                                                      6

<210> SEQ ID NO 66
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66 agccat                                                                      6

<210> SEQ ID NO 67
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67 ttatgt                                                                      6

<210> SEQ ID NO 68
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
gtatgctgac tgct                                                            14

<210> SEQ ID NO 69
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
ttgccctacg gtct                                                            14

<210> SEQ ID NO 70
<211> LENGTH: 1081
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
ggacttgtat gctgactgct gcaatgagcc atatgaccat gattacggat tcactggccg         60
tcgttttaca acgtcgtgac tgggaaaacc ctggcgttac ccaacttaat cgccttgcag        120
cacatccccc tttcgccagc tggcgtaata gcgaagaggc ccgcaccgat cgcccttccc        180
```

```
aacagttgcg cagcctgaat ggcgaatggc gctttgcctg gtttccggca ccagaagcgg      240
tgccggaaag ctggctggag tgcgatcttc ctgaggccga tactgtcgtc gtccctcaa      300 actggcagat gcacggttac gatgcgccca tctacaccaa cgtgacctat cccattacgg      360
tcaatccgcc gtttgttccc acggagaatc cgacgggttg ttactcgctc acatttaatg      420
ttgatgaaag ctggctacag gaaggccaga cgcgaattat ttttgatggc gttaactcgg      480
cgtttcatct gtggtgcaac gggcgctggg tcggttacgg ccaggacagt cgtttgccgt      540
ctgaatttga cctgagcgca tttttacgcg ccggagaaaa ccgcctcgcg gtgatggtgc      600
tgcgctggag tgacggcagt tatctggaag atcaggatat gtggcggatg agcggcattt      660
tccgtgacgt ctcgttgctg cataaaccga ctacacaaat cagcgatttc catgttgcca      720
ctcgctttaa tgatgatttc agccgcgctg tactggaggc tgaagttcag atgtgcggcg      780
agttgcgtga ctacctacgg gtaacagttt ctttatggca gggtgaaacg caggtcgcca      840
gcggcaccgc gcctttcggc ggtgaaatta tcgatgagcg tggtggttat gccgatcgcg      900
tcacactacg tctgaacgtc gaaaacccga aactgtggag cgccgaaatc ccgaatctct      960
atcgtgcggt ggttgaactg cacaccgccg acggcacgct gattgaagca gaagcctgcg     1020
atgtcggttt ccgcgaggtg cggattgaaa atggtcattg cagaccgtag gcaatgatt      1080 c                                                                    1081
```

<210> SEQ ID NO 71
<211> LENGTH: 1074
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 71

```
ggacttgtat gctgactgct gcaatgaatg gtctgctgct gctgaacggc aagccgttgc       60
tgattcgagg cgttaaccgt cacgagcatc atcctctgca tggtcaggtc atggatgagc      120
agacgatggt gcaggatatc ctgctgatga agcagaacaa ctttaacgcc gtgcgctgtt      180
cgcattatcc gaaccatccg ctgtggtaca cgctgtgcga ccgctacggc ctgtatgtgg      240
tggatgaagc caatattgaa acccacggca tggtgccaat gaatcgtctg accgatgatc      300
cgcgctggct accggcgatg agcgaacgcg taacgcgaat ggtgcagcgc gatcgtaatc      360
acccgagtgt gatcatctgg tcgctgggga tgaatcagg ccacggcgct aatcacgacg      420
cgctgtatcg ctggatcaaa tctgtcgatc cttcccgccc ggtgcagtat gaaggcggcg      480
gagccgacac cacggccacc gatattattt gcccgatgta cgcgcgcgtg gatgaagacc      540
agcccttccc ggctgtgccg aaatggtcca tcaaaaaatg gctttcgcta cctggagaga      600
cgcgcccgct gatcctttgc gaatacgccc acgcgatggg taacagtctt ggcggtttcg      660
ctaaatactg gcaggcgttt cgtcagtatc ccgtttaca gggcggcttc gtctgggact      720
gggtggatca gtcgctgatt aaatatgatg aaaacggcaa cccgtggtcg gcttacggcg      780
gtgattttgg cgatacgccg aacgatcgcc agttctgtat gaacggtctg gtctttgccg      840
accgcacgcc gcatccagcg ctgacggaag caaaacacca gcagcagttt ttccagttcc      900
gtttatccgg gcaaaccatc gaagtgacca gcgaatacct gttccgtcat agcgataacg      960
agctcctgca ctgatggtg gcgctggatg gtaagccgct ggcaagcggt gaagtgcctc     1020
tggatgtcgc tccacaaggt aaacagttca ttgcagaccg tagggcaatg attc          1074
```

<210> SEQ ID NO 72
<211> LENGTH: 1100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72

| | | | | | |
|---|---|---|---|---|---|
| ggacttgtat | gctgactgct | gcaatgacag | ttgattgaac | tgcctgaact | accgcagccg | 60 |
| gagagcgccg | ggcaactctg | gctcacagta | cgcgtagtgc | aaccgaacgc | gaccgcatgg | 120 |
| tcagaagccg | ggcacatcag | cgcctggcag | cagtggcgtc | tggcggaaaa | cctcagtgtg | 180 |
| acgctccccg | ccgcgtccca | cgccatcccg | catctgacca | ccagcgaaat | ggattttgc | 240 |
| atcgagctgg | gtaataagcg | ttggcaattt | aaccgccagt | caggctttct | ttcacagatg | 300 |
| tggattggcg | ataaaaaaca | actgctgacg | ccgctgcgcg | atcagttcac | ccgtgcaccg | 360 |
| ctggataacg | acattggcgt | aagtgaagcg | acccgcattg | accctaacgc | ctgggtcgaa | 420 |
| cgctggaagg | cggcgggcca | ttaccaggcc | gaagcagcgt | tgttgcagtg | cacggcagat | 480 |
| acacttgctg | atgcggtgct | gattacgacc | gctcacgcgt | ggcagcatca | ggggaaaacc | 540 |
| ttatttatca | gccggaaaac | ctaccggatt | gatggtagtg | gtcaaatggc | gattaccgtt | 600 |
| gatgttgaag | tggcgagcga | tacaccgcat | ccggcgcgga | ttggcctgaa | ctgccagctg | 660 |
| gcgcaggtag | cagagcgggt | aaactggctc | ggattagggc | gcaagaaaa | ctatcccgac | 720 |
| cgccttactg | ccgcctgttt | tgaccgctgg | gatctgccat | tgtcagacat | gtataccccg | 780 |
| tacgtcttcc | cgagcgaaaa | cggtctgcgc | tgcgggacgc | gcgaattgaa | ttatggccca | 840 |
| caccagtggc | gcggcgactt | ccagttcaac | atcagccgct | acagtcaaca | gcaactgatg | 900 |
| gaaaccagcc | atcgccatct | gctgcacgcg | gaagaaggca | catggctgaa | tatcgacggt | 960 |
| ttccatatgg | ggattggtgg | cgacgactcc | tggagcccgt | cagtatcggc | ggaattccag | 1020 |
| ctgagcgccg | gtcgctacca | ttaccagttg | gtctggtgtc | aaaaataaat | atgtcattgc | 1080 |
| agaccgtagg | gcaatgattc | | | | | 1100 |

<210> SEQ ID NO 73
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (25)..(26)
<223> OTHER INFORMATION: Phosphorothioate linkage
<220> FEATURE:
<221> NAME/KEY: modified_base
<222> LOCATION: (26)..(26)
<223> OTHER INFORMATION: 3deoxy-U

<400> SEQUENCE: 73
gtatgctgac tgctgcaatg agccau                                         26

<210> SEQ ID NO 74
<211> LENGTH: 26
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (25)..(26)
<223> OTHER INFORMATION: Phosphorothioate linkage
<220> FEATURE:
<221> NAME/KEY: modified_base
<222> LOCATION: (26)..(26)
<223> OTHER INFORMATION: 3deoxy-U

<400> SEQUENCE: 74
ttgccctacg gtctgcaatg accatu                                              26

<210> SEQ ID NO 75
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (25)..(26)
<223> OTHER INFORMATION: Phosphorothioate linkage
<220> FEATURE:
<221> NAME/KEY: modified_base
<222> LOCATION: (26)..(26)
<223> OTHER INFORMATION: 3deoxy-U

<400> SEQUENCE: 75
gtatgctgac tgctgcaatg aatggu                                              26

<210> SEQ ID NO 76
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (25)..(26)
<223> OTHER INFORMATION: Phosphorothioate linkage
<220> FEATURE:
<221> NAME/KEY: modified_base
<222> LOCATION: (26)..(26)
<223> OTHER INFORMATION: 3deoxy-U

<400> SEQUENCE: 76
ttgccctacg gtctgcaatg aactgu                                              26

<210> SEQ ID NO 77
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
```

```
<222> LOCATION: (25)..(26)
<223> OTHER INFORMATION: Phosphorothioate linkage
<220> FEATURE:
<221> NAME/KEY: modified_base
<222> LOCATION: (26)..(26)
<223> OTHER INFORMATION: 3deoxy-U

<400> SEQUENCE: 77
gtatgctgac tgctgcaatg acagtu                                              26

<210> SEQ ID NO 78
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (25)..(26)
<223> OTHER INFORMATION: Phosphorothioate linkage
<220> FEATURE:
<221> NAME/KEY: modified_base
<222> LOCATION: (26)..(26)
<223> OTHER INFORMATION: 3deoxy-U

<400> SEQUENCE: 78
ttgccctacg gtctgcaatg acatau                                              26

<210> SEQ ID NO 79
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (56)..(61)
<223> OTHER INFORMATION: Phosphorothioate linkage

<400> SEQUENCE: 79
tacgctcttc ctcagcagtg gtcatcgtag tttgacgaca tgcgagaagg agtcgtcacc         60
a                                                                         61

<210> SEQ ID NO 80
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(11)
<223> OTHER INFORMATION: a, c, t, u, g, unknown or other
<220> FEATURE:
<221> NAME/KEY: misc_feature
<222> LOCATION: (2)..(11)
<223> OTHER INFORMATION: This region may encompass 1-10 nucleotides

<400> SEQUENCE: 80
annnnnnnnn nu                                                             12
```

```
<210> SEQ ID NO 81
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(11)
<223> OTHER INFORMATION: a, c, t, u, g, unknown or other
<220> FEATURE:
<221> NAME/KEY: misc_feature
<222> LOCATION: (2)..(11)
<223> OTHER INFORMATION: This region may encompass 1-10 nucleotides

<400> SEQUENCE: 81
gnnnnnnnnn nu                                                           12

<210> SEQ ID NO 82
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(11)
<223> OTHER INFORMATION: a, c, t, g, unknown or other
<220> FEATURE:
<221> NAME/KEY: misc_feature
<222> LOCATION: (2)..(11)
<223> OTHER INFORMATION: This region may encompass 1-10 nucleotides

<400> SEQUENCE: 82
annnnnnnnn nm                                                           12

<210> SEQ ID NO 83
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(11)
<223> OTHER INFORMATION: a, c, t, g, unknown or other
<220> FEATURE:
<221> NAME/KEY: misc_feature
<222> LOCATION: (2)..(11)
<223> OTHER INFORMATION: This region may encompass 1-10 nucleotides

<400> SEQUENCE: 83
gnnnnnnnnn nm                                                           12
```

COMPOSITIONS AND METHODS FOR SYNTHETIC GENE ASSEMBLY

CROSS-REFERENCE

This application is a Continuation of PCT/US16/16636 filed Feb. 4, 2016, which claims the benefit of U.S. Provisional Application No. 62/112,022 filed Feb. 4, 2015, both of which are herein incorporated by reference in their entirety.

SEQUENCE LISTING

The instant application contains a Sequence Listing which has been submitted electronically in ASCII format and is hereby incorporated by reference in its entirety. Said ASCII copy, created on Jan. 25, 2016 is named 44854_709_301_SL and is 41,005 bytes in size.

BACKGROUND

De novo nucleic acid synthesis is a powerful tool for basic biological research and biotechnology applications. While various methods are known for the synthesis of relatively short fragments of nucleic acids in a small scale, these techniques suffer from scalability, automation, speed, accuracy, and cost. In many cases, the assembly of nucleic acids from shorter segments is limited by the availability of non-degenerate overhangs that can be annealed to join the segments.

BRIEF SUMMARY

Provided herein are methods for nucleic acid assembly, comprising: providing a predetermined nucleic acid sequence; providing a plurality of precursor double-stranded nucleic acid fragments, each precursor double-stranded nucleic acid fragment having two strands, wherein each of the two strands comprises a sticky end sequence of 5'-A (N$^x$) T-3' (SEQ ID NO.: 1) or 5'-G (N$^x$) C-3' (SEQ ID NO.: 16), wherein N is a nucleotide, wherein x is the number of nucleotides between nucleotides A and T or between G and C, and wherein x is 1 to 10, and wherein no more than two precursor double-stranded nucleic acid fragments comprise the same sticky end sequence; providing primers comprising a nicking endonuclease recognition site and a sequence comprising (i) 5'-A (N$^x$) U-3' (SEQ ID NO.: 80) corresponding to each of the different sticky end sequences of 5'-A (N$^x$) T-3' (SEQ ID NO.: 1) or (ii) 5'-G (N$^x$) U-3' (SEQ ID NO.: 81) corresponding to each of the different sticky end sequences of 5'-G (N$^x$) C-3' (SEQ ID NO.: 16); and performing a polynucleotide extension reaction to form double-stranded nucleic acid fragments; subjecting the polynucleotide extension reaction product to nicking and cleavage reactions to form double-stranded nucleic acid fragments with 3' overhangs; and annealing the double-stranded nucleic acid fragments to form a nucleic acid encoding for the predetermined nucleic acid sequence that does not include the nicking endonuclease recognition site. Methods are further provided wherein x is 1, 2, 3, 4, 5, 6, 7, 8, 9, or 10. Methods are further provided wherein the predetermined nucleic acid sequence is 1 kb to 100 kb in length. Methods are further provided wherein the predetermined nucleic acid sequence is 1 kb to 25 kb in length. Methods are further provided wherein the predetermined nucleic acid sequence is 2 kb to 20 kb in length. Methods are further provided wherein the predetermined nucleic acid sequence is at least 2 kb in length. Methods are further provided wherein the plurality of single-stranded nucleic acid fragments are each at least 100 bases in length. Methods are further provided wherein the double-stranded nucleic acid fragments are each at least 500 bases in length. Methods are further provided wherein the double-stranded nucleic acid fragments are each at least 1 kb in length. Methods are further provided wherein the double-stranded nucleic acid fragments are each at least 20 kb in length. Methods are further provided wherein the sticky ends are at least 4 bases long. Methods are further provided wherein the sticky ends are 6 bases long. Methods are further provided wherein step c further comprises providing (i) a forward primer comprising, in order 5' to 3': a first outer adaptor region and nucleic acid sequence from a first terminal portion of predetermined nucleic acid sequence; and (ii) a reverse primer, comprising, in order 5' to 3': a second outer adaptor region and nucleic acid sequence from a second terminal portion of predetermined nucleic acid sequence. Methods are further provided wherein the annealed double-stranded nucleic acid fragments comprise the first outer adaptor region and the second outer adapter region. Methods are further provided wherein the nicking and cleavage reagents comprise a nicking endonuclease. Methods are further provided wherein the nicking endonuclease comprises endonuclease VIII. Methods are further provided wherein the nicking endonuclease is selected from the list consisting of Nb.BbvCI, Nb.BsmI, Nb.BsrDI, Nb.BtsI, Nt.AlwI, Nt.BbvCI, Nt.BsmAI, Nt.BspQI, Nt.BstNBI, and Nt.CviPII. Methods are further provided wherein the method further comprises ligating the annealed double-stranded nucleic acid fragments. Methods are further provided wherein annealing comprises thermocycling between a maximum and a minimum temperature, thereby generating a first overhang from a first double-stranded DNA fragment and a second overhang from a second double-stranded DNA fragment, wherein the first and the second overhangs are complimentary, hybridizing the first and second overhangs to each other; and ligating. Methods are further provided wherein a polymerase lacking 3' to 5' proofreading activity is added during the polynucleotide extension reaction. Methods are further provided wherein the polymerase is a Family A polymerase. Methods are further provided wherein the polymerase is a Family B high fidelity polymerase engineered to tolerate base pairs comprising uracil. Methods are further provided wherein the precursor double-stranded nucleic acid fragments comprise an adaptor sequence comprising the nicking endonuclease recognition site. Methods are further provided wherein one of the plurality of precursor double-stranded nucleic acid fragments is a linear vector. In some aspects, provided herein is a nucleic acid library generated by any of the aforementioned methods.

Methods are provided herein for nucleic acid assembly, comprising: providing a predetermined nucleic acid sequence; synthesizing a plurality of precursor double-stranded nucleic acid fragments, each precursor double-stranded nucleic acid fragment having two strands, wherein each of the two strands comprises a sticky end sequence of 5'-A (Nx) T-3' (SEQ ID NO.: 1) or 5'-G (Nx) C-3' (SEQ ID NO.: 16), wherein N is a nucleotide, wherein x is the number of nucleotides between nucleotides A and T or between G and C, and wherein x is 1 to 10, and wherein no more than two precursor double-stranded nucleic acid fragments comprise the same sticky end sequence; providing primers comprising a nicking endonuclease recognition site and a sequence comprising (i) 5'-A (Nx) M-3' (SEQ ID NO.: 82) corresponding to each of the different sticky end sequences of 5'-A (Nx) T-3' (SEQ ID NO.: 1) or (ii) 5'-G (Nx) M-3'

(SEQ ID NO.: 83) corresponding to each of the different sticky end sequences of 5'-G (Nx) C-3' (SEQ ID NO.: 16), wherein M is a non-canonical base, wherein the primers are each 7 to 70 bases in length; and performing a polynucleotide extension reaction to form double-stranded nucleic acid fragments; subjecting the polynucleotide extension reaction product to nicking and cleavage reactions to form double-stranded nucleic acid fragments with 3' overhangs; and annealing the double-stranded nucleic acid fragments to form a nucleic acid encoding for the predetermined nucleic acid sequence that does not include the nicking endonuclease recognition site. Methods are further provided wherein x is 1, 2, 3, 4, 5, 6, 7, 8, 9, or 10. Methods are further provided wherein x is 4. Methods are further provided wherein the non-canonical base is uracil, inosine, 5-fluorouracil, 5-bromouracil, 5-chlorouracil, 5-iodouracil, hypoxanthine, xanthine, acetylcytosine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N-6-isopentenyl adenine, 1-methylguanine, 1-methylinosine, 2,2-dimethylguanine, 1-methyladenine, 2-methyladenine, 2-methylguanine, 3-methylcytosine, 5-methylcytosine, 5-ethylcytosine, N6-adenine, N6-methyladenine, N,N-dimethyladenine, 8-bromoadenine, 7-methylguanine, 8-bromoguanine, 8-chloroguanine, 8-aminoguanine, 8-methylguanine, 8-thioguanine, 5-ethyluracil, 5-propyluracil, 5-methylaminomethyluracil, methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, 1-methylpseudouracil, queosine, 2-thiocytosine, 5-methyl-2-thiouracil, 2-thiouracil, 4-thiouracil, 5-hydroxymethyluracil, 5-methyluracil, uracil-5-oxyacetic acid methylester, uracil-S-oxyacetic acid, 5-methyl-2-thiouracil, 3-(3-amino-3-N-2-carboxypropyl) uracil, 5-(2-bromovinyl)uracil, 2-aminopurine, 6-hydroxyaminopurine, 6-thiopurine, or 2,6-diaminopurine. Methods are further provided wherein the non-canonical base is incorporated into the double-stranded nucleic acid fragments by performing a nucleic acid extension reaction from a primer comprising the non-canonical nucleotide. Methods are further provided wherein the non-canonical base is a uracil. Methods are further provided wherein the uracil is in a deoxyuridine-deoxyadenosine base pair. Methods are further provided wherein the primers are 10 to 30 bases in length. Methods are further provided wherein one of the plurality of precursor double-stranded nucleic acid fragments comprises a portion of linear vector. Methods are further provided wherein no more than 2 N nucleotides of the sticky end sequence have the same identity. Methods are further provided wherein the precursor double-stranded nucleic acid fragments comprise an adaptor sequence comprising the nicking endonuclease recognition site. Methods are further provided wherein the predetermined nucleic acid sequence is 1 kb to 100 kb in length. Methods are further provided wherein the plurality of precursor nucleic acid fragments are each at least 100 bases in length. Methods are further provided wherein the sticky ends are at least 4 bases long in each precursor nucleic acid. In some aspects, provided herein is a nucleic acid library generated by any of the aforementioned methods.

Methods are provided herein for nucleic acid assembly, comprising: providing a predetermined nucleic acid sequence; synthesizing a plurality of single-stranded nucleic acid fragments, wherein each single-stranded nucleic acid fragment encodes for a portion of the predetermined nucleic acid sequence and comprises at least one sticky end motif, wherein the sticky end motif comprises a sequence of 5-A(N$^x$)T-3' (SEQ ID NO.: 1) or 5'-G(N$^x$)C-3' (SEQ ID NO.: 16) in the predetermined nucleic acid sequence, wherein N is a nucleotide, wherein x is the number of nucleotides between nucleotides A and T or between G and C, and wherein x is 1 to 10, and wherein no more than two single-stranded nucleic acid fragments comprise the same sticky end sequence; amplifying the plurality of single-stranded nucleic acid fragments to generate a plurality of double-stranded nucleic acid fragments, wherein the plurality of double-stranded nucleic acid fragments are modified from the predetermined nucleic acid sequence to comprise (i) a non-canonical base located at a 3' end of the sticky end motif on a first strand and (ii) a first adaptor region located 5' of the non-canonical base on the first strand, wherein the first adaptor region comprises a nicking enzyme recognition site; creating sticky ends, wherein creating sticky ends comprises: treating the plurality of double-stranded fragments with a first nicking enzyme that nicks the non-canonical base on a first strand of each double-stranded fragment, and cleaving the nicked non-canonical base; and treating the plurality of double-stranded fragments with a second nicking enzyme, wherein the second nicking enzyme binds to the first strand at the nicking enzyme recognition site and cleaves a second strand of each double-stranded fragment, wherein a cleavage site for the nicking enzyme is located at a junction between the sticky end motif a sequence reverse complementary to the first adaptor region of the first strand; and annealing the double-stranded nucleic acid fragments to form a nucleic acid encoding for the predetermined nucleic acid sequence that does not include the nicking endonuclease recognition site. Methods are further provided wherein x is 1, 2, 3, 4, 5, 6, 7, 8, 9, or 10. Methods are further provided wherein the predetermined nucleic acid sequence is 1 kb to 100 kb in length. Methods are further provided wherein the predetermined nucleic acid sequence is 1 kb to 25 kb in length. Methods are further provided wherein the predetermined nucleic acid sequence is 2 kb to 20 kb in length. Methods are further provided wherein the predetermined nucleic acid sequence is at least 2 kb in length. Methods are further provided wherein the plurality of single-stranded nucleic acid fragments are each at least 100 bases in length. Methods are further provided wherein the plurality of single-stranded nucleic acid fragments are each at least 500 bases in length. Methods are further provided wherein the plurality of single-stranded nucleic acid fragments are each at least 1 kb in length. Methods are further provided wherein the plurality of single-stranded nucleic acid fragments are each at least 20 kb in length. Methods are further provided wherein the sticky ends are at least 4 bases long. Methods are further provided wherein the sticky ends are 6 bases long. Methods are further provided wherein the non-canonical base is uracil, inosine, 5-fluorouracil, 5-bromouracil, 5-chlorouracil, 5-iodouracil, hypoxanthine, xanthine, acetylcytosine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N-6-isopentenyl adenine, 1-methylguanine, 1-methylinosine, 2,2-dimethylguanine, 1-methyladenine, 2-methyladenine, 2-methylguanine, 3-methylcytosine, 5-methylcytosine, 5-ethylcytosine, N6-adenine, N6-methyladenine, N,N-dimethyladenine, 8-bromoadenine, 7-methylguanine, 8-bromoguanine, 8-chloroguanine, 8-aminoguanine, 8-methylguanine, 8-thioguanine, 5-ethyluracil, 5-propyluracil, 5-methylaminomethyluracil, methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, 1-methylpseudouracil, queosine, 2-thiocytosine, 5-methyl-2-thiouracil, 2-thiouracil, 4-thiouracil, 5-hydroxymethyluracil, 5-methyluracil, uracil-5-oxyacetic acid methylester, uracil-S-oxyacetic acid, 5-methyl-2-thiouracil, 3-(3-amino-3-N-2-carboxypropyl) uracil, 5-(2-bromovinyl)uracil, 2-aminopurine, 6-hydroxyaminopurine, 6-thiopurine, or 2,6-diaminopurine. Methods are further provided wherein the non-canonical base is incorporated into the double-stranded nucleic acid by performing a nucleic acid extension reaction from a primer comprising the non-canonical nucleotide. Methods are further provided wherein the non-canonical base is a uracil. Methods are further provided wherein the uracil is in a deoxyuridine-deoxyadenosine base pair. Methods are further provided wherein the nicking recognition site is a nicking endonuclease recognition site. Methods are further provided wherein the distance between the non-canonical base the nicking enzyme cleavage site is less than 12 base pairs. Methods are further provided wherein the distance between the non-canonical base the nicking enzyme cleavage site is at least 5 base pairs. Methods are further provided wherein the first nicking enzyme comprises a base excision activity. Methods are further provided wherein the first nicking enzyme comprises uracil-DNA glycosylase (UDG). Methods are further provided wherein the first nicking enzyme comprises an AP endonuclease. Methods are further provided wherein the first nicking enzyme comprises endonuclease VIII. Methods are further provided wherein the second nicking enzyme a nicking endonuclease. Methods are further provided wherein the nicking endonuclease is selected from the list consisting of Nb.BbvCI, Nb.BsmI, Nb.BsrDI, Nb.BtsI, Nt.AlwI, Nt.BbvCI, Nt.BsmAI, Nt.BspQI, Nt.BstNBI, and Nt.CviPI0. Methods are further provided wherein each of the plurality of double-stranded nucleic acid fragments further comprises a two sticky ends. Methods are further provided wherein each of the two sticky ends have a different sequence from each other. Methods are further provided wherein the sticky ends comprises a 3' overhang. Methods are further provided wherein the method further comprises ligating the annealed double-stranded nucleic acid fragments. Methods are further provided wherein annealing comprises: thermocycling between a maximum and a minimum temperature, thereby generating a first overhang from a first double-stranded DNA fragment and a second overhang from a second double-stranded DNA fragment, wherein the first and the second overhangs are complimentary; hybridizing the first and second overhangs to each other; and ligating. Methods are further provided wherein the annealed double-stranded nucleic acid fragments comprise a 5' outer adaptor region and a 3' outer adaptor region. Methods are further provided wherein at least two non-identical single-stranded nucleic acid fragments are synthesized. Methods are further provided wherein at least 5 non-identical single-stranded nucleic acid fragments are synthesized. Methods are further provided wherein at least 20 non-identical single-stranded nucleic acid fragments are synthesized. Methods are further provided wherein a polymerase lacking 3' to 5' proofreading activity is added during the amplification step. Methods are further provided wherein the polymerase is a Family A polymerase. Methods are further provided wherein the polymerase is a Family B high fidelity polymerase engineered to tolerate base pairs comprising uracil. Methods are further provided wherein the amplified plurality of single-stranded nucleic acid fragments are not naturally occurring. Provided herein are nucleic acid libraries generated by any of the aforementioned methods.

Provided herein are DNA libraries comprising n DNA fragments, each comprising a first strand and a second strand, each of the n DNA fragments comprising, in order 5' to 3': a first nicking endonuclease recognition site, a first sticky end motif, a template region, a second sticky end motif, and a second nicking endonuclease recognition site, wherein the first sticky end motif comprises a sequence of 5'-A $(N^x)_{i,1}$U-3' (SEQ ID NO.: 13) in the first strand; and wherein the second sticky end motif comprises a sequence of 5'-A $(N^x)_{i,2}$U-3' (SEQ ID NO.: 14) in the second strand; wherein $N^x$ denotes x nucleosides, wherein $(N^x)_{i,2}$ is reverse complementary to $(N^x)_{i,1}$ and different from every other $N^x$ found in any sticky end motif sequence within the fragment library, wherein the first nicking endonuclease recognition site in each of the DNA fragments are positioned such that there is a corresponding cleavage site immediately 3' of the sticky end motif in the second strand, and wherein the second nicking endonuclease recognition sites are positioned such that there is a corresponding cleavage site immediately 3' of the second sticky end motif in the first strand. Libraries are further provided wherein the first nicking endonuclease recognition site, the first sticky end motif, the variable insert, the second sticky end motif site, and the second nicking endonuclease recognition site are ordered as recited. Libraries are further provided wherein the library further comprises a starter DNA fragment comprising a template region, a second sticky end motif, and a second nicking endonuclease recognition site; wherein the second sticky end motif comprises a sequence of 5'-A $(N^x)_{s,2}$ U-3' (SEQ ID NO.: 20) and wherein $(N^x)_{s,2}$ is reverse complementary to $(N^x)_{1,1}$. Libraries are further provided wherein the library further comprises a finishing DNA fragment comprising a first nicking endonuclease recognition site, a first sticky end motif, and a template region; wherein the first sticky end motif comprises a sequence of 5'-A $(N^x)_{f,1}$ U-3' (SEQ ID NO.: 21) and wherein $(N^x)_{f,1}$ is reverse complementary to $(N^x)_{n,2}$. Libraries are further provided wherein the first and second nicking endonuclease recognition sites are the same. Libraries are further provided wherein n is at least 2. Libraries are further provided wherein n is less than 10. Libraries are further provided wherein x is 1, 2, 3, 4, 5, 6, 7, 8, 9, or 10. Libraries are further provided wherein x is 4. Libraries are further provided wherein the template region of each of the n DNA fragments encodes for a different nucleic acid sequencing from the template region of every other of the n DNA fragments. Libraries are further provided wherein the sequences of the n DNA fragments are not naturally occurring. Libraries are further provided wherein the first nicking endonuclease recognition site is not naturally adjacent to the first sticky end motif.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

Figure 1:
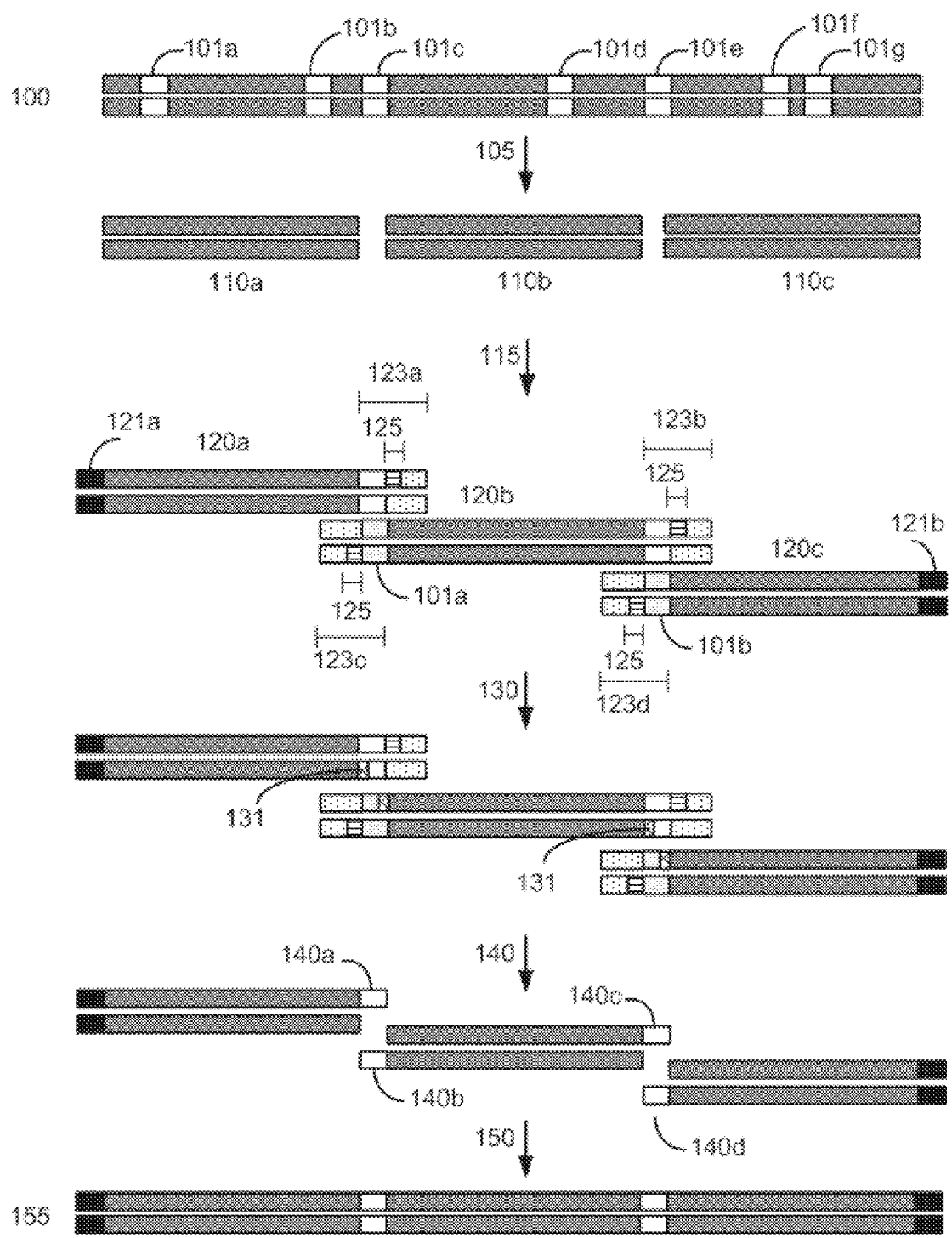
FIG. 1 depicts a workflow through which a nucleic acid product is assembled from 1 kbp nucleic acid fragments.

Disclosed herein are methods and compositions for the assembly of nucleic acid fragments into longer nucleic acid molecules of desired predetermined sequence and length without leaving inserted nucleic acid sequence at assembly points, aka "scar" sequence. In addition, amplification steps are provided during the synthesis of the fragments which provide a means for increasing the mass of a long nucleic acid sequence to be amplified by amplifying the shorter fragments and then rejoining them in a processive manner such that the long nucleic acid is assembled.

DEFINITIONS

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range. As used herein, the terms "preselected sequence", "predefined sequence" or "predetermined sequence" are used interchangeably. The terms mean that the sequence of the polymer is known and chosen before synthesis or assembly of the polymer. In particular, various aspects of the invention are described herein primarily with regard to the preparation of nucleic acids molecules, the sequence of the oligonucleotide or polynucleotide being known and chosen before the synthesis or assembly of the nucleic acid molecules.

The term "nucleic acid" as used herein refers broadly to any type of coding or non-coding, long polynucleotide or polynucleotide analog. As used herein, the term "complementary" refers to the capacity for precise pairing between two nucleotides. If a nucleotide at a given position of a nucleic acid is capable of hydrogen bonding with a nucleotide of another nucleic acid, then the two nucleic acids are considered to be complementary to one another (or, more specifically in some usage, "reverse complementary") at that position. Complementarity between two single-stranded nucleic acid molecules may be "partial," in which only some of the nucleotides bind, or it may be complete when total complementarity exists between the single-stranded molecules. The degree of complementarity between nucleic acid strands has significant effects on the efficiency and strength of hybridization between nucleic acid strands.

"Hybridization" and "annealing" refer to a reaction in which one or more polynucleotides react to form a complex that is stabilized via hydrogen bonding between the bases of the nucleotide residues. The term "hybridized" as applied to a polynucleotide is a polynucleotide in a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of a PCR or other amplification reactions, or the enzymatic cleavage of a polynucleotide by a ribozyme. A first sequence that can be stabilized via hydrogen bonding with the bases of the nucleotide residues of a second sequence is said to be "hybridizable" to the second sequence. In such a case, the second sequence can also be said to be hybridizable to the first sequence. In many cases a sequence hybridized with a given sequence is the "complement" of the given sequence.

In general, a "target nucleic acid" is a desired molecule of predetermined sequence to be synthesized, and any fragment thereof.

The term "primer" refers to an oligonucleotide that is capable of hybridizing (also termed "annealing") with a nucleic acid and serving as an initiation site for nucleotide (RNA or DNA) polymerization under appropriate conditions (i.e. in the presence of four different nucleoside triphosphates and an agent for polymerization, such as DNA or RNA polymerase or reverse transcriptase) in an appropriate buffer and at a suitable temperature. The appropriate length of a primer depends on the intended use of the primer. In some instances, primers are least 7 nucleotides long. In some instances, primers range from 7 to 70 nucleotides, 10 to 30 nucleotides, or from 15 to 30 nucleotides in length. In some instances, primers are from 30 to 50 or 40 to 70 nucleotides long. Oligonucleotides of various lengths as further described herein are used as primers or precursor fragments for amplification and/or gene assembly reactions. In this context, "primer length" refers to the portion of an oligonucleotide or nucleic acid that hybridizes to a complementary "target" sequence and primes nucleotide synthesis. Short primer molecules generally require cooler temperatures to form sufficiently stable hybrid complexes with the template. A primer need not reflect the exact sequence of the template but must be sufficiently complementary to hybridize with a template. The term "primer site" or "primer binding site" refers to the segment of the target nucleic acid to which a primer hybridizes.

Scar-Free Nucleic Acid Assembly

An exemplary workflow illustrating the generation of a target nucleic acid using a scar-free nucleic acid assembly method is shown in FIG. 1. In a first step, the predetermined sequence of a double-stranded target nucleic acid 100 is analyzed to find short sequences, such as sequences of 3, 4, 5, 6, 7, 8, 9, or 10 bases, to serve as sticky end motifs 101a-101g. Each sticky end motif 101a-101g identified in the target nucleic acid need not comprise a sequence unique from another sequence in the target nucleic acid, but each sticky end sequence involved in target nucleic acid assembly is used only once, that is, at only one pair of precursor nucleic acid fragment ends. Sticky end motifs are generally used more than once, that is, at more than one pair of precursor nucleic acid fragment ends. A sticky end motif comprises the sequence A(N$^x$)T (SEQ ID NO.: 1), wherein x indicates from about 1 to about 10, N deoxyribonucleic acid bases of any sequence. For example, x is 4, 5 or 6 and each N may be the same or different from another N in the motif. In some cases, a sticky end motif comprises an ANNNNT (SEQ ID NO.: 2) sequence. After the target nucleic acid sequence 100 is analyzed to identify sticky end motifs 101a-101g and fragment sequences 110a-110c selected 105, the fragments are synthesized 115 with the sticky end motifs from the target nucleic acid 100, for example, by de novo synthesis.

In one example of the de novo synthesis process as illustrated in FIG. 1, synthesis 115 results in double-stranded precursor nucleic acid fragments 120a-120c. Each double-stranded precursor nucleic acid fragments 120a-120c includes an adaptor sequence positioned at either end of target fragment sequence. The outer terminal portions of the double-stranded precursor nucleic acid fragments each comprise an outer adaptor 121a-121b. Each double-stranded precursor nucleic acid fragment 121a-120c is synthesized 115 such that it overlaps with another region of another fragment sequence via sticky end motifs 101a-101g in a processed order. As illustrated in FIG. 1, at the region of the synthesize double-stranded precursor nucleic acid fragment comprising a sticky end motif 101a-101b, synthesis also results in including additional sequence in a connecting adaptor region 123a-123d. The "sticky end motif" occurs at a desired frequency in the nucleic acid sequence. The connecting adaptor region 123a-123d includes a sticky end motif 101a-101b and a first nicking enzyme recognition site 125.

Further processing of the double-stranded precursor nucleic acid fragments 120a-120c is done via primers in an amplification reaction via primers in an amplification reaction 130 to insert a non-canonical base 131. In an alternative method, connecting adaptor regions 123a-123d and/or outer adaptors 120a-120b are and/or are appended to either end of the fragments during a processing step, for example, via primers in an amplification reaction 130.

To generate fragments capable of annealing, the double-stranded precursor nucleic acid fragments 120a-120c as subjected to enzymatic processing 140. Enzymatic processing 140 as illustrated in FIG. 1, entails cleaving portions of the connecting adaptor regions 123a-123d. In a first enzymatic reaction, a first nicking enzyme binds at a first nicking enzyme recognition site 125, and then cleaves the opposite stand. In a second enzymatic reaction, a second nicking enzyme cleaves the non-canonical base 131. The enzymatic reaction results in fragments having stick ends 140a-140d wherein pairs of sticky ends are revers complementary and correspond to sticky end motifs 101a-101b in the original sequence. Finally, the fragments are subjected to an annealing and an ligation reaction 150 to form a reaction product 155 comprising target sequence. The annealing and ligation reactions 150 can include rounds of annealing, ligating and melting under conditions such that only desired sticky ends 140a-140d are able to anneal and ligate, while cleaved end fragments remain unligated. Ordered assembly of nucleic acid fragments includes linear and circular assembly, for example, fragments are assembled with a vector into a plasmid.

In one example, each double-stranded fragment is flanked on a terminal side by a double-stranded connecting adaptor comprising: a double-stranded sticky end motif derived from the target nucleic acid sequence, a nicking enzyme cleavage site located only a first strand of the adaptor, and a double-stranded nicking enzyme recognition sequence, such that upon incubation with a first nicking enzyme specific for the nicking enzyme recognition sequence, a single-strand break is introduced at the nicking enzyme cleavage site in the first strand. In exemplary cases, the sticky end motif of the connecting adaptor is located directly at the 5' or 3' end of a fragment so that each sticky end motif-fragment or fragment-sticky end motif construct comprises sequence native to the predetermined target nucleic acid sequence. The target nucleic acid sequences 100 may be partitioned in sticky end motifs 101a-101g of about 200 bp or other lengths, such as less than or about 50 bp, about 100, 150, 200, 250, 300, 350, 400, 450, 500, 550, 600, 650, 700, 750, 800, 850, 900, 950, or 1000 bp, or more bp.

In various aspects, described herein are double-stranded nucleic acids comprising a first strand having a first cleavage site and a second strand having a second cleavage site; wherein the cleavage sites are positioned one or more bases from one another in sequence. As a non-limiting example, provided are double-stranded nucleic acids comprising a first strand comprising a non-canonical base and a second strand comprising a nicking enzyme cleavage site; wherein the non-canonical base and nicking enzyme cleavage site are positioned one or more bases from one another in sequence. Through the combined action of nicking enzymes directed to act in tandem at adjacent or near adjacent positions on opposite strands of a double-stranded nucleic acid, one may impact the generation of a sticky end at or near the end of a first nucleic acid fragment, wherein the sticky end sequence is unique and complementary only to the sticky end of a second nucleic acid fragment sequentially adjacent thereto in a predetermined sequence of a full-length target nucleic acid to be assembled from the fragments.

An example workflow illustrating the generation of a nick at a non-canonical base in a nucleic acid is shown in FIGS. 2A-2B. As a preliminary step, as illustrated in FIG. 1, a predetermined sequence of a target nucleic acid is partitioned in silico into fragments, where the sequence of each fragment is separated from an adjacent fragment by an identified sticky end motif. The connecting adaptor regions 123a-123d appended to an end of a fragment include a sticky end motif corresponding to the sticky end motif 101a-101g adjacent to the fragment such that each motif can processively be aligned during enzymatic processing. For example, the 3' end of a first fragment 201 is configured for connection to the 5' end of fragment 2 202 via a sticky end motif X 211a. Similarly, fragment 2 201 is configured for connection to fragment 3 203 in the target sequence via sticky end motif Y 211*d* and fragment 3 203 is configured for connection to fragment 4 204 in the target sequence via sticky end motif Z 211*c*.

In some instances, a connecting adaptor comprises a first and a second nicking enzyme recognition site such that tandem nicks made to the connecting adaptor do not affect the sequence of the fragment to which the adaptor is connected. For example, a detailed view of precursor fragments 203 and 204 having such connecting adaptors is show in FIGS. 2 (220 and 215, respectively). The 5' connecting adaptor of the fragment 4 204 comprises a first double-stranded nicking enzyme recognition site 225, a first nicking enzyme cleavage site 227 located on a first single-strand 221, and a double-stranded sticky end motif Z (AAGTCT, SEQ ID NO.: 3) modified with a uracil (AAGTCU, SEQ ID NO.: 4) on a second single-strand 223. The 3' connecting adaptor of fragment 3 230 comprises the double-stranded sticky end motif Z 211*c* (SEQ ID NO.: 3) modified with a uracil (AGACTU, SEQ ID NO.: 5) on a first single-strand 229, the first nicking enzyme cleavage site 227 on a second single-strand 231, and the first double-stranded nicking enzyme recognition site 225. Accordingly, each strand of the connecting adaptors comprise two nicking sites—a first nicking enzyme cleavage site and a uracil—located at different positions and strands in the adaptor sequence.

Continuing this exemplary workflow, nicking reactions 240 are next described. The first nicking enzyme cleavage site 227 is located at the backbone of a single-strand of each connecting adaptor, adjacent to a first nicking enzyme recognition sequence 225. In some instances, the cleavage site is located at a position adjacent to a 5' or 3' end of a nicking enzyme recognition site by 1, 2, 3, 4, 5, 6, 7, 8, 9 or 10 bases. Fragments are treated with a first nicking enzyme, in this case, a strand-adjacent nicking enzyme, which cleaves a single-strand of the connecting adaptor at the first nicking enzyme cleavage site; and a second nicking enzyme which excises uracil and cleaves a single-strand of the connecting adaptor at the excised uracil site. Cleaved fragments 241, 242 comprise sticky end overhangs. Fragments comprising complementary sticky end overhangs are annealed and ligated 250. The ligation product 260 comprises predetermined target nucleic acid sequence comprising adjacent fragments separated by a sticky end motif, without the introduction of extraneous scar sequence.

As used herein, a sticky end motif includes forward, reverse, and reverse complements of a sticky end sequence. For example, a first strand of sticky end motif Z comprises SEQ ID NO.: 3 and a second strand of sticky end motif Z comprises the reverse complement of SEQ ID NO.: 3, AGACTT (SEQ ID NO.: 6), FIG. 2.

To prepare double-stranded precursor fragments with one or two nicking enzyme cleavage sites, precursor fragments are either synthesized with one or both sites, assembled from smaller nucleic acids comprising one or both sites, amplified with a primer comprising one or both sites, or any combination of the methods described or known in the art. For example, a precursor fragment can comprise a sticky end sequence and a primer is synthesized comprising a sequence that is complementary to the sticky end sequence, yet comprises a non-canonical base substitution at the 3' end of the sticky end sequence. Amplification of precursor nucleic acid fragments comprising sticky end sequences with the primer may introduce the non-canonical base to the precursor fragment sequence so that the precursor fragment amplicons comprise a nicking enzyme cleavage site defined by the position of the non-canonical base. In one example, a double-stranded precursor fragment is prepared comprising, in 5' to 3' or 3' to 5' order: a first double-stranded nicking enzyme recognition sequence, a first nicking enzyme cleavage site on a first single-strand, a double-stranded sticky end motif, and a double-stranded fragment of predetermined target sequence; wherein amplification of the precursor fragment with a non-canonical base-containing primer as described introduces a second nicking enzyme cleavage site between the sticky end motif and fragment of predetermined target sequence on a second single-strand.

In some cases, a collection of precursor nucleic acid fragments is provided, each precursor nucleic acid fragment comprising a fragment sequence of a predetermined sequence of a target nucleic acid and a 5' and/or 3' connecting adaptor, wherein each connecting adaptor comprises a shared sequence among the precursor fragments and optionally one or more bases variable among the precursor fragments. Amplification of collective fragments comprising a shared sequence can be performed using a universal primer targeting shared sequence of the adaptors.

Figure 3:
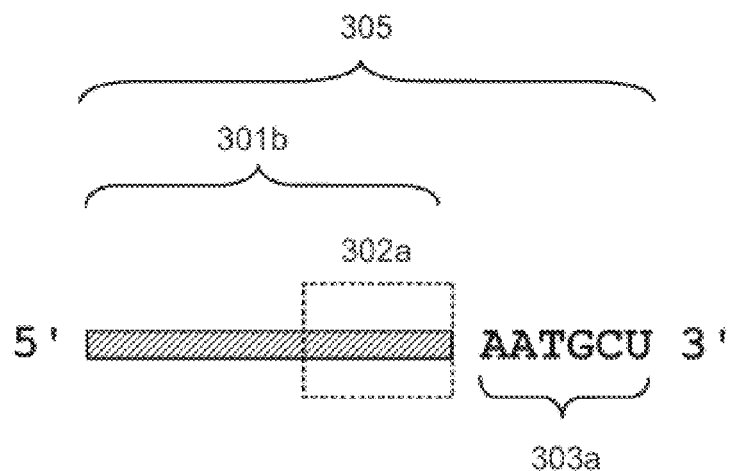
FIG. 3 depicts a uracil-containing universal primer pair, and discloses SEQ ID NOS.: 7, 2, 8 and 2, respectively, in order of appearance.
Figure 3:
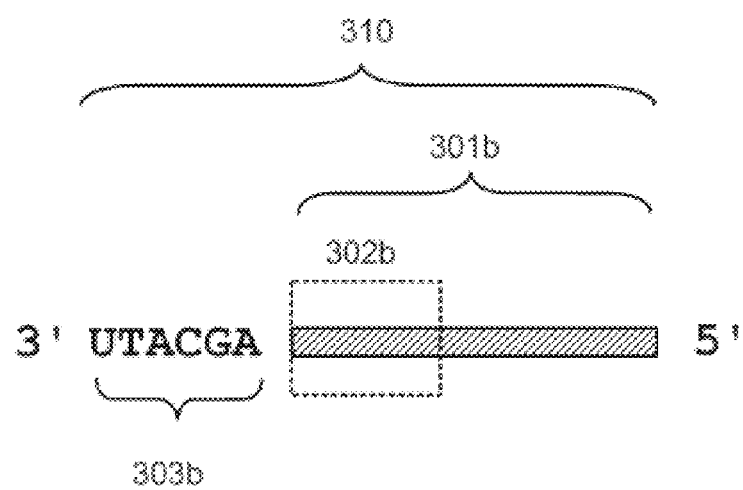

An exemplary universal primer is one that comprises a base or sequence of bases which differs from a shared adaptor sequence of precursor nucleic acid fragments. For example, a universal primer comprises a non-canonical base as an addition and/or base substitution to shared adaptor sequence, and amplification of precursor fragments comprising the shared adaptor sequence with the primer introduces the non-canonical base into each adaptor sequence. An illustration of an exemplary universal primer pair comprising a non-canonical base substitution is shown in FIG. 3. Each primer comprises, in 5' to 3' order: one or more adaptor bases 301*a*, 301*b*, a nicking enzyme recognition site 302*a*, 302*b*, and a sticky end motif comprising a T to U base substitution (sticky end motif in forward primer 305: AATGCU, SEQ ID NO.: 7 303*a*; sticky end motif in reverse primer 310: AGCATU, SEQ ID NO.: 8 303*b*). Amplification of a first precursor nucleic acid having an adaptor comprising sticky end motif AATGCT (SEQ ID NO.: 9) with the forward primer introduces a uracil to a single-strand of the adaptors in the resulting amplicons. Amplification of a second precursor nucleic acid having an adaptor comprising sticky end motif AGCATT (SEQ ID NO.: 10) with the reverse primer introduces a uracil to a single-strand of the adaptors in the resulting amplicons. The amplification products, cleavage steps described herein, have compatible sticky ends are suitable for annealing and ligating. In some cases, a set of two or more universal primer pairs is used in a method disclosed herein, wherein each pair comprises a universal forward primer and a universal reverse primer, and wherein the forward primers in the set each comprise a shared forward sequence and a variable forward sequence and the reverse primers in the set each comprise a shared reverse sequence and a variable reverse sequence. A set of universal primers designed to amplify the collection of nucleic acids may comprises differences within each set of universal forward and reverse primers relating to one or more bases of the sticky end motif sequence.

Provided herein are methods where a universal primer pair incorporates a universal primer sequence 5' to a sticky end motif sequence in a nucleic acid. As a non-limiting example, a universal primer sequence comprises a universal nicking enzyme recognition sequence to be incorporated at the end of each fragment in a library of precursor nucleic acid fragments. For the universal primers shown in FIG. 3, as one example, a primer fusion site comprises four bases 3' to an adenine (A) and 5' to a uracil (U). The 5'-A ($N^4$) U-3' (SEQ ID NO.: 11) primer fusion sequence is located at the very 3' end of the exemplary primers, which conclude with a 3' uracil. Alternatively, the primer fusion can be sequence is 5'-G ($N^4$) U-3' (SEQ ID NO.: 12). For some assembly reactions with precursor nucleic acid fragments, a number of such primers with varying $N^4$ sequences are used within a reaction mixture, each targeting a complementary fusion site on one end of one of the fragments that are to be assembled. $N^4$ represents any configuration of 4 bases (N), where each base N has the same or different identity than another base N. In some cases, the number of N bases is greater than or less than 4. Without being bound by theory, since mismatched base pairs toward the 3' end of a primer significantly reduce the efficiency of a nucleic acid extension reaction, placement of variable regions that target different fusion sites increases the specificity between the primer fusion site sequences and fragment fusion site sequences.

Figure 4:
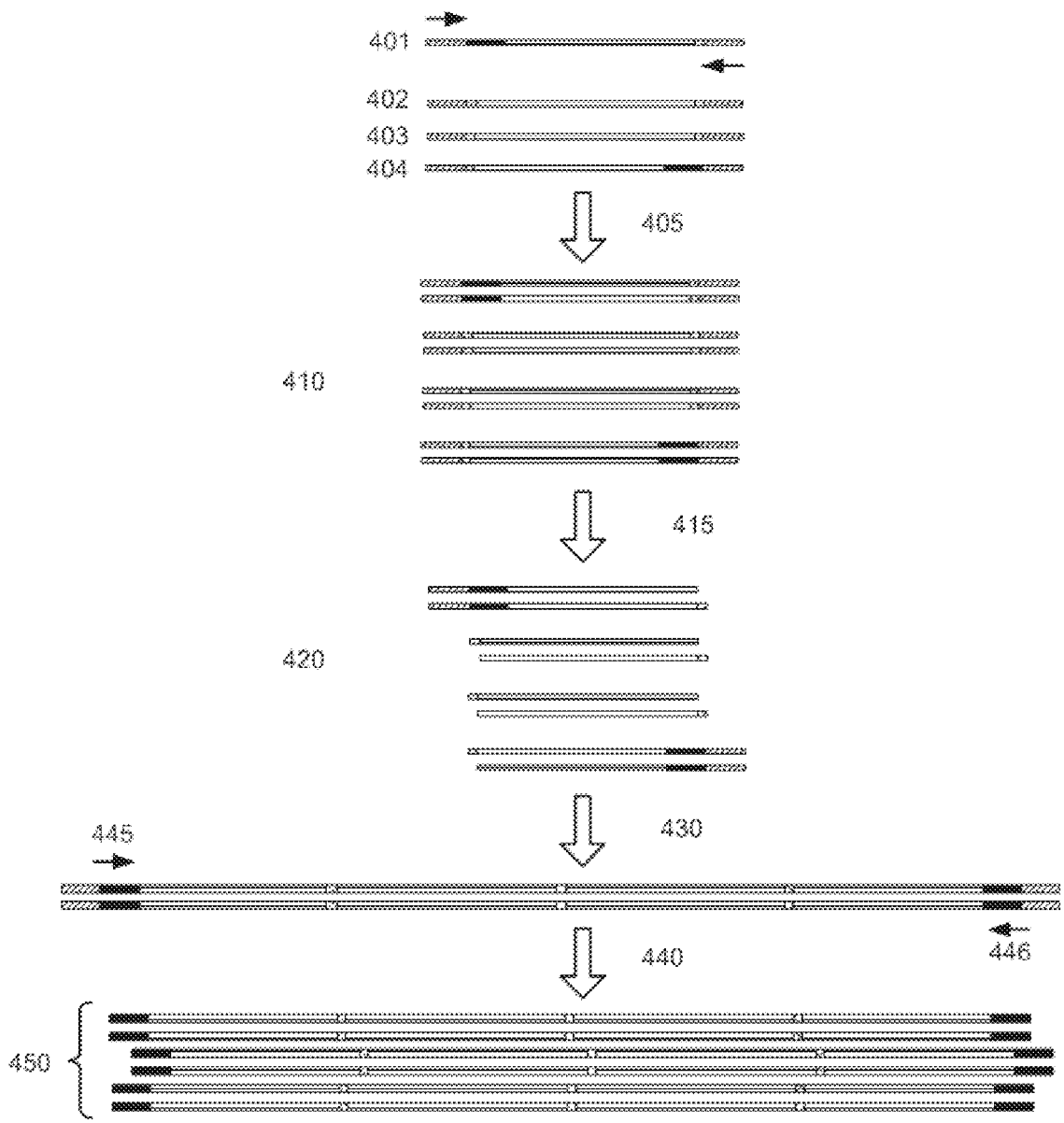
FIG. 4 depicts the assembly of a nucleic acid product from oligonucleic acid fragments having complementary overhangs.

A plurality of precursor nucleic acid fragments comprising shared and variable regions of sequence is shown in FIG. 4. Each precursor fragment 401-404 comprises at least one connecting adaptor and optionally an outer adaptor at each end of a target fragment sequence, wherein each of the connecting and outer adaptors comprise a shared sequence. Following PCR amplification 405 with primers (designate by arrows in above and below "401" in FIG. 4), the precursor fragment 401-404 are modified to include non-canonical bases 410, subject to enzymatic digestion 415 to generate fragments with overhangs 420, and subject to annealing and ligation 430. The primers may be universal primers described herein. The nucleic acids comprising fragment 1 401 and fragment 2 402 are appended at their 3' or 5' ends, respectively, with sticky end motif X, wherein the sequence: fragment 1-sticky end motif X-fragment 2 occurs in the predetermined target sequence. The nucleic acids comprising fragment 2 402 and fragment 3 403 are appended at their 3' or 5' ends, respectively, with sticky end motif Y, wherein the sequence fragment 2-sticky end motif Y-fragment 3 occurs in the predetermined target sequence. The nucleic acids comprising fragment 3 403 and fragment 4 404 are appended at their 3' or 5' ends, respectively, with sticky end motif Z, wherein the sequence fragment 3-sticky end motif Z-fragment 4 occurs in the predetermined target sequence. The ligation product is then amplified by PCR 440 using primers 445, 446 complementary to outer adaptors regions. The resulting final product is a plurality of nucleic acids which lack adaptor regions 450.

Connecting adaptors disclosed herein may comprise a Type II restriction endonuclease recognition sequence. In such instances, a sticky end motif shared between adjacent fragments in a predetermined sequence is a Type II restriction endonuclease recognition sequence. As a non-limiting example, sticky end motif X is a first Type II restriction endonuclease recognition sequence so that upon digesting with the appropriate Type II restriction enzyme, a sticky end is produced at the ends of nucleic acids 401 and 402. As another example, sticky end motifs Y and Z are also two different Type II restriction endonuclease recognition sequences native to the predetermined target nucleic acid sequence. In such cases a target nucleic acid having no scar sites is assembled from the Type II-digested fragments. In some cases, fragments assembled using Type II restriction endonucleases are small, for example, less than about 500, 200, or 100 bases so to reduce the possibility of cleavage at a site within the fragment sequence. In some instances, a combination of tandem, single-strand breaks and Type II restriction endonuclease cleavage is used to prepare precursor fragments for assembly.

In some cases, tandem nicking of a double-stranded nucleic acid and/or double-stranded cleavage by a Type II restriction endonuclease, results in undesired sequences terminal to cleavage sites remaining in the cleavage reaction. These terminal bases are optionally removed to facilitate downstream ligation. Cleaved termini are removed, for example, through size-exclusion column purification. Alternately or in combination, terminal ends are tagged with an affinity tag such as biotin such that the cleaved ends are removed from the reaction using avidin or streptavidin, such as streptavidin coated on beads. Alternately, for tandem nicking reactions, cleaved ends of precursor fragments are retained throughout annealing of the fragments to a larger target nucleic acid.

Provided herein are methods where the precursor fragments comprise a first nicking enzyme cleavage site defined by a first nicking enzyme recognition sequence, and a non-canonical base. In these cases, precursor fragments are treated with a first enzyme activity that excises the non-canonical base and a second enzyme activity that cleaves single-stranded nucleic acids at the abasic site and first nicking enzyme cleavage site. Some of the cleaved ends produced at the first nicking enzyme cleavage site are able to reanneal to cleaved sticky end overhangs, and may re-ligate. However, such re-ligation will also reconstitute the cleavage site, and will be re-cleaved if the single-strand nicking enzyme activity is included in the reaction. The opposite strand, from which the non-canonical base has been excised and the phosphodiester backbone cleaved at that site, is incapable of re-ligation to the cleaved end because of the gap created at the now abasic site. However, sticky ends of precursor nucleic acid fragments that are end pairs intended to assemble into a larger fragment are capable of annealing to one another and ligating. Upon ligation, the molecule formed thereby will not have the first nicking enzyme cleavage site, as the sequence that specifies cleavage is in the cleaved-off terminal fragment rather than in the adjacent fragment sequence. Subsequently, ligated ends will not be re-cleaved by strand-adjacent nicking enzyme. Additionally, as neither strand has a gap position corresponding to the excised non-canonical base position, sticky ends of precursor nucleic acid fragments that are end pairs intended to assemble into a larger target are capable of annealing to one another across both strands.

Following successive rounds of thermocycling through annealing, ligation and denaturing, optionally in the presence of a nicking enzyme, sticky ends that bind to their partner ends will be ligated and drawn out of the sticky end pool, while sticky ends that bind to cleaved terminator sequence will remain available for ligation in successive rounds. Through successive iterations of annealing, ligation and melting, cleaved ends remain unligated while junction binding events become ligated to one another.

Sticky ends of cleaved precursor nucleic acid fragments are allowed to anneal to one another under conditions promoting stringent hybridization, such that in some cases, only perfectly reverse complementary sticky ends anneal. In some cases, less stringent annealing is permitted. Annealed sticky ends are ligated to form either complete target nucleic acid molecules, or larger fragment target nucleic acid molecules. Larger fragment molecules are in turn subjected to one or more additional rounds of assembly, using either methods described herein and additional sticky end sites, or one or more assembly techniques known in the art.

Methods and compositions described herein allow assembly of large nucleic acid target molecules with a high degree of confidence as to sequence integrity. The target molecules are assembled from precursor nucleic acid fragments that are in many cases synthesized to a length that is within a target level of sequence confidence—that is, they are synthesized to a length for which the synthesis method provides a high degree of confidence in sequence integrity. In some cases, this length is about 100, 150, 200, 250, 300, 350, 400, 450, or 500 nucleic acid bases.

In some cases, the methods provided herein generate a specific target sequence for a recombinatorial library, e.g., a chimeric construct or a construct comprising at least one targeted variation for codon mutation. Positions to vary include, without limitation, codons at residues of interest in an encoded protein, codons of residues of unknown function in an encoded protein, and pairs or larger combinations of codons encoding residues known or suspected to work in concert to influence a characteristic of a protein such as enzymatic activity, thermostabilty, protein folding, antigenicity, protein-protein interactions, solubility or other characteristics.

A library of variants may be prepared by synthesizing target nucleic acids from fragments having at least one indeterminate or partially determinate position among members of the library. In some cases, target fragments are synthesized having combinations of variants. Upon assembly of a target nucleic acid library, multiple combinations of variations at a first position and variations at a second position may be present in the library. In some instances, all possible combinations of variants are represented in a library. The library may be constructed such that variant base positions are each found on different target fragments, or alternately, multiple variant base positions are found on the same target fragment library.

Figure 5A:
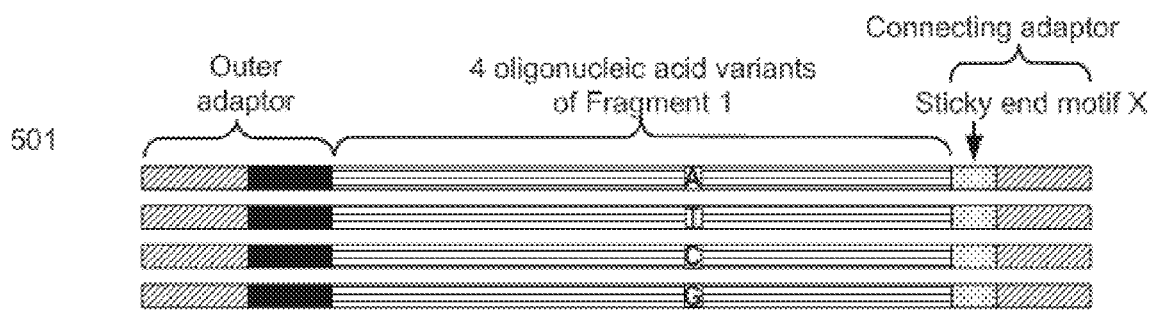
FIGS. 5A-5B depict the assembly of a recombinatorial library from a library of nucleic acid fragments each having at least one unspecified base.
Figure 5A:
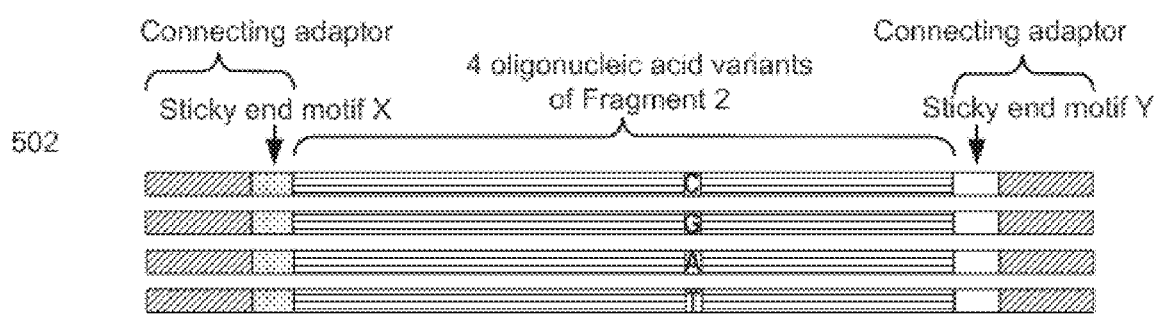
Figure 5A:
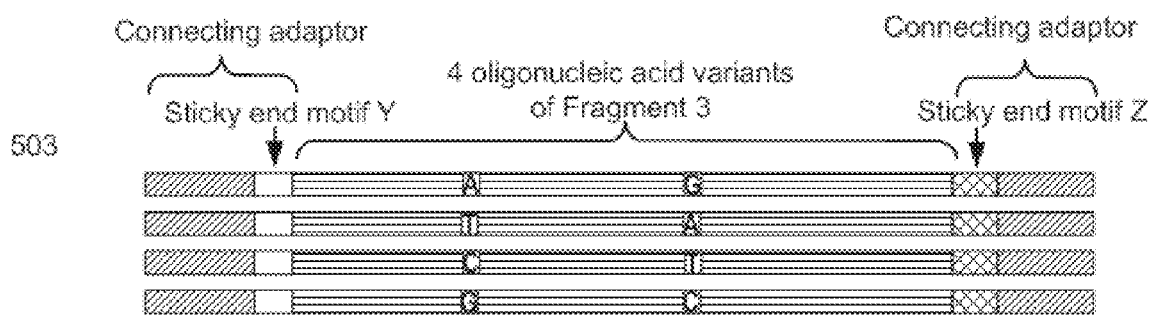
Figure 5A:
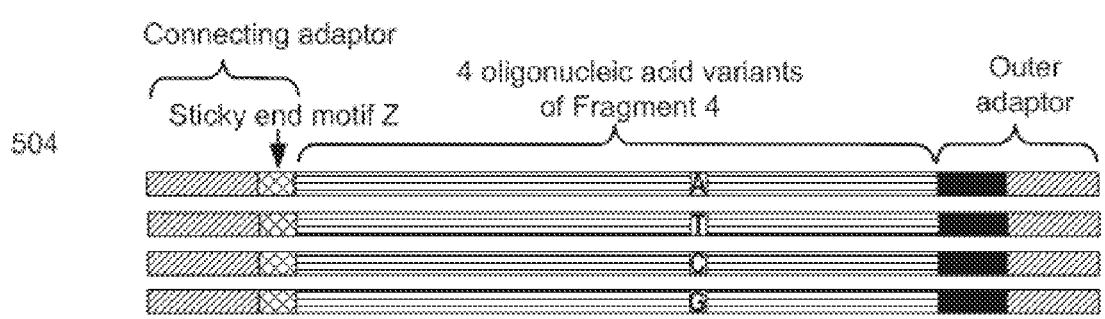
Figure 5B:
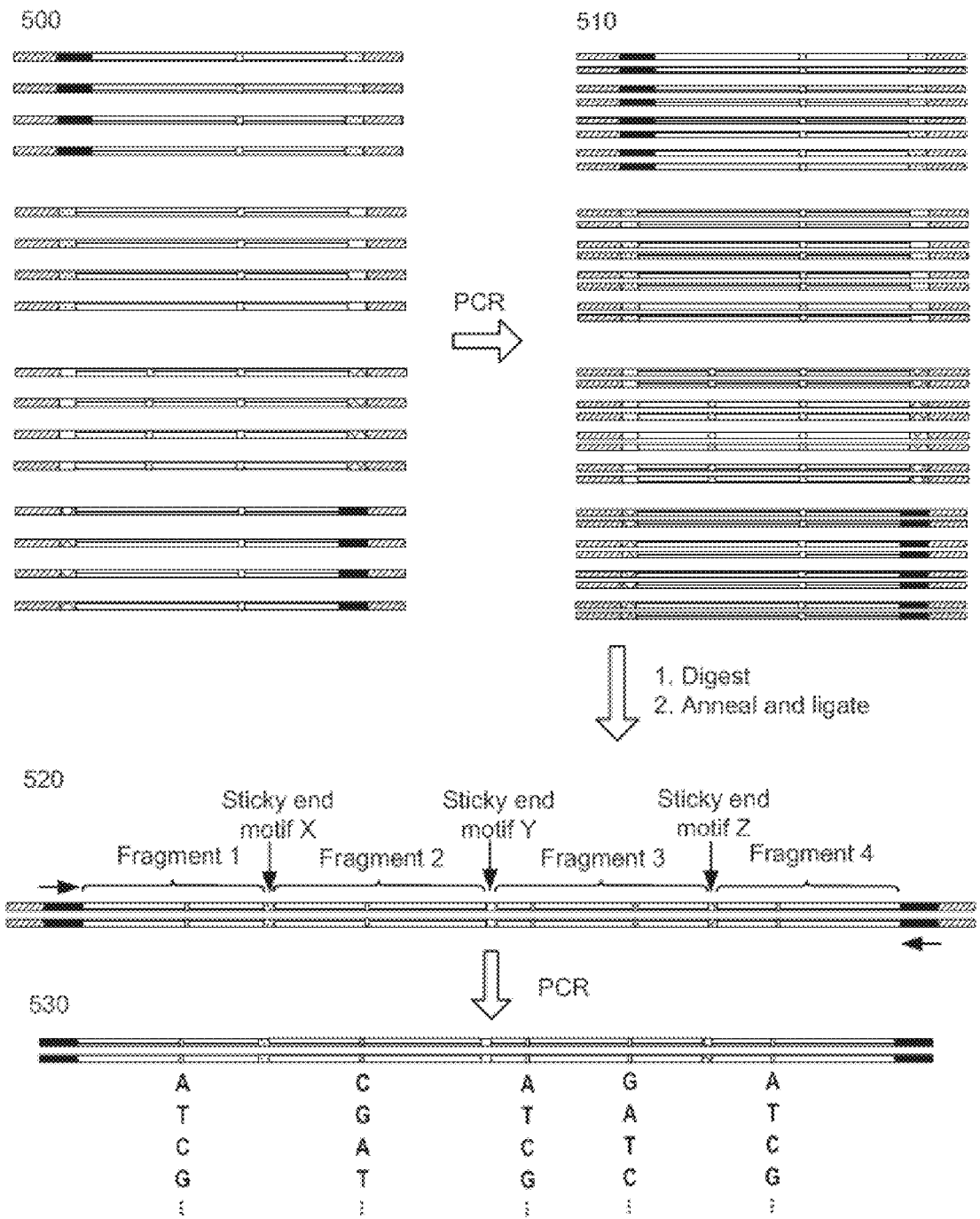

FIGS. 5A-5B illustrate an exemplary workflow for recombinatorial library synthesis of a target gene. The target gene is partitioned into fragments 1-4 by motifs X, Y, and Z 500, each fragment comprising one or two indeterminate sites (FIG. 5A). In some instances, not all fragments of a target gene comprise an indeterminate site. Precursor fragments 501 comprise an outer adaptor, a variant of fragment 1 comprising one indeterminate site, and a connecting adaptor comprising motif X. Precursor fragments 502 comprise a connecting adaptor comprising motif X, a variant of fragment 2 comprising one indeterminate site, and a connecting adaptor comprising motif Y. Precursor fragments 503 comprise a connecting adaptor comprising motif Y, a variant of fragment 3 comprising two indeterminate sites, and a connecting adaptor comprising motif Z. Precursor fragments 504 comprise a connecting adaptor comprising motif Z, a variant of fragment 4 comprising one indeterminate sites, and a second outer adaptor. PCR is used to generate amplicons 510 of each precursor fragment, collectively, 500, In some cases, using a universal primer pair(s) (FIG. 5B). Precursor nucleic acids are digested at their connecting adaptor sequence to generate sticky ends, complements of which are annealed and ligated together to form a series of target genes comprising: fragment 1 sequence comprising one indeterminate site, motif X, fragment 2 sequence comprising one indeterminate site, motif Y, fragment 3 sequence comprising two indeterminate sites, motif Z, and fragment 4 sequence comprising one indeterminate site 520. The number of possible target gene variants is $4^5$ or 1,024 different genes. FIG. 5B, part 530, shows a conceptual depiction of some of these target gene variants after PCR amplification.

Methods described herein comprise assembling double-stranded DNA ("dsDNA") target nucleic acid from shorter target nucleic acid fragments that are building block precursors. Assembly may proceed by hybridizing uniquely complimentary pairs of overhangs. Such uniquely complimentary pairs may be formed by incorporating sticky ends from two precursor fragments that appear successively in the assembled nucleic acid. In some cases, the pair of overhangs does not involve complete complementarity, but rather sufficient partial complementarity that allows for selective hybridization of successive precursor fragments under designated reaction conditions.

Generation of an overhang on a double-stranded nucleic acid is generally performed with two cleavage agents. A cleavage agent includes any molecule with enzymatic activity for base excision and/or single-strand cleavage of a double-stranded nucleic acid. For example, a cleavage agent is a nicking enzyme or has nicking enzymatic activity. A cleavage agent recognizes a cleavage or nicking enzyme recognition sequence, mismatched base pair, atypical base, non-canonical or modified nucleoside or nucleobase to be directed to a specific cleavage site. In some cases, two cleavage agents have independent recognition sites and cleavage sites. In some cases, a cleavage agent generates a single-stranded cleavage, e.g., a nick or a gap, involving removal of one or more nucleosides from a single-strand of a double-stranded nucleic acid. In some cases, a cleavage agent cleaves a phosphodiester bond of a single-strand in a double-stranded nucleic acid.

Provided herein area methods for creating a sticky end on a double-stranded nucleic acid comprising: (a) providing a linear double-stranded nucleic acid comprising in order an insert region, a first fusion site, and a first adaptor region; (b) creating a first nick on a first strand of the double-stranded nucleic acid with a first cleavage agent having a first recognition site and a first specific cleavage site; and (c) creating a second nick on a second strand of the double-stranded nucleic acid with a second cleavage agent having a second recognition site and a second specific cleavage site; wherein the method produces a sticky end at the first fusion site; wherein the first recognition site is in the first fusion site or the first adaptor region; and wherein the second recognition site is in the first fusion site or first adaptor region. In some cases, the first adaptor region or first fusion site comprises a sticky end motif. In some cases, the first adaptor region or first fusion site comprises a strand-adjacent nicking enzyme recognition sequence. In some cases, a precursor nucleic acid sequence comprises a fusion site and adaptor region that is not naturally adjacent to each other.

Provided herein are methods for creating sticky ends on double-stranded nucleic acid comprising: (a) providing a plurality of double-stranded nucleic acids each comprising in order an insert region, a fusion site, and an adaptor region, wherein each of the plurality of double-stranded nucleic acids have a different fusion site; (b) creating a first nick on a first strand of each of the plurality of double-stranded nucleic acids with a first cleavage agent having a first recognition site and a first specific cleavage site; and (c) creating a second nick on a second strand of each of the plurality of double-stranded nucleic acids with a second cleavage agent having a second recognition site and a second specific cleavage site; wherein the method produces a sticky end at each fusion site of the plurality of double-stranded nucleic acids; wherein the first recognition site is in the fusion site or the adaptor region of the plurality of double-stranded nucleic acids; and wherein the second recognition site is in the fusion site or adaptor region of the plurality of double-stranded nucleic acids. In some cases, the first adaptor region or first fusion site comprises a sticky end motif. In some cases, the first adaptor region or first fusion site comprises a strand-adjacent nicking enzyme recognition sequence.

Provided herein are methods for assembling a polynucleotide comprising: (a) providing a reaction mixture comprising a first dsDNA fragment comprising a uracil base on its first strand; a second dsDNA fragment comprising a uracil base on its first strand; a first cleaving agent that cuts dsDNA on a single-strand at the site of a uracil; a second cleaving agent that cuts dsDNA on a single-strand, wherein the cleavage site of the second cleaving agent is within k by of the uracil in an opposite strand and wherein k is between 2 and 10; and a ligase; and (b) thermocycling the reaction mixture between a maximum and a minimum temperature, thereby generating a first overhang from the first dsDNA fragment and a second overhang from the second dsDNA fragment, wherein the first and the second overhangs are complimentary, hybridizing the first and second overhangs to each other, and ligating.

Provided herein are methods for assembling a polynucleotide comprising: (a) providing a reaction mixture comprising n dsDNA fragments each comprising a first and a second strand, and a first nicking endonuclease recognition site, a first fusion site, a variable insert, a second fusion site, and a second nick enzyme recognition site, wherein the second fusion site comprises a uracil base on the first strand and the first fusion site comprises a uracil base on the second strand; a first cleaving agent that cuts dsDNA on a single-strand at the site of a uracil; a second cleaving agent that cuts dsDNA on a single-strand, wherein the cleavage site of the second cleaving agent is within k by of the uracil in an opposite strand and wherein k is between 2 and 10; and a ligase; and (b) thermocycling the reaction mixture between a maximum and a minimum temperature, thereby generating a first overhang and a second overhang on each end of the n dsDNA fragments, wherein the second overhang on the ith of the n dsDNA fragments is reverse complementary to the first overhang on the i+1st of the n dsDNA fragments, hybridizing the complementary overhangs to each other, and ligating.

Provided herein are fragment libraries comprising n DNA fragments, each comprising a first strand and a second strand, each ith DNA fragment comprising a first nicking endonuclease recognition site, a first fusion site, a variable insert, a second fusion site, and a second nick enzyme recognition site; wherein the first fusion site comprises a sequence of 5'-A $(Nx)_{i,1}$ U-3' (SEQ ID NO.: 13) in the first strand; and wherein the second fusion site comprises a sequence of 5'-A $(Nx)_{i,2}$ U-3' (SEQ ID NO.: 14) in the second strand; wherein Nx denotes x nucleosides; wherein $(Nx)_{i,2}$ is reverse complementary to $(Nx)_{i+1,1}$ and different from every other Nx found in any fusion site sequence within the fragment library; wherein the first nicking endonuclease recognition sites are positioned such that there is a corresponding cleavage site immediately 3' of the first fusion site in the second strand; and wherein the second nicking endonuclease recognition sites are positioned such that there is a corresponding cleavage site immediately 3' of the second fusion site in the first strand.

Provided herein are primer libraries comprising n primers, each comprising a nicking endonuclease recognition sequence and a fusion sequence comprising 5'-A $(Nx)_i$ U-3' (SEQ ID NO.: 15), wherein the nicking endonuclease recognition sequence is positioned 5' of the fusion sequence. In some cases, the nicking endonuclease recognition sites are positioned such that the nicking endonuclease recognition site in a primer is capable of generating a corresponding cleavage site in a reverse complimentary DNA strand 3' of a first fusion site in the reverse complimentary DNA strand, if the primer were hybridized to the reverse complementary DNA strand such that the fusion sequence hybridizes to the first fusion site in the reverse complementary DNA strand. In some cases, x is selected from the list consisting of the integers 1, 2, 3, 4, 5, 6, 7, 8, 9, and 10. In some cases, n is at least 2. In some cases, n is less than 10. In some cases, the sequences of the n primers are not naturally occurring. In some cases, the primers are in a kit further comprising a nicking endonuclease, UDG, and an AP endonuclease.

A primer is said to anneal to another nucleic acid if the primer, or a portion thereof, hybridizes to a nucleotide sequence within the nucleic acid. The statement that a primer hybridizes to a particular nucleotide sequence is not intended to imply that the primer hybridizes either completely or exclusively to that nucleotide sequence.

Sticky Ends

Provided herein are methods for the creation of a sticky end on a nucleic acid using a combination of independently acting single-strand cleaving enzymes rather than a single restriction endonuclease. In some cases, a sticky end is an end of a double-stranded nucleic acid having a 5' or 3' overhang, wherein a first strand of the nucleic acid comprises one or more bases at its 5' or 3' end, respectively, which are collectively not involved in a base-pair with bases of the second strand of the double-stranded nucleic acid. An overhang is capable of annealing to a complementary overhang under suitable reaction conditions. In some cases, "sticky end" and "overhang" are used interchangeably. Non-limiting examples of overhang lengths include 1, 2, 3, 4, 5, 6, 7, 8, 9, 10 or more bases. For example an overhang has 4 to 10 bases, 4 to 8 bases, or 4 to 6 bases.

Sticky end motifs are generally identified from a predetermined sequence of a target nucleic acid to be synthesized from fragments partitioned by selected identified sticky end motifs. In some cases, ANNNNT (SEQ ID NO.: 2) motifs are identified as sources of potential sticky ends in a target sequence. In some cases, GNNNNC (SEQ ID NO.: 17) motifs are identified as a source of potential sticky ends in a target sequence. Each N is independently any base. Selected sticky ends serve as fusion sites for annealing and ligating together two fragments via complementary sticky ends.

In some cases, a sticky end comprises a sequence of A $(N^x)$ T (SEQ ID NO.: 1), wherein $N^x$ is x number of N bases of any sequence. In some cases, a sticky end comprises a sequence of G $(N^x)$ C (SEQ ID NO.: 16), wherein $N^x$ is x number of N bases of any sequence. A sticky end motif is a sequence of double-stranded polynucleotides in a nucleic acid that when treated with an appropriate cleavage agent make up a sticky end. For reactions comprising a plurality of double-stranded nucleic acid fragments to be assembled, in some instances the $N^x$ sequence or full sequence of a sticky end at the 3' end of a first nucleic acid fragment is completely or partially reverse complementary to the $N^x$ sequence of a sticky end at the 5' end of a second nucleic acid fragment. In similar instances the 3' end of the second nucleic acid fragment has a sticky end that is completely or partially reverse complementary to the $N^x$ sequence of sticky end at the 5' end of a third nucleic acid fragment, and so on. In some instances, the motif of the sticky end complementary between the first and second nucleic acids is the same as the motif of the sticky end complementary between the second and third nucleic acids. This sequence similarity between sticky end motifs includes motifs having identical base number and sequence identities. In some cases, sticky end motifs of a plurality of nucleic acids are the same, yet have variable identities. For example, each motif shares the sequence ANNNNT (SEQ ID NO.: 2), but two or more motifs differ in the identity of the sequence of 4, N bases. A plurality of nucleic acid fragments to be assembled may each comprise a sticky end motif of A ($N^x$) T (SEQ ID NO.: 1), wherein the sequence of a given motif is only shared among two of the fragments adjacent to one another in a target nucleic acid sequence. Thus, these nucleic acid fragments, under appropriate conditions, anneal to each other in a linear sequence without degeneracy in the pairing of overhangs and hence the nucleic acid order within the linear sequence.

The number of bases x in $N^x$ in a sticky end motif described herein may be the same for all sticky end motifs for a number of nucleic acids within a plurality of nucleic acids. In some instances, sticky end motifs belonging to a number of nucleic acids within a plurality of nucleic acids comprise sequences of A ($N^x$) T (SEQ ID NO.: 1), G ($N^x$) C (SEQ ID NO.: 16), or combinations thereof, wherein the number of bases x in $N^x$ is the same or varies among the plurality of nucleic acids. The number of bases x in $N^x$ may be more than or equal to about 1, 2, 3, 4, 5, 6, 7, 8, 9, 10, or more. In some cases, the number of bases x in $N^x$ sticky end motifs of a plurality of nucleic acids is less than or equal to 20, 19, 18, 17, 16, 15, 14, 13, 12, 11, 10, 9, 8, 7, 6, 5, 4, 3, or 2 bases. In some cases, the number of bases x in $N^x$ in sticky end motifs is 2-10 bases, 3-9 bases, 4-8 bases, or 5-10 bases. In some case, a sequence of N bases in a sticky end motif described herein comprises no more than 4, 3, 2, or 1 of the same base. For example, in a sticky end motif comprising x=4 N bases, no more than 1, 2, 3 or 4 bases have the same identity. In some cases, no more than 2, 3 or 4 bases in a sticky end motif sequence have the same identity. In some cases, a sequence adjacent to a sticky end motif in a nucleic acid described herein does not comprise a G or C in the first two positions adjacent to the 3' end of the sticky end motif.

Figure 2:
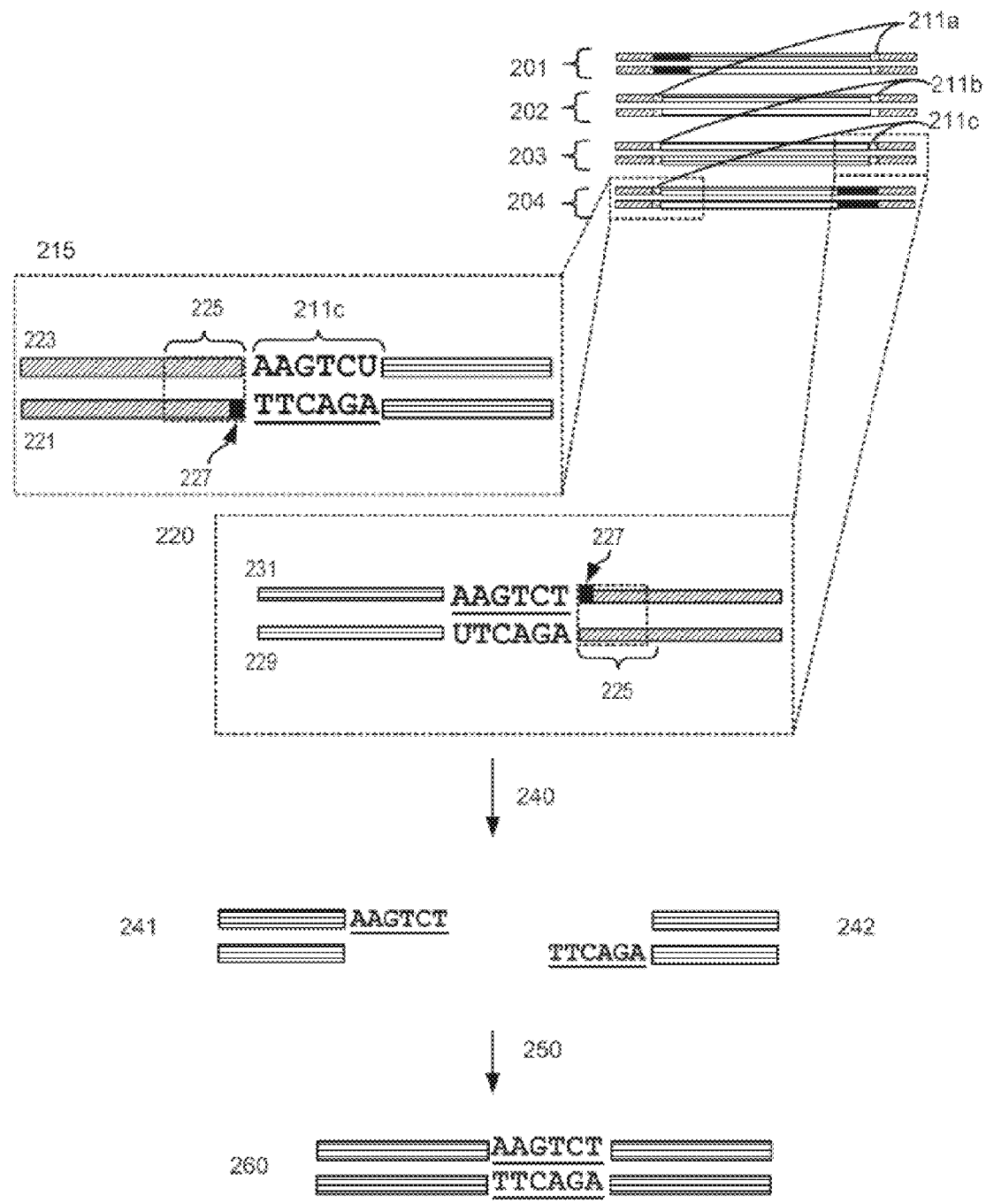
FIG. 2 depicts the assembly of a longer nucleic acid fragment from the ligation of two oligonucleic acid fragments having complementary overhangs and discloses SEQ ID NOS.: 4, 6, 3, 5, 3, 6, 3 and 6, respectively, in order of appearance.

Referring to the figures, FIG. 2 depicts the preparation and annealing of two sticky ends in a plurality of precursor nucleic acid fragments. In FIG. 2, a plurality of fragments spanning a predetermined target nucleic acid sequence is generated for which sticky end motif sequences have been selected (sticky end motifs X, Y, and Z) such that only two fragments will share a particular compatible sticky end. Each precursor fragment comprises target nucleic acid fragment sequence, flanked by sticky end motif sequence ANNNNT (SEQ ID NO.: 2), wherein NNNN are specific to an end pair, and having a U in place of the T at the 3' end of one strand. In alternate embodiments the sequence is GNNNNC (SEQ ID NO.: 17), herein NNNN are specific to an end pair, and having a U in place of the C at the 3' end of one strand.

Another non-limiting depiction of sticky end use is shown in the example workflow of FIG. 4, which generally depicts the assembly of target nucleic acids from precursor nucleic acid fragments via assembly of complementary sticky ends in the precursor fragments. Connecting adaptors of two or more fragments may be synthesized to be flanked by Type II restriction endonuclease sites that are unique to a fragment pair. Compatible ends are ligated and PCR is used to amplify the full length target nucleic acids.

Position-Specific Sticky End Generation

In some cases, methods and compositions described herein use two independent cleavage events that have to occur within a distance that allow for separation of a cleaved end sequence under specified reaction conditions. For example, two different cleaving agents are used that both cut DNA only at a single-strand. In some cases, one or both of the cleaving agents cut outside of its recognition sequence (a "strand-adjacent nicking enzyme"). This allows independency of the process from the actual sequence of the overhangs which are to be assembled at sticky end sites. In some cases, one or more of the cleavage agents recognizes or cleaves at non-canonical bases that are not part of the Watson-Crick base pairs or typical base pairs, including, but not limited to a uracil, a mismatch, and a modified base.

Further provided herein are methods for generation of a sticky end in a double-stranded nucleic acid having a sticky end motif comprises cleaving a first strand of the nucleic acid at a first position adjacent to one end of the sticky end motif and cleaving a second strand of the nucleic acid at a second position adjacent to the other end of the sticky end motif. In some cases, the first and/or second position are defined by their location next to a nicking enzyme recognition sequence. For example, a strand-adjacent nicking enzyme recognitions the nicking enzyme recognition sequence and cleaves a single-strand adjacent to the recognition sequence. In some cases, the first and/or second position are defined by the presence of a non-canonical base, wherein excision and cleavage at the non-canonical base site occurs via one or more nicking enzymes collectively having excision and endonuclease activities. In some cases, two nicks on opposite strands of a nucleic acid are within a short nick-to-nick distance from each other, e.g., a distance equal to or less than 1, 2, 3, 4, 5, 6, 7, 8, 9, 10, 11, 12, 13, 14, or 15 base pairs. A nicking enzyme recognition sequence is positioned such that its cleavage site is at the desired nick-to-nick distance from the other cleavage activity that is used together to create an overhang.

A single-strand of a sticky end motif may be modified with or comprises a non-canonical base positioned directly adjacent to a target nucleic acid sequence. In some cases, a non-canonical base identifies a cleavage site. In an exemplary arrangement, an adaptor sequence comprising a sticky end motif further comprises a nicking enzyme recognition sequence adjacent to the terminal end of the sticky end motif. In this configuration, if the nicking enzyme recognition sequence defines a cleavage site adjacent to the recognition sequence and is located next to the sticky end motif, treatment with a strand-adjacent nicking enzyme introduces a nick on a single-strand between the nicking enzyme recognition sequence and sticky end motif. Examples of non-canonical bases for inclusion in a modified sticky end motif are, without limitation, 5-fluorouracil, 5-bromouracil, 5-chlorouracil, 5-iodouracil, hypoxanthine, xanthine, acetylcytosine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N-6-isopentenyl adenine, 1-methylguanine, 1-methylinosine, 2,2-dimethylguanine, 1-methyladenine, 2-methyladenine, 2-methylguanine, 3-methylcytosine, 5-methylcytosine, 5-ethylcytosine, N6-adenine, N6-methyladenine, N,N-dimethyladenine, 8-bromoadenine, 7-methylguanine, 8-bromoguanine, 8-chloroguanine, 8-aminoguanine, 8-methylguanine, 8-thioguanine, 5-ethyluracil, 5-propyluracil, 5-methylaminomethyluracil, methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, 1-methylpseudouracil, queosine, 2-thiocytosine, 5-methyl-2-thiouracil, 2-thiouracil, 4-thiouracil, 5-hydroxymethyluracil, 5-methyluracil, uracil-5-oxyacetic acid methylester, uracil-S-oxyacetic acid, 5-methyl-2-thiouracil, 3-(3-amino-3-N-2-carboxypropyl)uracil, 5-(2-bromovinyl)uracil, 2-aminopurine, 6-hydroxyaminopurine, 6-thiopurine, and 2,6-diaminopurine.

In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. Examples of modified sugar moieties which can be used to modify nucleosides or nucleotides at any position on their structures include, but are not limited to arabinose, 2-fluoroarabinose, xylose, and hexose, or a modified component of the phosphate backbone, such as phosphorothioate, a phosphorodithioate, a phosphoramidothioate, a pliosphoramidate, a phosphordiamidate, a methylphosphonate, an alkyl phosphotriester, or a formacetal or analog thereof.

A nucleic acid described herein may be treated with a chemical agent, or synthesized using modified nucleotides, thereby creating a modified nucleic acid. In various embodiments, a modified nucleic may is cleaved, for example at the site of the modified base. For example, a nucleic acid may comprise alkylated bases, such N3-methyladenine and N3-methylguanine, which may be recognized and cleaved by an alkyl purine DNA-glycosylase, such as DNA glycosylase I (*E. coli* TAG) or AlkA. Similarly, uracil residues may be introduced site specifically, for example by the use of a primer comprising uracil at a specific site. The modified nucleic acid may be cleaved at the site of the uracil residue, for example by a uracil N-glycosylase. Guanine in its oxidized form, 8-hydroxyguanine, may be cleaved by formamidopyrimidine DNA N-glycosylase. Examples of chemical cleavage processes include without limitation alkylation, (e.g., alkylation of phosphorothioate-modified nucleic acid); cleavage of acid lability of P3'-N5'-phosphoroamidate-containing nucleic acid; and osmium tetroxide and piperidine treatment of nucleic acid.

Nucleic Acid Synthesis and Modification

Methods described herein provide for synthesis of a precursor nucleic acid sequence, or a target fragment sequence thereof, has a length of about or at least about 50, 100, 200, 300, 400, 500, 600, 700, 800, 900, 1000, 2000, 3000, 4000, 5000, 10000, 20000, or 30000 bases. In some cases, a plurality of precursor nucleic acid fragments are prepared with sticky ends, and the sticky ends are annealed and ligated to generate the predetermined target nucleic acid sequence having a base length of about, or at least about, 500, 1000, 2000, 3000, 4000, 5000, 6000, 7000, 8000, 9000, 10000, 15000, 20000, 30000, 50000, or 100000 bases. In some cases, a precursor nucleic acid sequence is assembled with another precursor nucleic acid sequence via annealing and ligation of complementary sticky ends, followed by additional rounds of sticky end generation and assembly with other precursor fragment(s) to generate a long target nucleic acid sequence. In some cases, 2, 3, 4, 5, 6, 7, 8, 9, or 10 rounds of sticky end generation and assembly are performed to generate a long target nucleic acid of predetermined sequence. The precursor nucleic acid fragment or a plurality of precursor nucleic acid fragments may span a predetermined sequence of a target gene, or portion thereof. The precursor nucleic acid fragment or a plurality of precursor nucleic acid fragments may span a vector and a plasmid sequence, or portion thereof. For example, a precursor nucleic acid fragment comprises a sequence of a cloning vector from a plasmid. In some such cases, a cloning vector is generated using de novo synthesis and an assembly method described herein, and is subsequently assembled with a precursor nucleic acid fragment or fragments of a target gene to generate an expression plasmid harboring the target gene. A vector may be a nucleic acid, optionally derived from a virus, a plasmid, or a cell, which comprises features for expression in a host cell, including, for example, an origin of replication, selectable marker, reporter gene, promoter, and/or ribosomal binding site. A host cell includes, without limitation, a bacterial cell, a viral cell, a yeast cell, and a mammalian cell. Cloning vectors useful as precursor nucleic acid fragments include, without limitation, those derived from plasmids, bacteriophages, cosmids, bacterial artificial chromosomes, yeast artificial chromosomes, and human artificial chromosomes.

Provided herein are methods for synthesis of target nucleic acid fragments having an error rate of less than 1/500, 1/1000, 1/10,000 or less compared to a predetermined sequence(s). In some cases, target fragment length is selected in light of the location of desired sticky ends, such that target fragment length varies among fragments in light of the occurrence of desired sticky ends among target fragments. In some cases, target nucleic acid fragments are synthesized to a size of at least 20 but less than 100, 110, 120, 130, 140, 150, 160, 170, 180, 190, 200, 210, 220, 230, 240, 250, 260, 270, 280, 290, 300, 500, 1000, 5000, 10000, or 30000 bases. In some cases, target fragments are synthesized de novo, such as through nonenzymatic nucleic acid synthesis. In some cases, target nucleic acid fragments are synthesized from template nucleic acids, such as templates of nucleic acids that are to be assembled into a single target nucleic acid but which, in some cases, do not naturally occur adjacent to one another.

Through the synthesis of target nucleic acid fragments having at least one indeterminate position, followed by the ligation at sticky ends to adjacent target nucleic acid fragments also having at least one indeterminate position, one can synthesize a target nucleic acid population that comprises a recombinant library of all possible combinations of the base identities at the varying positions. Alternately, at least one base position is partially indeterminate in some cases, such that two or three base alternatives are permitted. In some such cases, target nucleic acid fragments are selected such that only one base varies within a given target nucleic acid fragment, which in turn allows for each position to independently vary in the target nucleic acid library.

Figure 6:
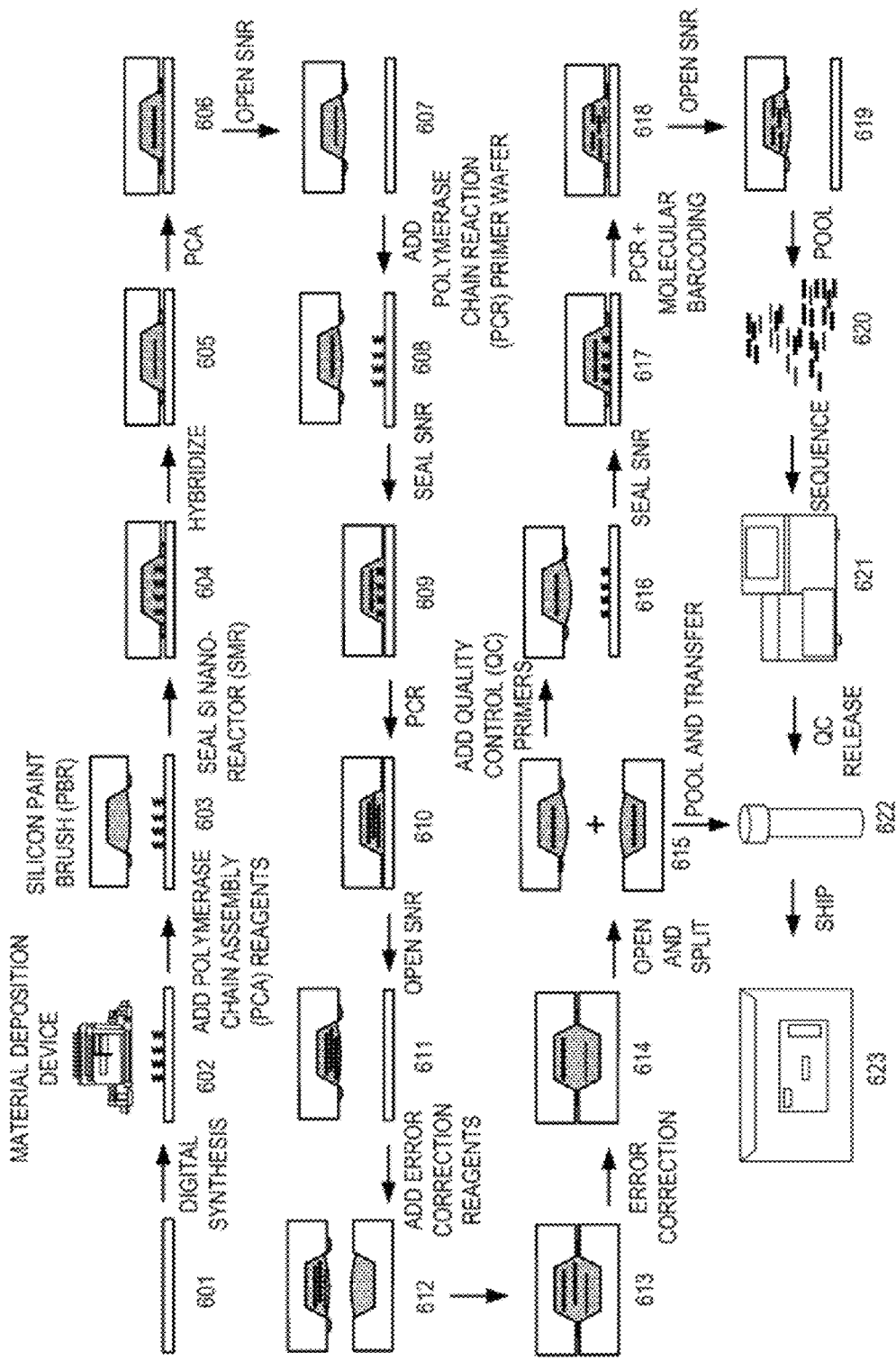
FIG. 6 depicts a diagram of steps demonstrating a process workflow for oligonucleic acid synthesis and assembly.

An example workflow of nucleic acid synthesis is shown in FIG. 6. Methods of synthesis using this workflow are, in some instances, performed to generate a plurality of target nucleic acid fragments, or oligonucleotides thereof, for assembly using sticky end methods described herein. In some cases, oligonucleotides are prepared and assembled into precursor fragments using the methods depicted in FIG. 6. The workflow is divided generally into the following processes: (1) de novo synthesis of a single stranded oligonucleic acid library, (2) joining oligonucleic acids to form larger fragments, (3) error correction, (4) quality control, and (5) shipment. Prior to de novo synthesis, an intended nucleic acid sequence or group of nucleic acid sequences is preselected. For example, a library of precursor nucleic acid fragments is preselected for generation.

In some instances, a structure comprising a surface layer 601 is provided. In the example, chemistry of the surface is functionalized in order to improve the oligonucleic acid synthesis process. Areas of low surface energy are generated to repel liquid while areas of high surface energy are generated to attract liquids. The surface itself may be in the form of a planar surface or contain variations in shape, such as protrusions or nanowells which increase surface area. In the workflow example, high surface energy molecules selected support oligonucleic acid attachment and synthesis.

In step 602 of the workflow example, a device, such as a material deposition device, is designed to release reagents in a step wise fashion such that multiple oligonucleic acids extend from an actively functionalized surface region, in parallel, one residue at a time to generate oligomers with a predetermined nucleic acid sequence. In some cases, oligonucleic acids are cleaved from the surface at this stage. Cleavage includes gas cleavage, e.g., with ammonia or methylamine.

The generated oligonucleic acid libraries are placed in a reaction chamber. In some instances, the reaction chamber (also referred to as "nanoreactor") is a silicon coated well containing PCR reagents lowered onto the oligonucleic acid library 603. Prior to or after the sealing 604 of the oligonucleic acids, a reagent is added to release the oligonucleic acids from the surface. In the exemplary workflow, the oligonucleic acids are released subsequent to sealing of the nanoreactor 605. Once released, fragments of single-stranded oligonucleic acids hybridize in order to span an entire long range sequence of DNA. Partial hybridization 605 is possible because each synthesized oligonucleic acid is designed to have a small portion overlapping with at least one other oligonucleic acid in the pool.

After hybridization, oligonucleic acids are assembled in a PCA reaction. During the polymerase cycles of the PCA reaction, the oligonucleic acids anneal to complementary fragments and gaps are filled in by a polymerase. Each cycle increases the length of various fragments randomly depending on which oligonucleic acids find each other. Complementarity amongst the fragments allows for forming a complete large span of double-stranded DNA 606, in some instances, a fragment of DNA to be assembled into a target nucleic acid.

After PCA is complete, the nanoreactor is separated from the surface 607 and positioned for interaction with a surface having primers for PCR 608. After sealing, the nanoreactor is subject to PCR 609 and the larger nucleic acids are amplified. After PCR 610, the nanochamber is opened 611, error correction reagents are added 612, the chamber is sealed 613 and an error correction reaction occurs to remove mismatched base pairs and/or strands with poor complementarity from the double-stranded PCR amplification products 614. The nanoreactor is opened and separated 615. Error corrected product is next subject to additional processing steps, such as PCR, nucleic acid sorting, and/or molecular bar coding, and then packaged 622 for shipment 623.

In some cases, quality control measures are taken. After error correction, quality control steps include, for example, interaction with a wafer having sequencing primers for amplification of the error corrected product 616, sealing the wafer to a chamber containing error corrected amplification product 617, and performing an additional round of amplification 618. The nanoreactor is opened 619 and the products are pooled 620 and sequenced 621. In some cases, nucleic acid sorting is performed prior to sequencing. After an acceptable quality control determination is made, the packaged product 622 is approved for shipment 623. Alternatively, the product is a library of precursor nucleic acids to be assembled using scar-free assembly methods and compositions described herein.

Provided herein is library of nucleic acids each synthesized with an adaptor sequence comprising a shared primer binding sequence. In some cases, the primer binding sequence is a universal primer binding sequence shared among all primers in a reaction. In some cases, different set of primers are used for generating different final nucleic acids. In some cases, multiple populations of primers each have their own "universal" primer binding sequence that is directed to hybridize with universal primer binding sites on multiple nucleic acids in a library. In such a configuration, different nucleic acids within a population share a universal primer binding site, but differ in other sequence elements. Thus, multiple populations of nucleic acids may be used as a template in primer extension reactions in parallel through the use of different universal primer binding sites. Universal primers may comprise a fusion site sequence that is partially or completely complementary to a sticky end motif of one of the nucleic acids. The combination of a primer binding sequence and the sticky end motif sequence is used to hybridize the primer to template nucleic acids. In some cases, primers and/or adaptor sequences further comprise a recognition sequence for a cleavage agent, such as a nicking enzyme. In some cases, primers and/or primer binding sequences in an adaptor sequence further comprise a recognition sequence for a cleavage agent, such as a nicking enzyme. In some cases, a nicking enzyme recognition sequence is introduced to extension products by a primer.

Primer extension may be used to introduce a sequence element other than a typical DNA or RNA Watson-Crick base pair, including, without being limited to, a uracil, a mismatch, a loop, or a modified nucleoside; and thus creates a non-canonical base pair in a double-stranded target nucleic acid or fragment thereof. Primers are designed to contain such sequences in a way that still allows efficient hybridization that leads to primer extension. Such non-Watson-Crick sequence elements may be used to create a nick on one strand of the resulting double-stranded nucleic acid amplicon. In some cases, a primer extension reaction is used to produce extension products incorporating uracil into a precursor nucleic acid fragment sequence. Such primer extension reactions may be performed linearly or exponentially. In some cases, a polymerase in a primer extension reaction is a 'Family A' polymerase lacking 3'-5' proofreading activity. In some cases, a polymerase in a primer extension reaction is a Family B high fidelity polymerase engineered to tolerate base pairs comprising uracil. In some cases, a polymerase in a primer extension reaction is a Kappa Uracil polymerase, a FusionU polymerase, or a Pfu turbo polymerase as commercially available.

Nicking Enzyme Recognition Sequences and Cleavage Sites

The generation of an overhang described herein in a double-stranded nucleic acid comprises may create two independent single-stranded nicks at an end of the double-stranded nucleic acid. In some cases, the two independent single-stranded nicks are generated by two cleavage agents having cleavage activities independent from each other. In some cases, a nick is created by including a recognition site for a cleavage agent, for example in an adaptor region or fusion site. In some cases, a cleavage agent is a nicking endonuclease using a nicking endonuclease recognition sequence or any other agent that produces a site-specific single-stranded cut. For example, a mismatch repair agent that creates a gap at the site of a mismatched base-pair, or a base excision system that creates a gap at the site of a recognized nucleoside, such as a deoxy-uridine, is used to create a single-stranded cut. In some cases, a deoxy-uridine is a non-canonical base in a non-canonical base pair formed with a deoxy-adenine, a deoxy-guanine, or a deoxy-thymine. In some cases, for example, when using a uracil containing primer in a nucleic acid extension reaction, a nucleic acid comprises a deoxy-uridine/deoxy-adenine base pair. For example a glycosylase, such as UDG, alone or in combination with an AP endonuclease, such as endonuclease VIII, is used to excise uracil and create a gap. In some cases, a second nick is created similarly using any suitable single-stranded site-specific cleavage agent; wherein the second nick is created at a site not directly across from the first nick in the double-stranded nucleic acid. Such pairs of staggered nicks, when in proximity to each other and under appropriate reaction conditions, cause a sticky end when parts of the original nucleic acid melt away from each other. In various embodiments, one or more of the cleavage sites are situated apart from the sequence of the fusion site.

Two nicks in a double-stranded nucleic acid may be created such that the resulting overhang is co-extensive with the span of a sticky end site. For example, a first nick is created at the juncture between sticky end site and adaptor region at one end of a nucleic acid; and a second nick is created at the other end of the sticky end site. Thus, only one strand along a sticky end site is kept at the end of a nucleic acid along the entire sticky end sequence, while the other is cut off. A mixture of enzymatic uracil excision activity and nicking endonuclease activity may be provided in a mixture of engineered fragments. In some cases, a strand-adjacent nicking enzyme is provided, such that sticky ends that reanneal to their cleaved terminal ends and are re-ligated across a single-strand will be re-subjected to single-strand nicking due to the reconstitution of the strand-adjacent nicking site.

Overhangs of various sizes are prepared by adjusting the distance between two nicks on opposite strands of the end of a double-stranded nucleic acid. In some cases, the distance or the length of an overhang is equal to or less than 15, 14, 13, 12, 11, 10, 9, 8, 7, 6, 5, 4, 3, or 2 bases. Overhangs may be 3' or 5' overhangs. In various embodiments, the cleavage site of a cleavage agent is a fixed distance away from its recognition site. In some cases, the fixed distance between a cleavage agent's cleavage site and recognition site is more than or equal to about 1, 2, 3, 4, 5, 6, 7, 8, 9, 10, 11, 12, 13, 14, 15 bases or more. In some cases, the fixed distance between a cleavage agent's cleavage site and recognition site is 2-10 bases, 3-9 bases, or 4-8 bases. The cleavage site of a cleaving agent may be outside of its recognition site, for example, it is adjacent to its recognition site and the agent is a strand-adjacent nicking enzyme. In some case, the recognition site of a cleavage agent is not cleaved.

A double-stranded nucleic acid disclosed herein may be modified to comprise a non-canonical base. As a non-limiting example, a nucleic acid fragment having a sticky end motif such as A ($N^x$) T (SEQ ID NO.: 1) or G ($N^x$) C (SEQ ID NO.: 16) is prepared. In some cases, the fragment further comprises a recognition site for a single-strand cleavage agent, such as a nicking endonuclease, having a cleavage site immediately adjacent to the last base in the sticky end motif sequence. Alternatively, the recognition site is introduced by a primer in a nucleic acid extension reaction using a strand of the fragment comprising the sticky end motif as a template. For example, the recognition site is appended to the end of the fragment in an adaptor region. In a non-limiting example, a nucleic acid extension reaction using the strand of the fragment comprising the sticky end motif, such as A ($N^x$) T (SEQ ID NO.: 1) or G ($N^x$) C (SEQ ID NO.: 16), as a template is primed with a primer comprising a sticky end sequence comprising a non-canonical base substitution. For a sticky end motif of A ($N^x$) T (SEQ ID NO.: 1) in a template, one such primer comprises the sequence A ($N^x$)' U (SEQ ID NO.: 18), wherein ($N^x$)' is partially or completely reverse complementary to ($N^x$). For a sticky end motif of A ($N^x$) T (SEQ ID NO.: 1) in a template, one such primer comprises the sequence A ($N^x$) U (SEQ ID NO.: 19). In some cases, the A ($N^x$)' U (SEQ ID NO.: 18) and/or A ($N^x$) U (SEQ ID NO.: 19) sequence on the primer is located at the very 3' end of the primer. A plurality of such primers each having a sequence of A ($N^x$)' U (SEQ ID NO.: 18) and/or A ($N^x$) U (SEQ ID NO.: 19) corresponding to a sequence of A ($N^x$) T in one strand of a fragment may be used to perform a nucleic acid extension reaction. The exemplary sequences described have a sticky end motif comprising a first A or G and a terminal T or C prior to non-canonical base in corporation. However, any sticky end motif sequence is useful with the methods described herein.

Libraries

Provided herein are fragment libraries comprising n double-stranded precursor nucleic acids fragments. In some cases, each double-stranded nucleic acid precursor fragment of the n double-stranded nucleic acid fragments comprises a first nicking endonuclease recognition site, a first fusion site, a variable insert of predetermined fragment sequence, a second fusion site, and a second nick enzyme recognition site, optionally in that order. In some cases, the first fusion site comprises or is a first sticky end motif and the second fusion site comprises or is a second sticky end motif. In some instances, the fist fusion site has the sequence of 5'-A ($N^x$)$_{i,1}$ U-3' (SEQ ID NO.: 13) in the first strand, wherein denotes $N^x$ x bases or nucleosides and the subscript "$_{i,1}$" in ($N^x$)$_{i,1}$ denotes the first strand of the ith fragment. In some cases, the second fusion site has the sequence of 5'-A ($N^x$)$_{i,2}$U-3' (SEQ ID NO.: 14) in the second strand, wherein denotes $N^x$ x bases or nucleosides and the subscript "$_{i,2}$" in ($N^x$)$_{i,2}$ denotes the second strand of the ith fragment. In some instances ($N^x$)$_{i,2}$ is completely or partially reverse complementary to ($N^x$)$_{i+1,1}$ in the first strand of the i+1'th fragment. Each $N^x$ found in the fusion site sequences are the same or different that the $N^x$ in any other fusion site sequence found within the fragment library. In some cases, the first nicking endonuclease recognition site is positioned such that there is a corresponding cleavage site immediately 3' of the first fusion site in the second strand and the second nicking endonuclease recognition site is positioned such that there is a corresponding cleavage site immediately 3' of the second fusion site in the first strand.

A fragment library may comprise a starter DNA fragment comprising a variable insert, a second fusion site, and a second nick enzyme recognition site. In some cases, the second fusion site of the starter DNA fragment comprises a sequence of 5'-A ($N^x$)$_{s,2}$ U-3' (SEQ ID NO.: 20), wherein the subscript "$_{s,2}$" in ($N^x$)$_{s,2}$ denotes the second strand of the starter fragment and ($N^x$)$_{s,2}$ is reverse complementary to ($N^x$)$_{1,1}$ in one of the fusion sites of the first nucleic acid fragment in the library. Similarly, the fragment library may also comprise a finishing DNA fragment comprising a first nicking endonuclease recognition site, a first fusion site, and a variable insert. In some cases, the first fusion site comprises a sequence of 5'-A ($N^x$)$_{f,1}$ U-3'(SEQ ID NO.: 21), wherein the subscript "$_{f,1}$" in ($N^x$)$_{f,1}$ denotes the first strand of the finishing fragment And ($N^x$)$_{f,1}$ is reverse complementary to ($N^x$)$_{n,2}$ in one of the fusion sites of the nth nucleic acid fragment in the library. In some cases, the first and/or the second nicking endonuclease recognition sites are the same in all the fragments in the fragment library. In various embodiments, the fragment library comprises about or at least about 2, 3, 4, 5, 6, 7, 8, 9, 10, 11, 12, 13, 14, 15, 20, 25, 30, 35, 40, 45, 50, 60, 75, 100, 125, 150, 200, 250, 500, or more nucleic acid fragments. In some instances, the fragment library comprises 2-75 fragments, 4-125 fragments, or 5-10 fragments.

Further described herein is a primer library of n primers. Each primer within the library may comprise a recognition sequence such a nicking endonuclease recognition sequence, and a fusion sequence comprising a sticky end motif. For example, a sticky end motif having the sequence 5'-A $(N^x)_i$ U-3' (SEQ ID NO.: 15). In some cases, the recognition sequence is positioned 5' of the fusion site sequence. In some cases, the recognition sequence is positioned such that the recognition site in a primer is capable of generating a corresponding cleavage site in a reverse complimentary DNA strand 3' of a first fusion site in the reverse complementary DNA strand, if the primer were hybridized to the reverse complementary DNA strand such that the fusion sequence hybridizes to the first fusion site in the reverse complementary DNA strand. In various aspects, a primer library described herein comprises about or at least about 2, 3, 4, 5, 6, 7, 8, 9, 10, 11, 12, 13, 14, 15, 20, 25, 30, 35, 40, 45, 50, 60, 75, 100, 125, 150, 200, 250, 500, or more primers.

Cleavage Agents

Provided herein are methods where two or more independent cleaving agents are selected to generate single-stranded cleavage on opposite strands of a double-stranded nucleic acid. As used herein, "nick" generally refers to enzymatic cleavage of only one strand of a double-stranded nucleic acid at a particular region, while leaving the other strand intact, regardless of whether one or more bases are removed. In some cases, one or more bases are removed while in other cases no bases are removed and only phosphodiester bonds are broken. In some instances, such cleavage events leave behind intact double-stranded regions lacking nicks that are a short distance apart from each other on the double-stranded nucleic acid, for example a distance of about or at least about 1, 2, 3, 4, 5, 6, 7, 8, 9, 10, 11, 12, 13, 14, 15 bases or more. In some cases, the distance between the intact double-stranded regions is equal to or less than 15, 14, 13, 12, 11, 10, 9, 8, 7, 6, 5, 4, 3, or 2 bases. In some instances, the distance between the intact double-stranded regions is 2 to 10 bases, 3 to 9 bases, or 4 to 8 bases.

Cleavage agents used in methods described herein may be selected from nicking endonucleases, DNA glycosylases, or any single-stranded cleavage agents described in further detail elsewhere herein. Enzymes for cleavage of single-stranded DNA may be used for cleaving heteroduplexes in the vicinity of mismatched bases, D-loops, heteroduplexes formed between two strands of DNA which differ by a single base, an insertion or deletion. Mismatch recognition proteins that cleave one strand of the mismatched DNA in the vicinity of the mismatch site may be used as cleavage agents. Nonenzymatic cleaving may also be done through photo-degradation of a linker introduced through a custom oligonucleotide used in a PCR reaction.

Provided herein are fragments designed and synthesized such that the inherent cleavage sites are utilized in the preparation of fragments for assembly. For instance, these inherent cleavage sites are supplemented with a cleavage site that is introduced, e.g., by recognition sites in adaptor sequences, by a mismatch, by a uracil, and/or by an unnatural nucleoside. In various embodiments, described herein is a plurality of double stranded nucleic acids such as dsDNA, comprising an atypical DNA base pair comprising a non-canonical base in a fusion site and a recognition site for a single-strand cleaving agent. Compositions according to embodiments described herein, in many cases, comprise two or more cleaving agents. In some cases, a first cleaving agent has the atypical DNA base pair as its recognition site and the cleaving agent cleaves a single-strand at or a fixed distance away from the atypical DNA base pair. In some cases, a second cleaving agent has an independent single-strand cleaving and/or recognition activity from the first cleaving agent. In some cases, the nucleic acid molecules in the composition are such that the recognition site for the second single-strand cleaving agent is not naturally adjacent to the fusion site or the remainder of the nucleic acid in any of the plurality of double stranded nucleic acids in the composition. In some instances, the cleavage sites of two cleavage agents are located on opposite strands.

Type II Enzymes

Provided herein are methods and compositions described herein use a Type II restriction endonuclease in as a cleavage agent. Type II enzymes cleave within or at short specific distances from a recognition site. There are a variety of different type II enzymes known in the art, many of which differ in the sequence they recognize. Type II restriction endonucleases comprise many sub-types with varying activities. Exemplary Type II restriction endonucleases include, without limitation, Type IIP, Type IIF, Type IIB (e.g. BcgI and BpII), Type IIE (e.g. NaeI), and Type IIM (DpnI) restriction endonucleases. The most common Type II enzymes are those like HhaI, HindIII, and NotI that cleave DNA within their recognition sequences. Many recognize DNA sequences that are symmetric, because, without being bound by theory, they bind to DNA as homodimers, but a few, (e.g., BbvCI: CCTCAGC (SEQ ID NO.: 22)) recognize asymmetric DNA sequences, because, without being bound by theory, they bind as heterodimers. Some enzymes recognize continuous sequences (e.g., EcoRI: GAATTC (SEQ ID NO.: 23)) in which the two half-sites of the recognition sequence are adjacent, while others recognize discontinuous sequences (e.g., BglI: GCCNNNNNGGC (SEQ ID NO.: 24)) in which the half-sites are separated. Using this type, a 3'-hydroxyl on one side of each cut and a 5'-phosphate on the other may be created upon cleavage.

The next most common Type II enzymes, usually referred to as "Type IIS" are those like FokI and AlwI that cleave outside of their recognition sequence to one side. Type IIS enzymes recognize sequences that are continuous and asymmetric. Type IIS restriction endonucleases (e.g. FokI) cleave DNA at a defined distance from their non-palindromic asymmetric recognition sites. These enzymes may function as dimers. Type IIS enzymes typically comprise two distinct domains, one for DNA binding, and the other for DNA cleavage. Type IIA restriction endonucleases recognize asymmetric sequences but can cleave symmetrically within the recognition sequences (e.g. BbvCI cleaves 2 based downstream of the 5'-end of each strand of CCTCAGC (SEQ ID NO.: 25)). Similar to Type IIS restriction endonucleases, Type IIT restriction enzymes (e.g., Bpu10I and Bs1I) are composed of two different subunits. Type IIG restriction enzymes, the third major kind of Type II enzyme, are large, combination restriction-and-modification enzymes, Type IIG restriction endonucleases (e.g. Eco57I) do have a single subunit, like classical Type II restriction enzymes. The two enzymatic activities typically reside in the same protein chain. These enzymes cleave outside of their recognition sequences and can be classified as those that recognize continuous sequences (e.g., AcuI: CTGAAG (SEQ ID NO.: 26)) and cleave on just one side; and those that recognize discontinuous sequences (e.g., BcgI: CGANNNNNNTGC (SEQ ID NO.: 27)) and cleave on both sides releasing a small fragment containing the recognition sequence. When these enzymes bind to their substrates, they may switch into either restriction mode to cleave the DNA, or modification mode to methylate it.

Type III enzymes are also large combination restriction-and-modification enzymes. They cleave outside of their recognition sequences and require two such sequences in opposite orientations within the same DNA molecule to accomplish cleavage. Type IV enzymes recognize modified DNA, e.g. methylated, hydroxymethylated and glucosyl-hydroxymethylated DNA and are exemplified by the McrBC and Mrr systems of *E. coli*.

Some naturally occurring and recombinant endonucleases make single-strand breaks. These nicking endonucleases (NEases) typically recognize non-palindromes. They can be bona fide nicking enzymes, such as frequent cutter Nt.CviPII and Nt.CviQII, or rare-cutting homing endonucleases (HEases) I-BasI and I-HmuI, both of which recognize a degenerate 24-bp sequence. As well, isolated large subunits of heterodimeric Type IIS REases such as BtsI, BsrDI and BstNBI/BspD6I display nicking activity.

Thus, properties of restriction endonucleases that make double-strand cuts may be retained by engineering variants of these enzymes such that they make single-strand breaks. In various embodiments, recognition sequence-specific nicking endonucleases are used as cleavage agents that cleave only a single-strand of double-stranded DNA at a cleavage site. Nicking endonucleases useful in various embodiments of methods and compositions described herein include Nb.BbvCI, Nb.BsmI, Nb.BsrDI, Nb.BtsI, Nt.AlwI, Nt.BbvCI, Nt.BsmAI, Nt.BspQI, Nt.BstNBI, and Nt.CviPII, used either alone or in various combinations. In various embodiments, nicking endonucleases that cleave outside of their recognition sequence, e.g. Nb.BsrDI, Nb.BtsI, Nt.AlwI, Nt.BsmAI, Nt.BspQI, Nt.BstNBI, and Nt.CviPII, are used. In some instances, nicking endonucleases that cut within their recognition sequences, e.g. Nb.BbvCI, Nb.BsmI, or Nt.BbvCI are used. Recognition sites for the various specific cleavage agents used herein, such as the nicking endonucleases, comprise a specific nucleic acid sequence. The nickase Nb.BbvCI (New England Biolabs, Ipswich, Mass. nicks at the following cleavage site with respect to its recognition site (with "|" specifying the nicking (cleavage) site and "N" representing any nucleoside, e.g. one of C, A, G or T):

```
                                        (SEQ ID NO.: 28)
5'...CCTCA GC...3'

(SEQ ID NO.: 29)
3'...GGAGT|CG...5'
```

The nickase Nb.BsmI (New England Biolabs, Ipswich, Mass.) nicks at the following cleavage site with respect to its recognition site:

```
                                        (SEQ ID NO.: 30)
5'...GAATGCN...3'

(SEQ ID NO.: 31)
3'...CTTAC|GN...5'
```

The nickase Nb.BsrDI (New England Biolabs, Ipswich, Mass.) nicks at the following cleavage site with respect to its recognition site:

```
                                        (SEQ ID NO.: 32)
5'...GCAATGNN...3'

(SEQ ID NO.: 33)
3'...CGTTAC|NN...5'
```

The nickase Nb.BtsI (New England Biolabs, Ipswich, Mass.) nicks at the following cleavage site with respect to its recognition site:

```
                                        (SEQ ID NO.: 34)
5'...GCAGTGNN...3'

(SEQ ID NO.: 35)
3'...CGTCAC|NN...5'
```

The nickase Nt.AlwI (New England Biolabs, Ipswich, Mass.) nicks at the following cleavage site with respect to its recognition site:

```
                                        (SEQ ID NO.: 36)
5'...GGATCNNNN|N...3'

(SEQ ID NO.: 37)
3'...CCTAGNNNNN...5'
```

The nickase Nt.BbvCI (New England Biolabs, Ipswich, Mass.) nicks at the following cleavage site with respect to its recognition site:

```
                                        (SEQ ID NO.: 38)
5'...CC|TCAGC...3'

(SEQ ID NO.: 39)
3'...GGAGTCG...5'
```

The nickase Nt.BsmAI (New England Biolabs, Ipswich, Mass.) nicks at the following cleavage site with respect to its recognition site:

```
                                        (SEQ ID NO.: 40)
5'...GTCTCN|N...3'

(SEQ ID NO.: 41)
3'...CAGAGNN...5'
```

The nickase Nt.BspQI (New England Biolabs, Ipswich, Mass.) nicks at the following cleavage site with respect to its recognition site:

```
                                        (SEQ ID NO.: 42)
5'...GCTCTTCN|...3'

(SEQ ID NO.: 43)
3'...CGAGAAGN...5'
```

The nickase Nt.BstNBI (New England Biolabs, Ipswich, Mass.) nicks at the following cleavage site with respect to its recognition site:

```
                                        (SEQ ID NO.: 44)
5'...GAGTCNNNN|N...3'

(SEQ ID NO.: 45)
3'...CTCAGNNNNN...5'
```

The nickase Nt.CviPII (New England Biolabs, Ipswich, Mass.) nicks at the following cleavage site with respect to its recognition site (wherein D denotes A or G or T and wherein H denotes A or C or T:

5'...|CCD...3' (SEQ ID NO.: 46)

3'...GGH...5' (SEQ ID NO.: 47)

Non-Canonical Base Recognizing Enzymes

A non-canonical base and/or a non-canonical base pair in a sticky end motif and/or adaptor sequence may be recognized by an enzyme for cleavage at its 5' or 3' end. In some instances, the non-canonical base and/or non-canonical base pair comprises a uracil base. In some cases, the enzyme is a DNA repair enzyme. In some cases, the base and/or non-canonical base pair is recognized by an enzyme that catalyzes a first step in base excision, for example, a DNA glycosylase. A DNA glycosylase is useful for removing a base from a nucleic acid while leaving the backbone of the nucleic acid intact, generating an apurinic or apyrimidinic site, or AP site. This removal is accomplished by flipping the base out of a double-stranded nucleic acid followed by cleavage of the N-glycosidic bond.

The non-canonical base or non-canonical base pair may be recognized by a bifunctional glycosylase. In this case, the glycosylase removes a non-canonical base from a nucleic acid by N-glycosylase activity. The resulting apurinic/apyrimidinic (AP) site is then incised by the AP lyase activity of bifunctional glycosylase via (β-elimination of the 3' phosphodiester bond.

The glycosylase and/or DNA repair enzyme may recognize a uracil or a non-canonical base pair comprising uracil, for example U:G and/or U:A. Nucleic acid base substrates recognized by a glycosylase include, without limitation, uracil, 3-meA (3-methyladenine), hypoxanthine, 8-oxoG, FapyG, FapyA, Tg (thymine glycol), hoU (hydroxyuracil), hmU (hydroxymethyluracil), fU (formyluracil), hoC (hydroxycytosine), fC (formylcytosine), oxidized base, alkylated base, deaminated base, methylated base, and any non-canonical nucleobase provided herein or known in the art. In some cases, the glycosylase and/or DNA repair enzyme recognizes oxidized bases such as 2,6-diamino-4-hydroxy-5-formamidopyrimidine (FapyG) and 8-oxoguanine (8-oxo). Glycosylases and/or DNA repair enzymes which recognize oxidized bases include, without limitation, OGG1 (8-oxoG DNA glycosylase 1) or E. coli Fpg (recognizes 8-oxoG:C pair), MYH (MutY homolog DNA glycosylase) or E. coli MutY (recognizes 8-oxoG:A), NEIL1, NEIL2 and NEIL3. In some cases, the glycosylase and/or DNA repair enzyme recognizes methylated bases such as 3-methyladenine. An example of a glycosylase that recognizes methylated bases is E. coli AlkA or 3-methyladenine DNA glycosylase II, Mag1 and MPG (methylpurine glycosylase). Additional non-limiting examples of glycosylases include SMUG1 (single-strand specific monofunctional uracil DNA glycosylase 1), TDG (thymine DNA glycosylase), MBD4 (methyl-binding domain glycosylase 4), and NTHL1 (endonuclease III-like 1). Exemplary DNA glycosylases include, without limitation, uracil DNA glycosylases (UDGs), helix-hairpin-helix (HhH) glycosylases, 3-methylpurine glycosylase (MPG) and endonuclease VIII-like (NEIL) glycosylases. Helix-hairpin-helix (HhH) glycosylases include, without limitation, Nth (homologs of the E. coli EndoIII protein), OggI (8-oxoG DNA glycosylase I), MutY/Mig (A/G-mismatch-specific adenine glycosylase), AlkA (alkyladenine-DNA glycosylase), MpgII (N-methylpurine-DNA glycosylase II), and OggII (8-oxoG DNA glycosylase II). Exemplary 3-methyl-puring glycosylases (MPGs) substances include, in non-limiting examples, alkylated bases including 3-meA, 7-meG, 3-meG and ethylated bases. Endonuclease VIII-like glycosylase substrates include, without limitation, oxidized pyrimidines (e.g., Tg, 5-hC, FaPyA, PaPyG), 5-hU and 8-oxoG.

Exemplary uracil DNA glycosylases (UDGs) include, without limitation, thermophilic uracil DNA glycosylases, uracil-N glycosylases (UNGs), mismatch-specific uracil DNA glycosylases (MUGs) and single-strand specific monofunctional uracil DNA glycosylases (SMUGs). In non-limiting examples, UNGs include UNG1 isoforms and UNG2 isoforms. In non-limiting examples, MUGs include thymidine DNA glycosylase (TDG). A UDG may be active against uracil in ssDNA and dsDNA.

The non-canonical base pair included in a fragment disclosed herein is a mismatch base pair, for example a homopurine pair or a heteropurine pair. In some cases, a primer described herein comprises one or more bases which form a mismatch base pair with a base of a target nucleic acid or with a base of an adaptor sequence connected to a target nucleic acid. In some cases, an endonuclease, exonuclease, glycosylase, DNA repair enzyme, or any combination thereof recognizes the mismatch pair for subsequent removal and cleavage. For example, the TDG enzyme is capable of excising thymine from G:T mismatches. In some cases, the non-canonical base is released from a dsDNA molecule by a DNA glycosylase resulting in an abasic site. This abasic site (AP site) is further processed by an endonuclease which cleaves the phosphate backbone at the abasic site. Endonucleases included in methods herein may be AP endonucleases. For example, the endonuclease is a class I or class II AP endonuclease which incises DNA at the phosphate groups 3' and 5' to the baseless site leaving 3' OH and 5' phosphate termini. The endonuclease may also be a class III or class IV AP endonuclease which cleaves DNA at the phosphate groups 3' and 5' to the baseless site to generate 3' phosphate and 5' OH. In some cases, an endonuclease cleaving a fragment disclosed herein is an AP endonuclease which is grouped in a family based on sequence similarity and structure, for example, AP endonuclease family 1 or AP endonuclease family 2. Examples of AP endonuclease family 1 members include, without limitation, E. coli exonuclease III, S. pneumoniae and B. subtilis exonuclease A, mammalian AP endonuclease 1 (AP1), Drosophila recombination repair protein 1, Arabidopsis thaliana apurinic endonuclease-redox protein, Dictyostelium DNA-(apurinic or apyrimidinic site) lyase, enzymes comprising one or more domains thereof, and enzymes having at least 75% sequence identity to one or more domains or regions thereof. Examples of AP endonuclease family 2 members include, without limitation, bacterial endonuclease IV, fungal and Caenorhabditis elegans apurinic endonuclease APN1, Dictyostelium endonuclease 4 homolog, Archaeal probable endonuclease 4 homologs, mimivirus putative endonuclease 4, enzymes comprising one or more domains thereof, and enzymes having at least 75% sequence identity to one or more domains or regions thereof. Exemplary, endonucleases include endonucleases derived from both Prokaryotes (e.g., endonuclease IV, RecBCD endonuclease, T7 endonuclease, endonuclease II) and Eukaryotes (e.g., Neurospora endonuclease, S1 endonuclease, P1 endonuclease, Mung bean nuclease I, Ustilago nuclease). In some case, an endonuclease functions as both a glycosylase and an AP-lyase. The endonuclease may be endonuclease VIII. In some cases, the endonuclease is S1 endonuclease. In some instances, the endonuclease is endonuclease III. The endonuclease may be a endonuclease IV. In some case, an endonuclease is a protein comprising an endonuclease domain having endonuclease activity, i.e., cleaves a phosphodiester bond.

Provided herein are methods where a non-canonical base is removed with a DNA excision repair enzyme and endonuclease or lyase, wherein the endonuclease or lyase activity is optionally from an excision repair enzyme or a region of the excision repair enzyme. Excision repair enzymes include, without limitation, Methyl Purine DNA Glycosylase (recognizes methylated bases), 8-Oxo-GuanineGlycosylase 1 (recognizes 8-oxoG:C pairs and has lyase activity), Endonuclease Three Homolog 1 (recognizes T-glycol, C-glycol, and formamidopyrimidine and has lyase activity), inosine, hypoxanthine-DNA glycosylase; 5-Methylcytosine, 5-Methylcytosine DNA glycosylase; Formamidopyrimidine-DNA-glycosylase (excision of oxidized residue from DNA: hydrolysis of the N-glycosidic bond (DNA glycosylase), and beta-elimination (AP-lyase reaction)). In some cases, the DNA excision repair enzyme is uracil DNA glycosylase. DNA excision repair enzymes include also include, without limitation, Aag (catalyzes excision of 3-methyladenine, 3-methylguanine, 7-methylguanine, hypoxanthine, 1,N6-ethenoadenine), endonuclease III (catalyzes excision of cis- and trans-thymine glycol, 5,6-dihydrothymine, 5,6-dihydroxydihydrothymine, 5-hydroxy-5-methylhydantoin, 6-hydroxy-5,6-dihydropyrimidines, 5-hydroxycytosine and 5-hydroxyuracil, 5-hydroxy-6-hydrothymine, 5,6-dihydrouracil, 5-hydroxy-6-hydrouracil, AP sites, uracil glycol, methyltartronylurea, alloxan), endonuclease V (cleaves AP sites on dsDNA and ssDNA), Fpg (catalyzes excision of 8-oxoguanine, 5-hydroxycytosine, 5-hydroxyuracil, aflatoxin-bound imidazole ring-opened guanine, imidazole ring-opened N-2-aminofluorene-C8-guanine, open ring forms of 7-methylguanine), and Mug (catalyzes the removal of uracil in U:G mismatches in double-stranded oligonucleic acids, excision of 3, N4-ethenocytosine (eC) in eC:G mismatches in double-, or single-stranded oligonucleic acids). Non-limiting DNA excision repair enzymes are listed in Curr Protoc Mol Biol. 2008 October; Chapter 3:Unit 3.9. DNA excision repair enzymes, such as endonucleases, may be selected to excise a specific non-canonical base. As an example, endonuclease V, *T. maritima* is a 3'-endonuclease which initiates the removal of deaminated bases such as uracil, hypoxanthine, and xanthine. In some cases, a DNA excision repair enzyme having endonuclease activity functions to remove a modified or non-canonical base from a strand of a dsDNA molecule without the use of an enzyme having glycosylase activity.

In some cases, a DNA excision repair enzyme ("DNA repair enzyme") comprises glycosylase activity, lyase activity, endonuclease activity, or any combination thereof. In some cases, one or more DNA excision repair enzymes are used in the methods described herein, for example one or more glycosylases or a combination of one or more glycosylases and one or more endonucleases. As an example, Fpg (formamidopyrimidine [fapy]-DNA glycosylase), also known as 8-oxoguanine DNA glycosylase, acts both as a N-glycosylase and an AP-lyase. The N-glycosylase activity releases a non-canonical base (e.g., 8-oxoguanine, 8-oxoadenine, fapy-guanine, methy-fapy-guanine, fapy-adenine, aflatoxin $B_1$-fapy-guanine, 5-hydroxy-cytosine, 5-hydroxyuracil) from dsDNA, generating an abasic site. The lyase activity then cleaves both 3' and 5' to the abasic site thereby removing the abasic site and leaving a 1 base gap or nick. Additional enzymes which comprise more than enzymatic activities include, without limitation, endonuclease III (Nth) protein from *E. coli* (N-glycosylase and AP-lyase) and Tma endonuclease III (N-glycosylase and AP-lyase). For a list of DNA repair enzymes having lyase activity, see the New England BioLabs® Inc. catalog.

Provided herein are methods where mismatch endonucleases are used to nick DNA in the region of mismatches or damaged DNA, including but not limited to T7 Endonuclease I, *E. coli* Endonuclease V, T4 Endonuclease VII, mung bean nuclease, Cel-1 endonuclease, *E. coli* Endonuclease IV and UVDE. Cel-1 endonuclease from celery and similar enzymes, typically plant enzymes, exhibit properties that detect a variety of errors in double-stranded nucleic acids. For example, such enzymes can detect polynucleotide loops and insertions, detect mismatches in base pairing, recognize sequence differences in polynucleotide strands between about 100 bp and 3 kb in length and recognize such mutations in a target polynucleotide sequence without substantial adverse effects of flanking DNA sequences.

Provided herein are methods where one or more non-canonical bases are excised from a dsDNA molecule which is subsequently treated with an enzyme comprising exonuclease activity. In some cases, the exonuclease comprises 3' DNA polymerase activity. Exonucleases include those enzymes in the following groups: exonuclease I, exonuclease II, exonuclease III, exonuclease IV, exonuclease V, exonuclease VI, exonuclease VII, and exonuclease VIII. In some cases, an exonuclease has AP endonuclease activity. In some cases, the exonuclease is any enzyme comprising one or more domains or amino acid regions suitable for cleaving nucleotides from either 5' or 3' end or both ends, of a nucleic acid chain. Exonucleases include wild-type exonucleases and derivatives, chimeras, and/or mutants thereof. Mutant exonucleases include enzymes comprising one or more mutations, insertions, deletions or any combination thereof within the amino acid or nucleic acid sequence of an exonuclease.

Provided herein are methods where a polymerase is provided to a reaction comprising an enzyme treated dsDNA molecule, wherein one or more non-canonical bases of the dsDNA molecule has been excised, for example, by treatment with one or more DNA repair enzymes. In some cases, the DNA product has been treated with a glycosylase and endonuclease to remove a non-canonical base. In some cases, one or more nucleotides (e.g., dNTPs) are provided to a reaction comprising the treated dsDNA molecule and the polymerase. In some instances, the DNA product has been treated with a UDG and endonuclease VIII to remove at least one uracil. In some cases, one or more nucleotides (e.g., dNTPs) are provided to a reaction comprising the treated dsDNA molecule and the polymerase.

DNA Repair Enzymes

Provided herein are methods where a site-specific base excision reagents comprising one or more enzymes are used as cleavage agents that cleave only a single-strand of double-stranded DNA at a cleavage site. A number of repair enzymes are suitable alone or in combination with other agents to generate such nicks. An exemplary list of repair enzymes in provided in Table 1. Homologs or non-natural variants of the repair enzymes, including those in Table 1, are also be used according to various embodiments. Any of the repair enzymes for use according to the methods and compositions described herein may be naturally occurring, recombinant or synthetic. In some instances, a DNA repair enzyme is a native or an in vitro-created chimeric protein with one or more activities. Cleavage agents, in various embodiments, comprise enzymatic activities, including enzyme mixtures, which include one or more of nicking endonucleases, AP endonucleases, glycosylases and lyases involved in base excision repair.

Without being bound by theory, a damaged base is removed by a DNA enzyme with glycosylase activity, which hydrolyses an N-glycosylic bond between the deoxyribose sugar moiety and the base. For example, an E. coli glycosylase and an UDG endonuclease act upon deaminated cytosine while two 3-mAde glycosylases from E. coli (Tag1 and Tagi1) act upon alkylated bases. The product of removal of a damaged base by a glycosylase is an AP site (apurinic/apyrimidinic site), also known as an abasic site, is a location in a nucleic acid that has neither a purine nor a pyrimidine base. DNA repair systems are often used to correctly replace the AP site. This is achieved in various instances by an AP endonuclease that nicks the sugar phosphate backbone adjacent to the AP site and the abasic sugar is removed. Some naturally occurring or synthetic repair systems include activities, such as the DIMA polymerase/DNA ligase activity, to insert a new nucleotide.

Repair enzymes are found in prokaryotic and eukaryotic cells. Some enzymes having applicability herein have glycosylase and AP endonuclease activity in one molecule. AP endonucleases are classified according to their sites of incision. Class I AP endonucleases and class II AP endonucleases incise DNA at the phosphate groups 3' and 5' to the baseless site leaving 3'-OH and 5'-phosphate termini. Class III and class IV AP endonucleases also cleave DNA at the phosphate groups 3' and 5' to the baseless site, but they generate a 3'-phosphate and a 5'-OH.

In some cases, AP endonucleases remove moieties attached to the 3' OH that inhibit polynucleotide polymerization. For example a 3' phosphate is converted to a 3' OH by E. coli endonuclease IV. In some cases, AP endonucleases work in conjunction with glycosylases to engineer nucleic acids at a site of mismatch, a non-canonical nucleoside or a base that is not one of the major nucleosides for a nucleic acid, such as a uracil in a DNA strand.

Examples of glycosylase substrates include, without limitation, uracil, hypoxanthine, 3-methyladenine (3-mAde), formamidopyrimidine (FAPY), 7,8 dihydro-8-oxyguanine and hydroxymethyluracil. In some instances, glycosyslase substrates incorporated into DNA site-specifically by nucleic acid extension from a primer comprising the substrate. In some instances, glycosylase substrates are introduced by chemical modification of a nucleoside, for example by deamination of cytosine, e.g. by bisulfate, nitrous acids, or spontaneous deamination, producing uracil, or by deamination of adenine by nitrous acids or spontaneous deamination, producing hypoxanthine. Other examples of chemical modification of nucleic acids include generating 3-mAde as a product of alkylating agents, FAPY (7-mGua) as product of methylating agents of DNA, 7,8-dihydro-8 oxoguanine as a mutagenic oxidation product of guanine, 4,6-diamino-5-FAPY produced by gamma radiation, and hydroxymethyuracil produced by ionizing radiation or oxidative damage to thymidine. Some enzymes comprise AP endonuclease and glycosylase activities that are coordinated either in a concerted manner or sequentially.

Examples of polynucleotide cleavage enzymes used to generate single-stranded nicks include the following types of enzymes derived from but not limited to any particular organism or virus or non-naturally occurring variants thereof: E. coli endonuclease IV, Tth endonuclease IV, human AP endonuclease, glycosylases, such as UDG, E. coli 3-methyladenine DNA glycoylase (AIkA) and human Aag, glycosylase/lyases, such as E. coli endonuclease III, E. coli endonuclease VIII, E. coli Fpg, human OGG1, and T4 PDG, and lyases. Exemplary additional DNA repair enzymes are listed in Table 1.

TABLE 1

DNA repair enzymes.

| Gene Name | Activity | Accession Number |
|---|---|---|
| UNG | Uracil-DNA glycosylase | NM_080911 |
| SMUG1 | Uracil-DNA glycosylase | NM_014311 |
| MBD4 | Removes U or T opposite G at CpG sequences | NM_003925 |
| TDG | Removes U, T or ethenoC opposite G | NM_003211 |
| OGG1 | Removes 8-oxoG opposite C | NM_016821 |
| MUTYH (MYH) | Removes A opposite 8-oxoG | NM_012222 |
| NTHL1 (NTH1) | Removes Ring-saturated or fragmented pyrimidines | NM_002528 |
| MPG | Removes 3-meA, ethenoA, hypoxanthine | NM_002434 |
| NEIL1 | Removes thymine glycol | NM_024608 |
| NEIL2 | Removes oxidative products of pyrimidines | NM_145043 |
| XPC | Binds damaged DNA as complex with RAD23B, CETN2 | NM_004628 |
| RAD23B (HR23B) | Binds damaged DNA as complex with XPC, CETN2 | NM_002874 |
| CETN2 | Binds damaged DNA as complex with XPC, RAD23B | NM_004344 |
| RAD23A (HR23A) | Substitutes for HR23B | NM_005053 |
| XPA | Binds damaged DNA in preincision complex | NM_000380 |
| RPA1 | Binds DNA in preincision complex | NM_002945 |
| RPA2 | Binds DNA in preincision complex | NM_002946 |
| RPA3 | Binds DNA in preincision complex | NM_002947 |
| ERCC5 (XPG) | 3' incision | NM_000123 |
| ERCC1 | 5' incision subunit | NM_001983 |
| ERCC4 (XPF) | 5' incision subunit | NM_005236 |
| LIG1 | DNA joining | NM_000234 |
| CKN1(CSA) | Cockayne syndrome; Needed for transcription-coupled NER | NM_000082 |
| ERCC6 (CSB) | Cockayne syndrome; Needed for transcription-coupled NER | NM_000124 |
| XAB2 (HCNP) | Cockayne syndrome; Needed for transcription-coupled NER | NM_020196 |
| DDB1 | Complex defective in XP group E | NM_001923 |
| DDB2 | DDB1, DDB2 | NM_000107 |
| MMS19L (MMS19) | Transcription and NER | NM_022362 |
| FEN1 (DNase IV) | Flap endonuclease | NM_004111 |
| SPO11 | endonuclease | NM_012444 |
| FLJ35220 (ENDOV) | incision 3' of hypoxanthine and uracil | NM_173627 |
| FANCA | Involved in tolerance or repair of DNA crosslinks | NM_000135 |
| FANCB | Involved in tolerance or repair of DNA crosslinks | NM_152633 |
| FANCC | Involved in tolerance or repair of DNA crosslinks | NM_000136 |
| FANCD2 | Involved in tolerance or repair of DNA crosslinks | NM_033084 |
| FANCE | Involved in tolerance or repair of DNA crosslinks | NM_021922 |
| FANCF | Involved in tolerance or repair of DNA crosslinks | NM_022725 |
| FANCG (XRCC9) | Involved in tolerance or repair of DNA crosslinks | NM_004629 |
| FANCL | Involved in tolerance or repair of DNA crosslinks | NM_018062 |
| DCLRE1A (SNM1) | DNA crosslink repair | NM_014881 |
| DCLRE1B (SNM1B) | Related to SNM1 | NM_022836 |
| NEIL3 | Resembles NEIL1 and NEIL2 | NM_018248 |
| ATRIP (TREX1) | ATR-interacting protein 5' alternative ORF of the TREX1/ATRIP gene | NM_130384 |
| NTH | Removes damaged pyrimidines | NP_416150.1 |
| NEI | Removes damaged pyrimidines | NP_415242.1 |
| NFI | Deoxyinosine 3' endonuclease | NP_418426.1 |
| MUTM | Formamidopyrimidine DNA glycosylase | NP_418092.1 |

TABLE 1-continued

DNA repair enzymes.

| Gene Name | Activity | Accession Number |
|---|---|---|
| UNG | Uracil-DNA glycosylase | NP_417075.1 |
| UVRA | DNA excision repair enzyme complex | NP_418482.1 |
| UVRB | DNA excision repair enzyme complex | NP_415300.1 |
| UVRC | DNA excision repair enzyme complex | NP_416423.3 |
| DENV | Pyrimidine dimer glycosylase | NP_049733.1 |

Provided herein are methods where one or more enzymatic activities, such as those of repair enzymes, are used in combination to generate a site-specific single-strand nick. For example, USER (Uracil-Specific Excision Reagent; New England BioLabs) generates a single nucleoside gap at the location of a uracil. USER is a mixture of Uracil DNA glycosylase (UDG) and the DNA glycosylase-lyase Endonuclease VIII. UDG catalyzes the excision of a uracil base, forming an abasic (apyrimidinic) site while leaving the phosphodiester backbone intact. The lyase activity of Endonuclease VIII is used to break the phosphodiester backbone at the 3' and 5' sides of the abasic site so that the base-free deoxyribose is released, creating a one nucleotide gap at the site of uracil nucleotide.

Provided herein are methods where a nucleic acid fragment is treated prior to assembly into a target nucleic acid of predetermined sequence. In some instances, nucleic acid fragments are treated to create a sticky end, such as a sticky end with a 3' overhang or a 5' overhang. For example, uracil bases are incorporated into one or both strands of the target nucleic acids, which are chewed off upon treatment with Uracil DNA glycosylase (UDG) and Endonuclease VIII (EndoVIII). In some instances, uracil bases are incorporated near the 5' ends (or 3' ends), such as at least or at least about 1, 2, 3, 4, 5, 6, 7, 8, 9,10, 11, 12, 13, 14, 15, 16, 17, 18, 19, 20 bases from the 5' end (or 3' end), of one or both strands. In some cases, uracil bases are incorporated near the 5' ends such as at most or at most about 20, 19, 18, 17, 16, 15, 14, 13, 12, 11, 10, 9, 8, 7, 6, 5, 4, 3, 2, 1 base from the 5' end, of one or both strands. In some cases, uracil bases are incorporated near the 5' end such as between 1-20, 2-19, 3-18, 4-17, 5-16, 6-15, 7-14, 8-13, 9-12, 10-13, 11-14 bases from the 5' end, of one or both strands. Those of skill in art will appreciate that the uracil bases may be incorporated near the 5' end such that the distance between the uracil bases and the 5' end of one or both strands may fall within a range bound by any of these values, for example from 7-19 bases.

Nucleic Acid Assembly

Provided herein are methods where two or more of the cleavage, annealing and ligation reactions are performed concurrently within the same mixture and the mixture comprises a ligase. In some cases, one or more of the various reactions is sped up and one or more of the various reactions is slowed down by adjusting the reaction conditions such as temperature. In some cases, the reaction is thermocycled between a maximum and minimum temperature to repeatedly enhance cleavage, melting, annealing, and/or ligation. In some cases, the temperature ranges from a high of 80 degrees Celsius. In some cases, the temperature ranges from a low to 4 degrees Celsius. In some cases, the temperature ranges from 4 degrees Celsius to 80 degrees Celsius. In some cases, the temperature ranges among intermediates in this range. In some cases, the temperature ranges from a high of 60 degrees Celsius. In some cases, the temperature ranges to a low of 16 degrees Celsius. In some cases, the temperature ranges from a high of 60 degrees Celsius to a low of 16 degrees Celsius. In some cases, the mixture is temperature cycled to allow for the removal of cleaved sticky ended distal fragments from precursor fragments at elevated temperatures and to allow for the annealing of the fragments with complementary sticky ends at a lower temperature. In some cases, alternative combinations or alternative temperatures are used. In yet more alternate cases the reactions occur at a single temperature. In some cases, palindromic sequences are excluded from overhangs. The number of fragment populations to anneal in a reaction varies across target nucleic acids. In some cases, a ligation reaction comprises 2, 3, 4, 5, 6, 7, 8, or more than 8 types of target fragments to be assembled. For a given target nucleic acid, in some cases, portions of the entire nucleic acid are synthesized in separate reactions. In some cases, intermediate nucleic acids are used in a subsequent assembly round that uses the same or a different method to assemble larger intermediates or the final target nucleic acid. The same or different cleavage agents, recognition sites, and cleavage sites are used in subsequent rounds of assembly. In some instances, consecutive rounds of assembly, e.g. pooled or parallel assembly, are used to synthesize larger fragments in a hierarchical manner. In some cases, described herein are methods and compositions for the preparation of a target nucleic acid, wherein the target nucleic acid is a gene, using assembly of shorter fragments.

Polymerase chain reaction (PCR)-based and non-polymerase-cycling-assembly (PCA)-based strategies may be used for gene synthesis. In addition, non-PCA-based gene synthesis using different strategies and methods, including enzymatic gene synthesis, annealing and ligation reaction, simultaneous synthesis of two genes via a hybrid gene, shotgun ligation and co-ligation, insertion gene synthesis, gene synthesis via one strand of DNA, template-directed ligation, ligase chain reaction, microarray-mediated gene synthesis, Golden Gate Gene Assembly, Blue Heron solid support technology, Sloning building block technology, RNA-mediated gene assembly, the PCR-based thermodynamically balanced inside-out (TBIO) (Gao et al., 2003), two-step total gene synthesis method that combines dual asymmetrical PCR (DA-PCR) (Sandhu et al., 1992), overlap extension PCR (Young and Dong, 2004), PCR-based two-step DNA synthesis (PTDS) (Xiong et al., 2004b), successive PCR method (Xiong et al., 2005, 2006a), or any other suitable method known in the art can be used in connection with the methods and compositions described herein, for the assembly of longer polynucleotides from shorter oligonucleotides.

Amplification

Amplification reactions described herein can be performed by any means known in the art. In some cases, the nucleic acids are amplified by polymerase chain reaction (PCR). Other methods of nucleic acid amplification include, for example, ligase chain reaction, oligonucleotide ligations assay, and hybridization assay. DNA polymerases described herein include enzymes that have DNA polymerase activity even though it may have other activities. A single DNA polymerase or a plurality of DNA polymerases may be used throughout the repair and copying reactions. The same DNA polymerase or set of DNA polymerases may be used at different stages of the present methods or the DNA polymerases may be varied or additional polymerase added during various steps. Amplification may be achieved through any process by which the copy number of a target sequence is increased, e.g. PCR. Amplification can be performed at any point during a multi reaction procedure, e.g. before or after pooling of sequencing libraries from independent reaction volumes and may be used to amplify any suitable target molecule described herein.

Oligonucleic Acid Synthesis

Oligonucleic acids serving as target nucleic acids for assembly may be synthesized de novo in parallel. The oligonucleic acids may be assembled into precursor fragments which are then assembled into target nucleic acids. In some case, greater than about 100, 1000, 16,000, 50,000 or 250,000 or even greater than about 1,000,000 different oligonucleic acids are synthesized together. In some cases, these oligonucleic acids are synthesized in less than 20, 10, 5, 1, 0.1 cm$^2$, or smaller surface area. In some instances, oligonucleic acids are synthesized on a support, e.g. surfaces, such as microarrays, beads, miniwells, channels, or substantially planar devices. In some case, oligonucleic acids are synthesized using phosphoramidite chemistry. In order to host phosphoramidite chemistry, the surface of the oligonucleotide synthesis loci of a substrate in some instances is chemically modified to provide a proper site for the linkage of the growing nucleotide chain to the surface. Various types of surface modification chemistry exists which allow a nucleotide to attached to the substrate surface.

The DNA and RNA synthesized according to the methods described herein may be used to express proteins in vivo or in vitro. The nucleic acids may be used alone or in combination to express one or more proteins each having one or more protein activities. Such protein activities may be linked together to create a naturally occurring or non-naturally occurring metabolic/enzymatic pathway. Further, proteins with binding activity may be expressed using the nucleic acids synthesized according to the methods described herein. Such binding activity may be used to form scaffolds of varying sizes.

Computers and Software

The methods and systems described herein may comprise and/or are performed using a software program on a computer system. Accordingly, computerized control for the optimization of design algorithms described herein and the synthesis and assembly of nucleic acids are within the bounds of this disclosure. For example, supply of reagents and control of PCR reaction conditions are controlled with a computer. In some instances, a computer system is programmed to search for sticky end motifs in a user specified predetermined nucleic acid sequence, interface these motifs with a list of suitable nicking enzymes, and/or determine one or more assembly algorithms to assemble fragments defined by the sticky end motifs. In some instances, a computer system described herein accepts as an input one or more orders for one or more nucleic acids of predetermined sequence, devises an algorithm(s) for the synthesis and/or assembly of the one or more nucleic acid fragments, provides an output in the form of instructions to a peripheral device(s) for the synthesis and/or assembly of the one or more nucleic acid fragments, and/or instructs for the production of the one or more nucleic acid fragments by the peripheral devices to form the desired nucleic acid of predetermined sequence. In some instances, a computer system operates without human intervention during one or more of steps for the production of a target nucleic acid of predetermined sequence or nucleic acid fragment thereof.

In some cases, a software system is used to identify sticky end motif sequence for use in a target sequence assembly reaction consistent with the disclosure herein. For example, in some cases, a software system is used to identify a sticky end motif using at least one, up to and including all, of the steps as follows. Given a final target sequence of length I, a desired target fragment of J, and a desired sticky end overhang length of K (for 5' ANNNNT 3'(SEQ ID NO.: 2), K=6) and a maximum desired similarity between sites of L, assembly parameters are in some instances calculated as follows. In some cases, J is about 200. In some cases, J is about 1000. In some cases, J is a number selected from about 50, 100, 150, 200, 250, 300, 350, 400, 450, 500, 550, 600, 650, 700, 750, 800, 850, 900, 950, 100, or more than 1000. In some cases, J is a value in the range from 70-250. I/J is the number of fragments to be assembled (x). X-1 breakpoints are added along the target sequence, reflecting the number of junctions in the target sequence to be assembled. In some cases, junctions are selected at equal intervals or at approximately equal intervals throughout the target sequence.

For at least one breakpoint, the nearest breakpoint site candidate is identified, for example having ANNNNT (SEQ ID NO.: 2), or GNNNNC (SEQ ID NO.: 17). Consistent with the disclosure herein, the breakpoint has a 6 base sequence in some cases, while in other cases the junction sequence is 1, 2, 3, 4, or 5 bases, and in other cases the junction is 7, 8, 9, 10, or more than 10 bases. In some cases, the breakpoint site candidate comprises a purine at a first position, a number of bases ranging from 0 to 8 or greater, preferably 1 or greater in some cases, and a pyrimidine at a final position such that the first position purine and the final position pyrimidine are a complementary base pair (either AT or GC).

In some cases, breakpoint selection is continued for sites up to and In some cases, including each breakpoint or near each breakpoint. Site candidates are evaluated so as to reduce the presence of at least one of palindromic sequences, homopolymers, extreme GC content, and extreme AT content. Sites are assessed in light of at least one of these criteria, optionally in combination with or alternatively viewing additional criteria for site candidate evaluation. If a site is determined or calculated to have undesirable qualities, then the next site in a vicinity is subjected to a comparable evaluation. Site candidates are further evaluated for cross-site similarity, for example excluding sites that share more than L bases in common at common positions or in common sequence. In some cases, L is 2, such that the central NNNN of some selected sticky ends must not share similar bases at similar positions. In some cases, L is 2, such that the central NNNN of some selected sticky ends must not share similar bases in similar patterns. In alternate cases, L is 3, 4, 5, 6, or greater than 6. Site candidates are evaluated individually or in combination, until a satisfactory sticky end system or group of distinct sticky ends is identified for a given assembly reaction. Alternate methods employ at least one of the steps recited above, alone or in combination with additional steps recited above or in combination with at least one step not recited above, or in combination with a plurality of steps recited above and at least one step not recited above.

A method described herein may be operably linked to a computer, either remotely or locally. In some cases, a method described herein is performed using a software program on a computer. In some cases, a system described herein comprises a software program for performing and/or analyzing a method or product of a method described herein. Accordingly, computerized control of a process step of any method described herein is envisioned.

Figure 7:
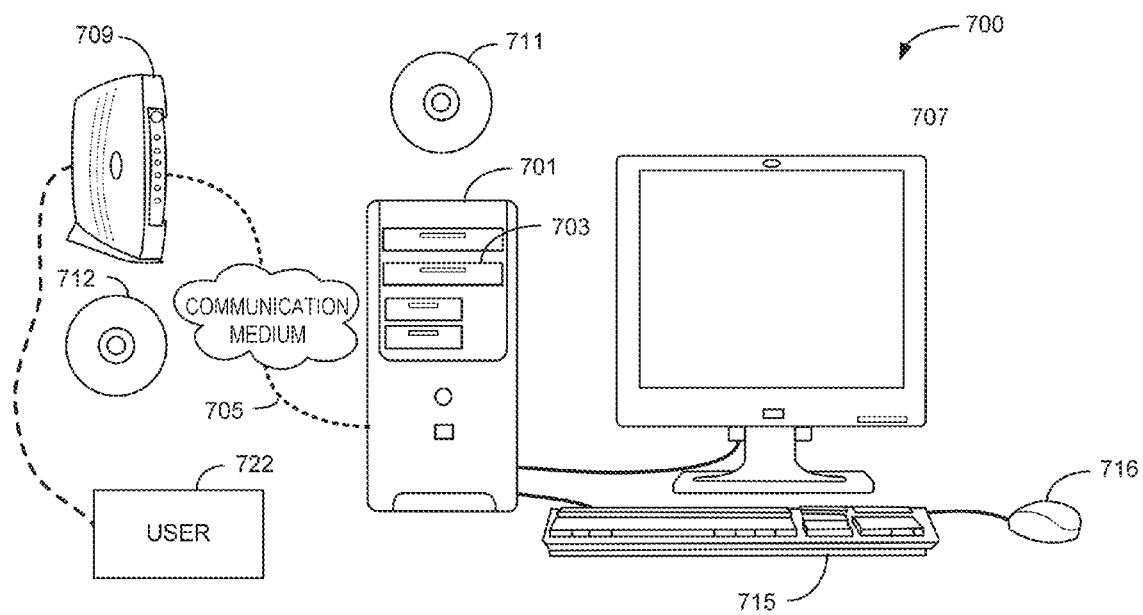
FIG. 7 illustrates an example of a computer system.

The computer system 700 illustrated in FIG. 7 depicts a logical apparatus that reads instructions from media 711 and/or a network port 705, which is optionally be connected to server 709 having fixed media 712. In some cases, a computer system, such as shown in FIG. 7, includes a CPU 701, disk drive 703, optional input devices such as keyboard 715 and/or mouse 716 and optional monitor 707. Data communication can be achieved through the indicated communication medium to a server at a local or a remote location. Communication medium includes any means of transmitting and/or receiving data. As non-limiting examples, communication medium is a network connection, a wireless connection, and/or an internet connection. Such a connection can provide for communication over the World Wide Web. It is envisioned that data relating to the present disclosure is transmittable over such networks or connections for reception and/or review by a user 722, as illustrated in FIG. 7.

Figure 8:
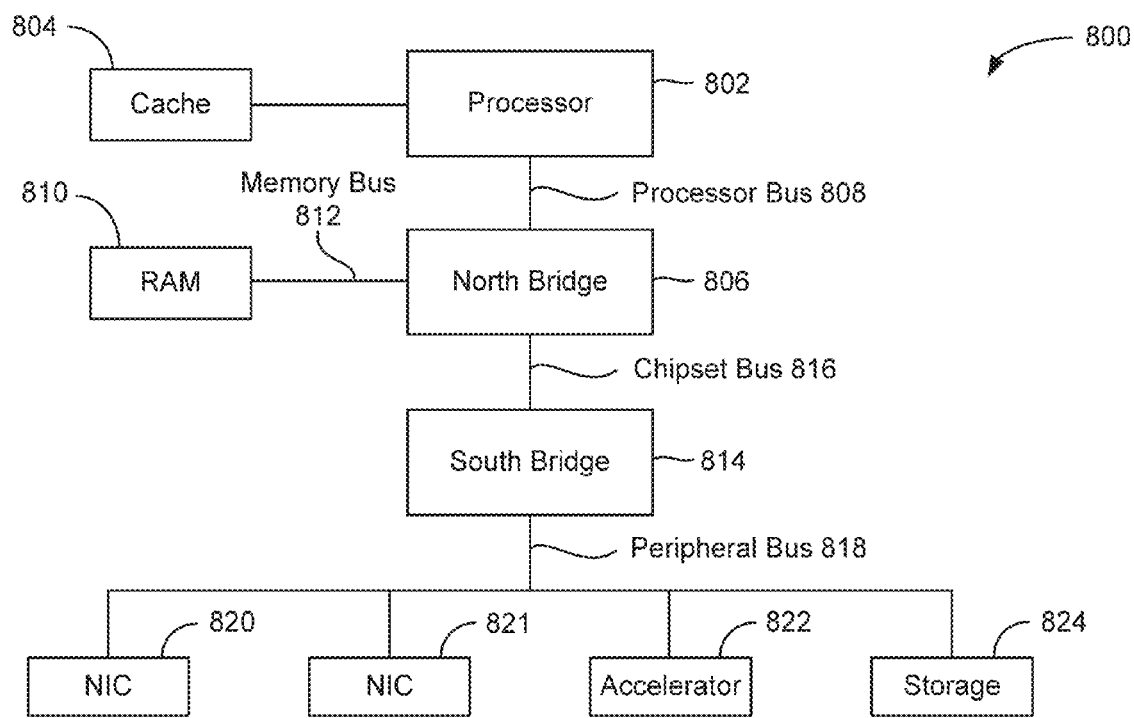
FIG. 8 is a block diagram illustrating an example architecture of a computer system.

A block diagram illustrating a first example architecture of a computer system 800 for use in connection with example embodiments of the disclosure is shown in FIG. 8. The example computer system of FIG. 8 includes a processor 802 for processing instructions. Non-limiting examples of processors include: Intel Xeon™ processor, AMD Opteron™ processor, Samsung 32-bit RISC ARM 1176JZ (F)-S v1.0™ processor, ARM Cortex-A8 Samsung S5PC100™ processor, ARM Cortex-A8 Apple A4™ processor, Marvell PXA 930™ processor, and a functionally-equivalent processor. Multiple threads of execution can be used for parallel processing. In some instances, multiple processors or processors with multiple cores are used, whether in a single computer system, in a cluster, or distributed across systems over a network comprising a plurality of computers, cell phones, and/or personal data assistant devices.

In the computer system of FIG. 8, a high speed cache 804 is connected to, or incorporated in, the processor 802 to provide a high speed memory for instructions or data that have been recently, or are frequently, used by processor 802. The processor 802 is connected to a north bridge 806 by a processor bus 808. The north bridge 806 is connected to random access memory (RAM) 810 by a memory bus 812 and manages access to the RAM 810 by the processor 802. The north bridge 806 is also connected to a south bridge 814 by a chipset bus 816. The south bridge 814 is, in turn, connected to a peripheral bus 818. The peripheral bus is, for example, PCI, PCI-X, PCI Express, or another peripheral bus. The north bridge and south bridge are often referred to as a processor chipset and manage data transfer between the processor, RAM, and peripheral components on the peripheral bus 818. In some alternative architectures, the functionality of the north bridge is incorporated into the processor instead of using a separate north bridge chip. In some instances, system 800 includes an accelerator card 822 attached to the peripheral bus 818. The accelerator may include field programmable gate arrays (FPGAs) or other hardware for accelerating certain processing. For example, an accelerator is used for adaptive data restructuring or to evaluate algebraic expressions used in extended set processing.

Software and data are stored in external storage 824, which can then be loaded into RAM 810 and/or cache 804 for use by the processor. System 800 includes an operating system for managing system resources. Non-limiting examples of operating systems include: Linux, Windows™, MACOS™, BlackBerry OS™, iOS™, and other functionally-equivalent operating systems, as well as application software running on top of the operating system for managing data storage and optimization in accordance with example embodiments of the present disclosure. System 800 includes network interface cards (NICs) 820 and 821 connected to the peripheral bus for providing network interfaces to external storage, such as Network Attached Storage (NAS) and other computer systems that can be used for distributed parallel processing.

Figure 9:
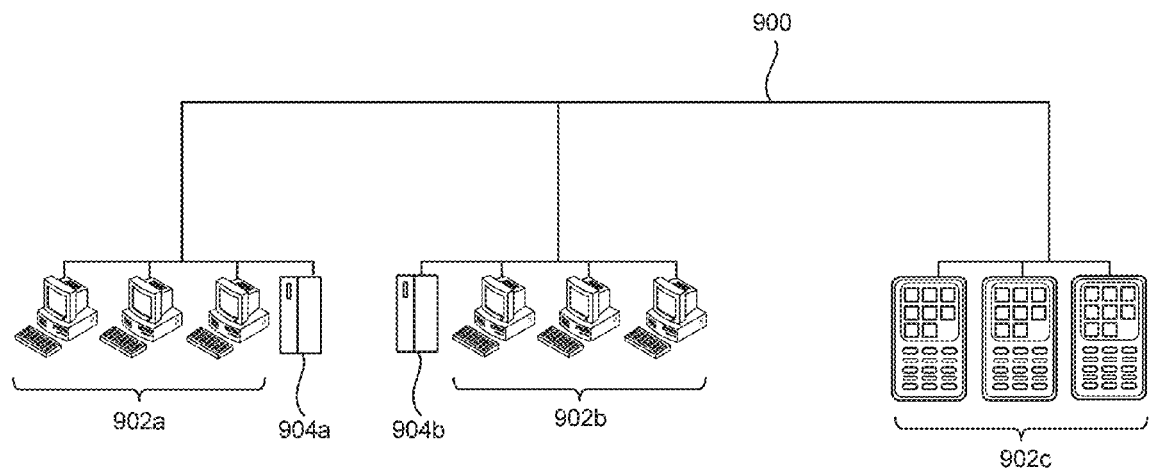
FIG. 9 is a diagram demonstrating a network configured to incorporate a plurality of computer systems, a plurality of cell phones and personal data assistants, and Network Attached Storage (NAS).

FIG. 9 is a diagram showing a network 900 with a plurality of computer systems 902*a*, and 902*b*, a plurality of cell phones and personal data assistants 902*c*, and Network Attached Storage (NAS) 904*a*, and 904*b*. In some instances, systems 902*a*, 902*b*, and 902*c* manage data storage and optimize data access for data stored in NAS 904*a* and 904*b*. A mathematical model can be used for the data and be evaluated using distributed parallel processing across computer systems 902*a* and 902*b*, and cell phone and personal data assistant system 902*c*. Computer systems 902*a* and 902*b*, and cell phone and personal data assistant system 902*c* can provide parallel processing for adaptive data restructuring of the data stored in NAS 904*a* and 904*b*. FIG. 9 illustrates an example only, and a wide variety of other computer architectures and systems can be used in conjunction with the various embodiments of the present disclosure. For example, a blade server can be used to provide parallel processing. Processor blades can be connected through a back plane to provide parallel processing. Storage can also be connected to the back plane or as NAS through a separate network interface.

In some instances, processors maintain separate memory spaces and transmit data through network interfaces, back plane or other connectors for parallel processing by other processors. In some instances, some or all of the processors use a shared virtual address memory space.

Figure 10:
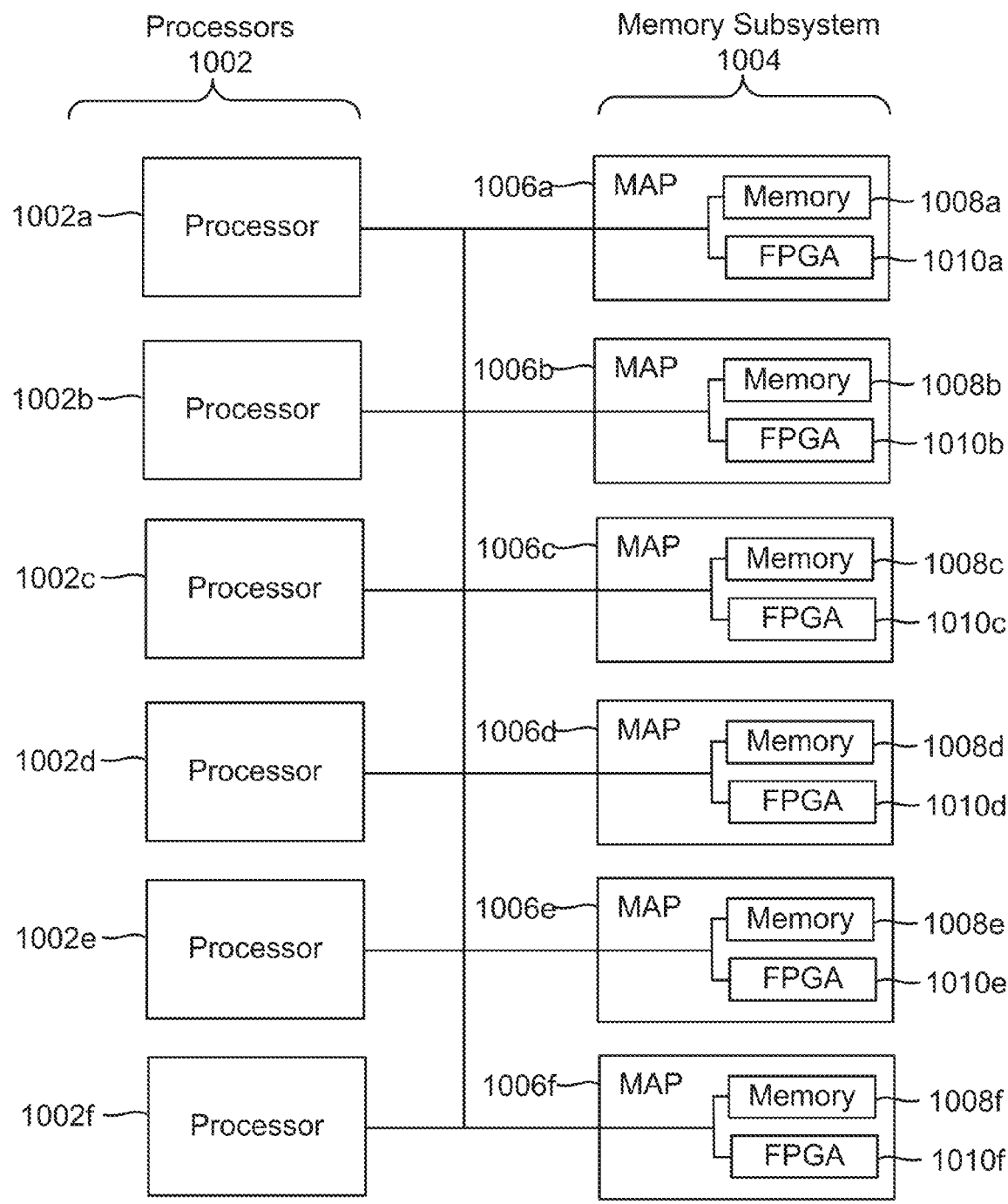
FIG. 10 is a block diagram of a multiprocessor computer system using a shared virtual address memory space.

FIG. 10 is a block diagram of a multiprocessor computer system 1000 using a shared virtual address memory space in accordance with an example embodiment. The system includes a plurality of processors 1002*a-f* that can access a shared memory subsystem 1004. The system incorporates a plurality of programmable hardware memory algorithm processors (MAPs) 1006*a-f* in the memory subsystem 1004. Each MAP 1006*a-f* can comprise a memory 1008*a-f* and one or more field programmable gate arrays (FPGAs) 1010*a-f*. The MAP provides a configurable functional unit and particular algorithms or portions of algorithms can be provided to the FPGAs 1010*a-f* for processing in close coordination with a respective processor. For example, the MAPs are used to evaluate algebraic expressions regarding a data model and to perform adaptive data restructuring in example embodiments. In this example, each MAP is globally accessible by all of the processors for these purposes. In one configuration, each MAP uses Direct Memory Access (DMA) to access an associated memory 1008*a-f*, allowing it to execute tasks independently of, and asynchronously from, the respective microprocessor 1002*a-f*. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example embodiments, including systems using any combination of general processors, co-processors, FPGAs and other programmable logic devices, system on chips (SOCs), application specific integrated circuits (ASICs), and other processing and logic elements. In some instances, all or part of the computer system can be implemented in software or hardware. Any variety of data storage media can be used in connection with example embodiments, including random access memory, hard drives, flash memory, tape drives, disk arrays, Network Attached Storage (NAS) and other local or distributed data storage devices and systems.

The following examples are set forth to illustrate more clearly the principle and practice of embodiments disclosed herein to those skilled in the art and are not to be construed as limiting the scope of any claimed embodiments.

EXAMPLES

Example 1: Restriction Enzyme-Free Ligation of a Gene Fragment Using Sticky Ends Amplification with Uracil-Containing PCR Primers A gene of about 1 kB (the "1 kB Gene Construct") was selected to perform restriction enzyme-free ligation with a vector:

```
                                           (SEQ ID NO.: 48)
5'CAGCAGTTCCTCGCTCTTCTCACGACGAGTTCGACATCAACAAGCTGC

GCTACCACAAGATCGTGCTGATGGCCGACGCCGATGTTGACGGCCAGCAC

ATCGCAACGCTGCTGCTCACCCTGCTTTTCCGCTTCATGCCAGACCTCGT

CGCCGAAGGCCACGTCTACTTGGCACAGCCACCTTTGTACAAACTGAAGT

GGCAGCGCGGAGAGCCAGGATTCGCATACTCCGATGAGGAGCGCGATGAG

CAGCTCAACGAAGGCCTTGCCGCTGGACGCAAGATCAACAAGGACGACGG

CATCCAGCGCTACAAGGGTCTCGGCGAGATGAACGCCAGCGAGCTGTGGG

AAACCACCATGGACCCAACTGTTCGTATTCTGCGCCGCGTGGACATCACC

GATGCTCAGCGTGCTGATGAACTGTTCTCCATCTTGATGGGTGACGACGT

TGTGGCTCGCCGCAGCTTCATCACCCGAAATGCCAAGGATGTTCGTTTCC

TCGATATCTAAAGCGCCTTACTTAACCCGCCCCTGGAATTCTGGGGCGG

GTTTTGTGATTTTTAGGGTCAGCACTTTATAAATGCAGGCTTCTATGGCT

TCAAGTTGGCCAATACGTGGGGTTGATTTTTTAAAACCAGACTGGCGTGC

CCAAGAGCTGAACTTTCGCTAGTCATGGGCATTCCTGGCCGGTTTCTTGG

CCTTCAAACCGGACAGGAATGCCCAAGTTAACGGAAAAACCGAAAGAGGG

GCACGCCAGTCTGGTTCTCCCAAACTCAGGACAAATCCTGCCTCGGCGCC

TGCGAAAAGTGCCCTCTCCTAAATCGTTTCTAAGGGCTCGTCAGACCCCA

GTTGATACAAACATACATTCTGAAAATTCAGTCGCTTAAATGGGCGCAGC

GGGAAATGCTGAAAACTACATTAATCACCGATACCCTAGGGCACGTGACC

TCTACTGAACCCACCACCACAGCCCATGTTCCACTACCTGATGGATCTTC

CACTCCAGTCCAAATTTGGGCGTACACTGCGAGTCCACTACGAT3'
```

The 1 kB Gene Construct, which is an assembled gene fragment with heterogeneous sequence populations, was purchased as a single gBlock (Integrated DNA Technologies). The 1 kB Gene Construct was amplified in a PCR reaction with uracil-containing primers. The PCR reaction components were prepared according to Table 2.

TABLE 2

PCR reaction mixture comprising uracil-containing primers.

10 µL 5X HF buffer (ThermoFisher Scientific)
0.8 µL 10 mM dNTP (NEB)
1 ng template (1 kB Gene Construct)

TABLE 2-continued

PCR reaction mixture comprising uracil-containing primers.

2.5 µL forward primer (10 µM) 5'CAGCAGT/ideoxyU/CCTCGCTCTTCT3' (SEQ ID NO.: 49; Integrated DNA Technologies)
2.5 µL reverse primer (10 µM) 5'ATCGTAG/ideoxyU/GGACTCGCAGTGTA3' (SEQ ID NO.: 50; Integrated DNA Technologies)
0.5 µL Phusion-U hot start DNA polymerase (ThermoFisher Scientific, 2 U/µL)
Water up to 50 µL The 1 kB Gene Construct was amplified with the uracil-containing primers in a PCR reaction performed using the thermal cycling conditions described in Table 3.

TABLE 3

PCR reaction conditions for amplifying a gene with uracil-containing primers.

| Step | Cycle |
|---|---|
| 1 | 1 cycle: 98° C., 30 sec |
| 2 | 20 cycles: 98° C., 10 sec; 68° C., 15 sec; 72° C., 60 sec |
| 3 | 1 cycle: 72° C., 5 min |
| 4 | Hold: 4° C. |

The uracil-containing PCR products were purified using Qiagen MinElute column, eluted in 10 µL, EB buffer, analyzed by electrophoresis (BioAnalyzer), and quantified on a NanoDrop to be 93 ng/µL. The uracil-containing PCR products of the 1 kB Gene Construct were incubated with a mixture of Uracil DNA glycosylase (UDG) and Endonuclease VIII to generate sticky ends. The incubation occurred at 37° C. for 30 min in a reaction mixture as described in Table 4.

TABLE 4

Digestion reaction conditions for generating sticky ends in a uracil-containing gene.

| Reaction component | Quantity |
|---|---|
| Uracil-containing PCR product | 15 nM (final concentration) |
| 10x CutSmart buffer (NEB) | 10 µL |
| UDG/EndoVIII (NEB or Enzymatics) | 2 µL of 1 U/µL |
| Water | Up to 94.7 µL |

Preparation of Artificial Vector

Two synthetic oligonucleotides having 3' overhangs when annealed together ("Artificial Vector") were hybridized and ligated to the digested uracil-containing 1 kB Gene Construct ("Sticky-end Construct"). The first oligo ("Upper Oligo", SEQ ID NO.: 51) contains a 5' phosphate for ligation. The second oligonucleotide ("Lower Oligo", SEQ ID NO.: 52) lacks a base on the 5' end such that it leaves a nucleotide gap after hybridizing to the Sticky-end Construct with the Upper Oligo. Further, the Lower Oligo lacks a 5' phosphate to ensure that no ligation occurs at this juncture. The first six phosphate bonds on the Lower Oligo are phosphorothioated to prevent exonuclease digestion from the gap. Oligonucleic acid sequences of the Artificial Vector are shown in Table 5. An asterisk denotes a phosphorothioate bond.

TABLE 5

Sequence identities of an artificial
vector for ligation to asticky-end gene product.

| Sequence ID | Sequence |
|---|---|
| SEQ ID NO.: 51 | 5'/5phos/TACGCTCTTCCTCAGCA GTGGTCATCGTAGT3' |
| SEQ ID NO.: 52 | 5'A*C*C*A*C*T*GCTGAGGAAGAG CGTACAGCAGTT3' |
| Artificial Vector SEQ ID NO.: 79 | TACGCTCTTCCTCAGCA G T G G T CATCGTAGTTTGACGACATGCGAGAAG GAGTCGT*C*A*C*C*A* |

The Sticky-end Construct was mixed with Upper Oligo and Lower Oligo (5 µM each) in 1× CutSmart buffer (NEB). The mixture was heated to 95° C. for 5 min, and then slowly cooled to anneal. The annealed product comprised a circularized gene construct comprising the 1 kB Gene Construct. This construct was generated without the remnants of any restriction enzyme cleavage sites and thus lacked any associated enzymatic "scars."

Example 2: Assembly of LacZ Gene into a Plasmid

A LacZ gene was assembled into a 5 kb plasmid from three precursor LacZ fragments and 1 precursor plasmid fragment. Assembly was performed using 9 different reaction conditions.

Preparation of Precursor Plasmid Fragments

A 5 kb plasmid was amplified with two different sets of primers for introducing a sticky end motif comprising a non-canonical base (SEQ ID NO.: 53): set A (SEQ ID NOS.: 54 and 55) and set B (SEQ ID NOS.: 56 and 57), shown in Table 6, to produce plasmid precursor fragments A and B, respectively.

TABLE 6

Sequence identities of plasmid primers.

| Sequence identity | Primer name | Sequence |
|---|---|---|
| SEQ ID NO.: 54 | plasmid-Fa | TGATCGGCAATGATATG/ideoxyU/ CTGGAAAGAACATGTG |
| SEQ ID NO.: 55 | plasmid-Ra | TGATCGGCAATGATGGC/ideoxyU/ TATAATGCGACAAACAACAG |
| SEQ ID NO.: 56 | plasmid-Fb | TGATCGGCAATGATATG/ideoxyU/ CGCTGGAAAGAACATG |
| SEQ ID NO.: 57 | plasmid-Ra | TGATCGGCAATGATGGC/ideoxyU/ CGTATAATGCGACAAACAAC |

Each primer set comprises, in 5' to 3' order: 6 adaptor bases (TGATCG, SEQ ID NO.: 58), a first nicking enzyme recognition site (GCAATG, SEQ ID NO.: 59), a sticky end motif comprising a non-canonical base (ANNNNU, SEQ ID NO.: 53), and plasmid sequence. The first two bases of the plasmid sequence in the forward and reverse primers of set B are a CG. These two bases are absent from the forward and reverse primers of set A. Two plasmid fragments, plasmid A and plasmid B, were amplified using primer set A and primer B, respectively. The composition of the amplification reaction is shown in Table 7. The amplification reaction conditions are shown in Table 8.

TABLE 7

PCR reaction mixture for amplification of a 5 kb plasmid.

| PCR component | Quantity (µL) | Concentration in mixture |
|---|---|---|
| Phusion U (2 U/µL) | 1 | 1 U/50 µL |
| 5x Phusion HF buffer | 20 | 1x |
| 10 mM dNTP | 4 | 400 µM |
| Plasmid template (50 pg/µL) | 4 | 100 pg/50 µL |
| plasmid-Fa or plasmid-Fb (200 µM) | 0.25 | 0.5 µM |
| plasmid-Ra or plasmid-Rb (200 µM) | 0.25 | 0.5 µM |
| Water | 70.5 | |

TABLE 8

PCR reaction conditions for amplification of a 5 kb plasmid.

| Step | Cycle |
|---|---|
| 1 | 1 cycle: 98° C., 30 sec |
| 2 | 30 cycles: 98° C., 10 sec; 49° C., 15 sec; 72° C., 90 sec |
| 3 | 1 cycle: 72° C., 5 min |
| 4 | Hold: 4° C., 15-30 sec per kb |

The precursor plasmid fragment was treated with DpnI, denatured and purified.

Preparation of Precursor LacZ Fragments

The LacZ sequence was analyzed to identify two sticky end motifs which partition the sequence into roughly 3, 1 kb fragments: LacZ fragments 1-3. Sequence identities of the two sticky end motifs and the LacZ fragments are shown in Table 9. SEQ ID NO.: 60 shows the complete LacZ gene, wherein motifs are italicized, fragment 1 is underlined with a single line, fragment 2 is underlined with a squiggly line, and fragment 3 is underlined with a double line.

TABLE 9

Sequence identities of LacZ fragments and sticky end motifs.

| Sequence identity | Sequence name | Sequence |
|---|---|---|
| SEQ ID NO.: 61 | fragment 1 | ATGACCATGATTACGGATTCACTGGCCGTCG TTTTACAACGTCGTGACTGGGAAAACCCTGG CGTTACCCAACTTAATCGCCTTGCAGCACAT CCCCCTTTCGCCAGCTGGCGTAATAGCGAAG AGGCCCGCACCGATCGCCCTTCCCAACAGTT GCGCAGCCTGAATGGCGAATGGCGCTTTGCC TGGTTTCCGGCACCAGAAGCGGTGCCGGAAA GCTGGCTGGAGTGCGATCTTCCTGAGGCCGA TACTGTCGTCGTCCCCTCAAACTGGCAGATG CACGGTTACGATGCGCCCATCTACACCAACG TGACCTATCCCATTACGGTCAATCCGCCGTT TGTTCCCACGGAGAATCCGACGGGTTGTTAC TCGCTCACATTTAATGTTGATGAAAGCTGGC TACAGGAAGGCCAGACGCGAATTATTTTTGA TGGCGTTAACTCGGCGTTTCATCTGTGGTGC AACGGGCGCTGGGTCGGTTACGGCCAGGACA GTCGTTTGCCGTCTGAATTTGACCTGAGCGC ATTTTTACGCGCCGGAGAAAACCGCCTCGCG GTGATGGTGCTGCGCTGGAGTGACGGCAGTT ATCTGGAAGATCAGGATATGTGGCGGATGAG CGGCATTTTCCGTGACGTCTCGTTGCTGCAT AAACCGACTACACAAATCAGCGATTTCCATG TTGCCACTCGCTTTAATGATGATTTCAGCCG CGCTGTATGGAGGCTGAAGTTCAGATGTGC GGCGAGTTGCGTGACTACCTACGGGTAACAG TTTCTTTATGGCAGGGTGAAACGCAGGTCGC CAGCGGCACCGCGCCTTTCGGCGGTGAAATT ATCGATGAGCGTGGTGGTTATGCCGATCGCG TCACACTACGTCTGAACGTCGAAAACCCGAA |

TABLE 9-continued

Sequence identities of LacZ fragments and sticky end motifs.

| Sequence identity | Sequence name | Sequence |
|---|---|---|
| | | ACTGTGGAGCGCCGAAATCCCGAATCTCTAT CGTGCGGTGGTTGAACTGCACACCGCCGACG GCACGCTGATTGAAGCAGAAGCCTGCGATGT CGGTTTCCGCGAGGTGCGGATTGAA |
| SEQ ID NO.: 62 | fragment 2 | CTGCTGCTGCTGAACGGCAAGCCGTTGCTGA TTCGAGGCGTTAACCGTCACGAGCATCATCC TCTGCATGGTCAGGTCATGGATGAGCAGACG ATGGTGCAGGATATCCTGCTGATGAAGCAGA ACAACTTTAAGCGCCGTGCGCTGTTCGCATTA TCCGAACCATCCGCTGTGGTACACGCTGTGC GACCGCTACGGCCTGTATGTGGTGGATGAAG CCAATATTGAAACCCACGGCATGGTGCCAAT GAATCGTCTGACCGATGATCCGCGCTGGCTA CCGGCGATGAGCGAACGCGTAACGC TGCACGCGATCGTAATCACCCGAGTGTGAT CATCTGGTCGCTGGGGAATGAATCAGGCCAC GGCGCTAATCACGACGCGCTGTATCGCTGGA TCAAATCTGTCGATCCTTCCCGCCCGTGCA GTATGAAGGCGGCGGAGCCGACACCACGGCC ACCGATATTATTTGCCCGATGTACGCGCGCG TGGATGAAGACCAGCCCTTCCCGGCTGTGCC GAAATGGTCCATCAAAAAATGGCTTTCGCTA CCTGGAGAGACGCGCCCGCTGATCCTTTTGCG AATACGCCCACGCGATGGGTAACAGTCTTGG CGGTTTCGCTAAATACTGGCAGGCGTTTCGT CAGTATCCCCGTTTACAGGGCGGCTTTCGTCT GGGACTGGGTGGATCAGTCGCTGATTAAATA TGATGAAAACGGCAACCCGTGGTCGGCTTAC GGCGGTGATTTTGGCGATACGCCGAACGATC GCCAGTTCTGTATGAACGGTCTGGTCTTTGC CGACCGCACGCCGCATCCAGCGCTGACGGAA GCAAAACACCAGCAGCAGTTTTTCCAGTTCC GTTTATCCGGGCAAACCATCGAAGTGACCAG CGAATACCTGTTCCGTCATAGCGATAACGAG CTCCTGCACTGGATGGTGGCGCTGATGGTA AGCCGCTGGCAAGCGGTGAAGTGCCTCTGGA TGTCGCTCCACAAGGTAA |
| SEQ ID NO.: 63 | fragment 3 | GATTGAACTGCCTGAACTACCGCAGCCGGAG AGCGCCGGGCAACTCTGGCTCACAGTACGCG TAGTGCAACCGAACGCGACCGCATGGTCAGA AGCCGGGCACATCAGCGCCTGGCAGCAGTGG CGTCTGGCGGAAAACCTCAGTGTGACGCTCC CCGCCGCGTCCCACGCCATCCCGCATCTGAC CACCAGCGAAATGGATTTTTGCATCGAGCTG GGTAATAAGCGTTGGCAATTTAACCGCCAGT CAGGCTTTCTTTCACAGATGTGGATTGGCGA TAAAAAACAACTGCTGACGCCGCTGCGCGAT CAGTTCACCCGTGCACCGCTGGATAACGACA TTGGCGTAAGTGAAGCGACCCGCATTGACCC TAACGCCTGGGTCGAACGCTGGAAGGCGGCG GGCCATTACCAGGCCGAAGCAGCGTTGTTGC AGTGCACGGCAGATACACTTGCTGATGCGGT GCTGATTACGACCGCTCACGCGTGGCAGCAT CAGGGGAAAACCTTATTTATCAGCCGGAAAA CCTACCGGATTGATGGTAGTGGTCAAATGGC GATTACCGTTGATGTTGAAGTGGCGAGCGAT ACACCGCATCCGGCGCGGATTGGCCTGAACT GCCAGCTGGCGCAGGTAGCAGAGCGGGTAAA CTGGCTCGGATTAGGGCCGAAGAAAACTAT CCCGACCGCCTTACCGCCGTGTTTGACC GCTGGGATCTGCCATTGTCAGACATGTATAC CCCGTACGTCTTCCCGAGCGAAAACGGTCTG CGCTGCGGGACGCGCGAATTGAATTATGGCC CACACCAGTGGCGCGGCGACTTCCAGTTCAA CATCAGCCGCTACAGTCAACAGCAACTGATG GAAACCAGCCATCGCCATCTGCTGCACGCGG AAGAAGGCACATGGCTGAATATCGACGGTTT CCATATGGGGATTGGTGGCGACGACTCCTGG AGCCCGTCAGTATCGGCGGAATTCCAGCTGA GCGCCGGTCGCTACCATTACCAGTTGGTCTG GTGTCAAAAATAA |
| SEQ ID NO.: 64 | motif 1 | AATGGT |
| SEQ ID NO.: 65 | motif 2 | ACAGTT |
| SEQ ID NO.: 60 | LacZ | *AGCC*ATATGACCATGATTACGGATTCACTGG CCGTCGTTTTACAACGTCGTGACTGGGAAAA CCCTGGCGTTACCCAACTTAATCGCCTTGCA GCACATCCCCCTTTCGCCAGCTGGCGTAATA GCGAAGAGGCCCGCACCGATCGCCCTTCCCA ACAGTTGCGCAGCCTGAATGGCGAATGGCGC TTTGCCTGGTTTCCGGCACCAGAAGCGGTGC CGGAAAAGCTGGCTGGAGTGCGATCTTCCTGA GGCCGATACTGTCGTCGTCCCCTCAAACTGG CAGATGCACGGTTACGATGCGCCCATCTACA CCAACGTGACCTATCCCATTACGGTCAATCC GCCGTTTGTTCCCACGGAGAATCCGACGGGT TGTTACTCGCTCACATTTAATGTTGATGAAA GCTGGCTACAGGAAGGCCAGACGCGAATTAT TTTTGATGGCGTTAACTCGGCGTTTCATCTG TGGTGCAACGGGCGCTGGGTCGGTTACGGCC AGGACAGTCGTTTGCCGTCTGAATTTGACCT GAGCGCATTTTTACGCGCCGGAGAAAACCGC CTCGCGGTGATGGTGCTGCGCTGGAGTGACG GCAGTTATCTGGAAGATCAGGATATGTGGCG GATGAGCGGCATTTTCCGTGACGTCTCGTTG CTGCATAAACCGACTACACAAATCAGCGATT TCCATGTTGCCACTCGCTTTAATGATGATTT CAGCCGCGCTGTACTGGAGGCTGAAGTTCAG ATGTGCGGCGAGTTGCGTGACTACCTACGGG TAACAGTTTCTTTATGGCAGGGTGAAACGCA GGTCGCCAGCGGCACCGCGCCTTTCGGCGGT GAAATTATCGATGAGCGTGGTGGTTATGCCG ATCGCGTCACACTACGTCTGAACGTCGAAAA CCCGAAACTGTGGAGCGCCGAAATCCCGAAT CTCTATCGTGCGGTGGTTGAACTGCACACCG CCGACGGCACGCTGATTGAAGCAGAAGCCTG CGATGTCGGTTTCCGCGAGGTGCGGATTGAA *AATGGT*CTGCTGCTGCTGAACGGCAAGCCGT TGCTGATTCGAGGCGTTAACCGTCACGAGCA TCATCCTCTGCATGGTCAGGTCATGGATGAG CAGACGATGGTGCAGGATATCCTGCTGATGA AGCAGACAACTTTAAGCCGTGCGCTGTTTC GCATTATCCGAACCATCCGCTGTGGTACACG CTGTGCGACCGCTACGGCCTGTATGTGGTGG ATGAAGCCAATATTGAAACCCACGGCATGGT GCCAATGAATCGTCTGACCGATGATCCGCGC TGGCTACCGGCGATGAGCGAACGCGTAACGC GAATGGTGCAGCGCGATCGTAATCACCCGAG TGTGATCATCTGGTCGCTGGGGAATGAATCA GGCCACGGCGCTAATCACGACGCGCTGTATC GCTGGATCAAATCTGTCGATCCTTCCCGCCC GGTGCAGTATGAAGGCGGCGGAGCCGACACC ACGGCCACCGATATTATTTGCCCGATGTACG CGCGCGTGGATGAAGACCAGCCCTTCCCGGC TGTGCCGAAATGGTCCATCAAAAAATGGCTT TCGCTACCTGGAGAGACGCGCCCGCTGATCC TTTGCGAATACGCCCACGCGATGGGTAACAG TCTTGGCGGTTTCGCTAAATACTGGCAGGCG TTTCGTCAGTATCCCCGTTTACAGGGCGGCT TCGTCTGGGACTGGGTGGATCAGTCGCTGAT TAAATATGATGAAAACGGCAACCCGTGGTCG GCTTACGGCGGTGATTTTGGCGATACGCCGA ACGATCGCCAGTTCTGTATGAACGGTCTGGT CTTTGCCGACCGCACGCCGCATCCAGCGCTG ACGGAAGCAAAACACCAGCAGCAGTTTTTCC AGTTCCGTTTATCCGGGCAAACCATCGAAGT GACCGAATACCTGTTCCGTCATAGCGAT AACGAGCTCCTGCACTGGATGGTGGCGCTGG ATGGTAAGCCGCTGGCAAGCGGTGAAGTGCC TCTGGATGTCGCTCCACAAGGTAAA*CAGTT* GATTGAACTGCCTGAACTACCGCAGCCGGAG |

TABLE 9-continued

Sequence identities of LacZ fragments and sticky end motifs.

| Sequence identity | Sequence name | Sequence |
|---|---|---|
| | | AGCGCCGGGCAACTCTGGCTCACAGTACGCG<br>TAGTGCAACCGAACGCGACCGCATGGTCAGA<br>AGCCGGGCACATCAGCGCCTGGCAGCAGTGG<br>CGTCTGGCGGAAAACCTCAGTGTGACGCTCC<br>CCGCCGCGTCCCACGCCATCCCGCATCTGAC<br>CACCAGCGAAATGGATTTTTGCATCGAGCTG<br>GGTAATAAGCGTTGGCAATTTAACCGCCAGT<br>CAGGCTTTCTTTCACAGATGTGGATTGGCGA<br>TAAAAAACAACTGCTGACGCCGCTGCGCGAT<br>CAGTTCACCCGTGCACCGCTGGATAACGACA<br>TTGGCGTAAGTGAAGCGACCCGCATTGACCC<br>TAACGCCTGGGTCGAACGCTGGAAGGCGGCG<br>GGCCATTACCAGGCCGAAGCAGCGTTGTTGC<br>AGTGCACGGCAGATACACTTGCTGATGCGGT<br>GCTGATTACGACCGCTCACGCGTGGCAGCAT<br>CAGGGGAAAACCTTATTTATCAGCCGGAAAA<br>CCTACCGGATTGATGGTAGTGGTCAAATGGC<br>GATTACCGTTGATGTTGAAGTGGCGAGCGAT<br>ACACCGCATCCGGCGCGGATTGGCCTGAACT<br>GCCAGCTGGCGCAGGTAGCAGAGCGGGTAAA<br>CTGGCTCGGATTAGGGCCGCAAGAAAACTAT<br>CCCGACCGCCTTACTGCCGCCTGTTTTGACC<br>GCTGGGATCTGCCATTGTCAGACATGTATAC<br>CCCGTACGTCTTCCCGAGCGAAAACGGTCTG<br>CGCTGCGGGACGCGCGAATTGAATTATGGCC<br>CACACCAGTGGCGCGGCGACTTCCAGTTCAA<br>CATCAGCCGCTACAGTCAACAGCAACTGATG<br>GAAACCAGCCATCGCCATCTGCTGCACGCGG<br>AAGAAGGCACATGGCTGAATATCGACGGTTT |

TABLE 9-continued

Sequence identities of LacZ fragments and sticky end motifs.

| Sequence identity | Sequence name | Sequence |
|---|---|---|
| | | CCATATGGGGATTGGTGGCGACGACTCCTGG<br>AGCCCGTCAGTATCGGCGGAATTCCAGCTGA<br>GCGCCGGTCGCTACCATTACCAGTTGGTCTG<br>GTGTCAAAAATAAA*TATGT* |

LacZ fragments 1-3 were assembled from smaller, synthesized oligonucleic acids. During fragment preparation, the 5' and/or 3' of each fragment end was appended with a connecting adaptor to generated adaptor-modified fragments 1-3. To prepare LacZ for assembly with the precursor plasmid fragments, the 5' end of fragment 1 and the 3' end of fragment 3 were appended with a first outer adaptor comprising outer adaptor motif 1 (AGCCAT, SEQ ID NO.: 66) and a second outer adaptor comprising outer adaptor motif 2 (TTATGT, SEQ ID NO.: 67), respectively. The sequences of modified fragments 1-3 are shown in Table 10. Each modified fragment comprises a first adaptor sequence (GTATGCTGACTGCT, SEQ ID NO.: 68) at the first end and second adaptor sequence (TTGCCCTACGGTCT, SEQ ID NO.: 69) at the second end, indicated by a dashed underline. Each modified fragment comprises a nicking enzyme recognition site (GCAATG, SEQ ID NO.: 59), indicated by a dotted underline. Each modified fragment comprises an ANNNNT motif (SEQ ID NO.: 2), indicated by italics.

TABLE 10

Sequence identities of modified LacZ fragments.

| Sequence identity | Sequence name | Sequence |
|---|---|---|
| SEQ ID NO.: 70 | modified fragment 1 | GGACTT<u>GTATGCTGACTGCT</u>GCAATG*AGCCA*TATGACCATGA<br>TTACGGATTCACTGGCCGTCGTTTTACAACGTCGTGACTGGG<br>AAAACCCTGGCGTTACCCAACTTAATCGCCTTGCAGCACATC<br>CCCCTTTCGCCAGCTGGCGTAATAGCGAAGAGGCCCGCACCG<br>ATCGCCCTTCCCAACAGTTGCGCAGCCTGAATGGCGAATGGC<br>GCTTTGCCTGGTTTCCGGCACCAGAAGCGGTGCCGGAAAGCT<br>GGCTGGAGTGCGATCTTCCTGAGGCCGATACTGTCGTCGTCC<br>CCTCAAACTGGCAGATGCACGGTTACGATGCGCCCATCTACA<br>CCAACGTGACCTATCCCATTACGGTCAATCCGCCGTTTGTTCC<br>CACGGAGAATCCGACGGGTTGTTACTCGCTCACATTTAATGT<br>TGATGAAAGCTGGCTACAGGAAGGCCAGACGCGAATTATTTT<br>TGATGGCGTTAACTCGGCGTTTCATCTGTGGTGCAACGGGCG<br>CTGGGTCGGTTACGGCCAGGACAGTCGTTTGCCGTCTGAATT<br>TGACCTGAGCGCATTTTACGCGCCGGAGAAAACCGCCTCGC<br>GGTGATGGTGCTGCGCTGGAGTGACGGCAGTTATCTGGAAGA<br>TCAGGATATGTGGCGGATGAGCGGCATTTTCCGTGACGTCTC<br>GTTGCTGCATAAACCGACTACACAAATCAGCGATTTCCATGT<br>TGCCACTCGCTTTAATGATGATTTCAGCCGCGCTGTACTGGA |

TABLE 10-continued

Sequence identities of modified LacZ fragments.

| Sequence identity | Sequence name | Sequence |
|---|---|---|
| | | GGCTGAAGTTCAGATGTGCGGCGAGTTGCGTGACTACCTACG |
| | | GGTAACAGTTTCTTTATGGCAGGGTGAAACGCAGGTCGCCAG |
| | | CGGCACCGCGCCTTTCGGCGGTGAAATTATCGATGAGCGTGG |
| | | TGGTTATGCCGATCGCGTCACACTACGTCTGAACGTCGAAAA |
| | | CCCGAAACTGTGGAGCGCCGAAATCCCGAATCTCTATCGTGC |
| | | GGTGGTTGAACTGCACACCGCCGACGGCACGCTGATTGAAGC |
| | | AGAAGCCTGCGATGTCGGTTTCCGCGAGGTGCGGATTGAAAA |
| | | *TGGT*CATTGCAGACCGTAGGGCAATGATTC |
| SEQ ID NO.: 71 | modified fragment 2 | GGACTT<u>GTATGCTGACTGCTGCAATGAA</u>*TGGT*CTGCTGCTGCT |
| | | GAACGGCAAGCCGTTGCTGATTCGAGGCGTTAACCGTCACGA |
| | | GCATCATCCTCTGCATGGTCAGGTCATGGATGAGCAGACGAT |
| | | GGTGCAGGATATCCTGCTGATGAAGCAGAACAACTTTAACGC |
| | | CGTGCGCTGTTCGCATTATCCGAACCATCCGCTGTGGTACAC |
| | | GCTGTGCGACCGCTACGGCCTGTATGTGGTGGATGAAGCCAA |
| | | TATTGAAACCCACGGCATGGTGCCAATGAATCGTCTGACCGA |
| | | TGATCCGCGCTGGCTACCGGCGATGAGCGAACGCGTAACGC |
| | | GAATGGTGCAGCGCGATCGTAATCACCCGAGTGTGATCATCT |
| | | GGTCGCTGGGGAATGAATCAGGCCACGGCGCTAATCACGAC |
| | | GCGCTGTATCGCTGGATCAAATCTGTCGATCCTTCCCGCCCG |
| | | GTGCAGTATGAAGGCGGCGGAGCCGACACCACGGCCACCGA |
| | | TATTATTTGCCCGATGTACGCGCGCGTGGATGAAGACCAGCC |
| | | CTTCCCGGCTGTGCCGAAATGGTCCATCAAAAAATGGCTTTC |
| | | GCTACCTGGAGAGACGCGCCCGCTGATCCTTTGCGAATACGC |
| | | CCACGCGATGGGTAACAGTCTTGGCGGTTTCGCTAAATACTG |
| | | GCAGGCGTTTCGTCAGTATCCCCGTTTACAGGGCGGCTTCGT |
| | | CTGGGACTGGGTGGATCAGTCGCTGATTAAATATGATGAAAA |
| | | CGGCAACCCGTGGTCGGCTTACGGCGGTGATTTTGGCGATAC |
| | | GCCGAACGATCGCCAGTTCTGTATGAACGGTCTGGTCTTTGC |
| | | CGACCGCACGCCGCATCCAGCGCTGACGGAAGCAAAACACC |
| | | AGCAGCAGTTTTTCCAGTTCCGTTTATCCGGGCAAACCATCG |
| | | AAGTGACCAGCGAATACCTGTTCCGTCATAGCGATAACGAGC |
| | | TCCTGCACTGGATGGTGGCGCTGGATGGTAAGCCGCTGGCAA |
| | | GCGGTGAAGTGCCTCTGGATGTCGCTCCACAAGGTAAA*CAGT* |
| | | <u>*TC*ATTGCAGACCGTAGGGCAATGATTC</u> |
| SEQ ID NO.: 72 | modified fragment 3 | GGACTT<u>GTATGCTGACTGCTGCAATGA</u>*CAGTT*GATTGAACTGC |
| | | CTGAACTACCGCAGCCGGAGAGCGCCGGGCAACTCTGGCTC |

TABLE 10-continued

Sequence identities of modified LacZ fragments.

| Sequence identity | Sequence name | Sequence |
|---|---|---|
| | | ACAGTACGCGTAGTGCAACCGAACGCGACCGCATGGTCAGA |
| | | AGCCGGGCACATCAGCGCCTGGCAGCAGTGGCGTCTGGCGG |
| | | AAAACCTCAGTGTGACGCTCCCCGCCGCGTCCCACGCCATCC |
| | | CGCATCTGACCACCAGCGAAATGGATTTTTGCATCGAGCTGG |
| | | GTAATAAGCGTTGGCAATTTAACCGCCAGTCAGGCTTTCTTT |
| | | CACAGATGTGGATTGGCGATAAAAAACAACTGCTGACGCCG |
| | | CTGCGCGATCAGTTCACCCGTGCACCGCTGGATAACGACATT |
| | | GGCGTAAGTGAAGCGACCCGCATTGACCCTAACGCCTGGGTC |
| | | GAACGCTGGAAGGCGGCGGGCCATTACCAGGCCGAAGCAGC |
| | | GTTGTTGCAGTGCACGGCAGATACACTTGCTGATGCGGTGCT |
| | | GATTACGACCGCTCACGCGTGGCAGCATCAGGGGAAAACCTT |
| | | ATTTATCAGCCGGAAAACCTACCGGATTGATGGTAGTGGTCA |
| | | AATGGCGATTACCGTTGATGTTGAAGTGGCGAGCGATACACC |
| | | GCATCCGGCGCGGATTGGCCTGAACTGCCAGCTGGCGCAGGT |
| | | AGCAGAGCGGGTAAACTGGCTCGGATTAGGGCCGCAAGAAA |
| | | ACTATCCCGACCGCCTTACTGCCGCCTGTTTTGACCGCTGGG |
| | | ATCTGCCATTGTCAGACATGTATACCCCGTACGTCTTCCCGA |
| | | GCGAAAACGGTCTGCGCTGCGGGACGCGCGAATTGAATTAT |
| | | GGCCCACACCAGTGGCGCGGCGACTTCCAGTTCAACATCAGC |
| | | CGCTACAGTCAACAGCAACTGATGGAAACCAGCCATCGCCAT |
| | | CTGCTGCACGCGGAAGAAGGCACATGGCTGAATATCGACGG |
| | | TTTCCATATGGGGATTGGTGGCGACGACTCCTGGAGCCCGTC |
| | | AGTATCGGCGGAATTCCAGCTGAGCGCCGGTCGCTACCATTA |
| | | CCAGTTGGTCTGGTGTCAAAAATAAA*TATGT*CATTGCAGACCG |
| | | TAGGGCAATGATTC |

To generate a second nicking enzyme recognition site, a non-canonical base uracil, each modified fragment was amplified using the universal primers shown in Table 11. An asterisk indicates a phosphorothioated bond.

TABLE 11

Uracil-containing universal primers for amplification of modified LacZ fragments.

| Sequence identity | Sequence name | Sequence |
|---|---|---|
| SEQ ID NO.: 73 | modfrag1F | GTATGCTGACTGCTGCAATG AGCCA*/3deoxyU/ |
| SEQ ID NO.: 74 | modfrag1R | TTGCCCTACGGTCTGCAATG ACCAT*/3deoxyU/ |
| SEQ ID NO.: 75 | modfrag2F | GTATGCTGACTGCTGCAATG AATGG*/3deoxyU/ |
| SEQ ID NO.: 76 | modfrag2R | TTGCCCTACGGTCTGCAATG AACTG*/3deoxyU/ |
| SEQ ID NO.: 77 | modfrag3F | GTATGCTGACTGCTGCAATG ACAGT*/3deoxyU/ |
| SEQ ID NO.: 78 | modfrag3R | TTGCCCTACGGTCTGCAATG ACATA*/3deoxyU/ |

Each primer set comprises, in 5' to 3' order: adaptor sequence, a first nicking enzyme recognition site (GCAATG, SEQ ID NO.: 59), and a sticky end motif comprising a non-canonical base (ANNNNU, SEQ ID NO.: 53). Modified fragments 1-3 were amplified using their corresponding primers modfrag1F/modfrag1R, modfrag2F/modfrag2R and modfrag3F/modfrag3R, respectively. The composition of the amplification reaction is shown in Table 12. The amplification reaction conditions are shown in Table 13.

TABLE 12

PCR reaction mixture for amplification of modified LacZ fragments.

| PCR component | Quantity (µL) | Concentration in mixture |
|---|---|---|
| Phusion U (2 U/µL) | 1 | 1 U/50 µL |
| 5x Phusion HF buffer | 20 | 1x |
| 10 mM dNTP | 2 | 200 µM |
| Plasmid template (50 pg/µL) | 2 | 100 pg/100 µL |
| Forward primer (200 µM) | 0.25 | 0.5 µM |
| Forward primer (200 µM) | 0.25 | 0.5 µM |
| Water | 70.5 | |

TABLE 13

PCR reaction conditions for amplification of modified LacZ fragments

| Step | Cycle |
|---|---|
| 1 | 1 cycle: 98° C., 30 sec |
| 2 | 20 cycles: 98° C., 10 sec; 72° C., 30 sec |
| 3 | 10 cycles: 98° C., 10 sec; 72° C., 45 sec |
| 4 | 1 cycle: 72° C., 5 min |
| 5 | Hold: 4° C., 15-30 sec per kb |

Assembly of LacZ Precursor Fragments

Figure 11:
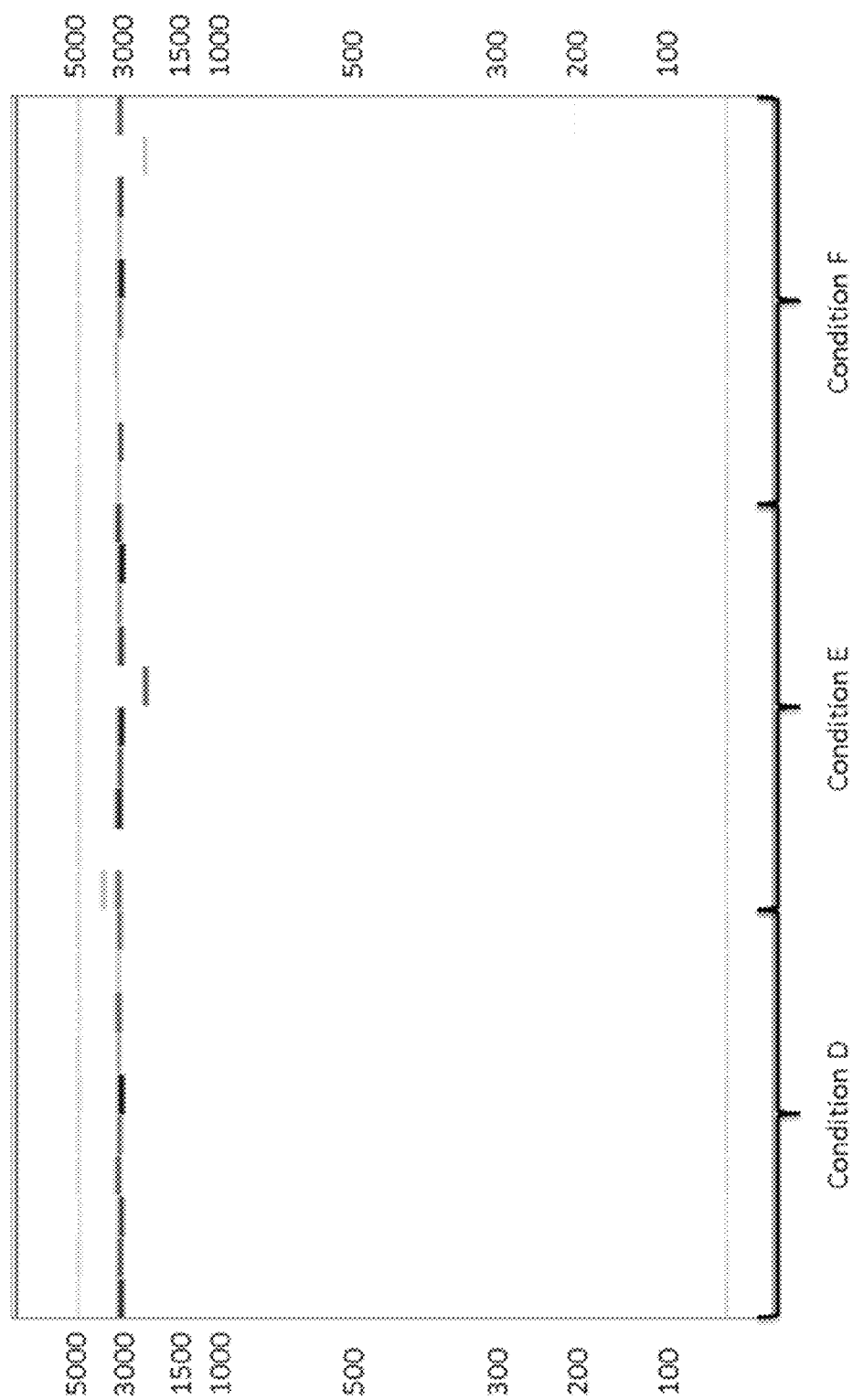
FIG. 11 shows an image of an electrophoresis gel resolving amplicons of a LacZ gene assembled in a plasmid using scar-free assembly methods described herein.

LacZ precursor fragments were annealed and ligated with the plasmid fragment according to reactions 1 and 2 under conditions A-I shown in Table 14. The nicking enzyme Nb.BsrDI was used to generate a nick adjacent to the nicking recognition site (GCAATG, SEQ ID NO.: 59) on one strand during reaction 1. USER (UDG and endonuclease VIII) was used to generate a nick at uracil in a second strand during reaction 2. Reaction 2 comprised three steps: cleavage of uracil, ligation, and enzymatic inactivation. Assembled fragments comprise LacZ inserted into the 5 kb plasmid. To determine efficiency of assembly into the plasmid, PCR of colonies resulting from the transformation of assembled plasmids into E. coli were amplified using plasmid-specific primers. Amplification products from 10 colonies of conditions A-I were amplified by colony PCR. The number amplicons with the correct size insert (about 3 kb), as identified by gel electrophoresis, are shown in Table 14. FIG. 11 shows an image of a gel electrophoresis of LacZ amplified inserts generated from assembly conditions A-I.

TABLE 14

LacZ fragment efficiency assembly analysis.

| Condition | Precursor fragments | Reaction 1 | Reaction 2 | Predicted insert size confirmed by electrophoresis |
|---|---|---|---|---|
| A | LacZ precursor fragments 1-3; plasmid precursor fragment A | Incubate fragments with nicking enzyme Nb.BsrDI and buffer at 65° C. for 60 min | Incubate reaction 1 with USER, ATP, T7 ligase, and buffer at 37° C. for 30 min, 16° C. for 60 min, and 80° C. for 20 min | 4/10 |
| B | LacZ precursor fragments 1-3; plasmid precursor fragment A | Incubate fragments with nicking enzyme Nb.BsrDI and buffer at 65° C. for 60 min | Incubate reaction 1 with USER, ATP, T7 ligase, and buffer at 37° C. for 30 min, 16° C. for 60 min, and 80° C. for 20 min | 9/10 |
| C | LacZ precursor fragments 1-3; plasmid precursor fragment A | Incubate fragments with nicking enzyme Nb.BsrDI and buffer at 65° C. for 60 min | Incubate reaction 1 with USER, ATP, T7 ligase, and buffer at 37° C. for 30 min, 16° C. for 60 min, and 80° C. for 20 min | 8/10 |
| D | LacZ precursor fragments 1-3; plasmid precursor fragment A | Incubate fragments with nicking enzyme Nb.BsrDI and buffer at 65° C. for 60 min | Incubate reaction 1 with USER, ATP, T7 ligase, and buffer at 60° C. for 30 min, 20 cycles of 37° C. for 1 min and 16° C. for 3 min, 80° C. for 20 min, 4° C. hold | 10/10 |
| E | LacZ precursor fragments 1-3; plasmid precursor fragment A | Incubate fragments with nicking enzyme Nb.BsrDI and buffer at 65° C. for 60 min | Incubate reaction 1 with USER, ATP, T7 ligase, and buffer at 60° C. for 30 min, 20 cycles of 37° C. for 1 min and 16° C. for 3 min, 80° C. for 20 min, 4° C. hold | 7/10 |
| F | LacZ precursor fragments 1-3; plasmid precursor fragment A | Incubate fragments with nicking enzyme Nb.BsrDI and buffer at 65° C. for 60 min | Incubate reaction 1 with USER, ATP, T7 ligase, and buffer at 60° C. for 30 min, 20 cycles of 37° C. for 1 min and 16° C. for 3 min, 80° C. for 20 min, 4° C. hold | 9/10 |
| G | LacZ precursor fragments 1-3; plasmid precursor Nb.BsrDI, ATP and | Incubate fragments with nicking enzyme | Incubate reaction 1 with USER, T7 ligase, and buffer at 37° C. for 60 min, 16° C. for 60 | 0/10 |

TABLE 14-continued

LacZ fragment efficiency assembly analysis.

| Condition | Precursor fragments | Reaction 1 | Reaction 2 | Predicted insert size confirmed by electrophoresis |
|---|---|---|---|---|
| | fragment B | buffer at 65° C. for 60 min | min, and 80° C. for 20 min | |
| H | plasmid precursor fragment A | Incubate fragments with nicking enzyme Nb.BsrDI and buffer at 65° C. for 60 min | Incubate reaction 1 with USER, ATP, T7 ligase, and buffer at 37° C. for 60 min, 16° C. for 60 min, and 80° C. for 20 min | 0/4 |
| I | plasmid precursor fragment B | Incubate fragments with nicking enzyme Nb.BsrDI and buffer at 65° C. for 60 min | Incubate reaction 1 with USER, ATP, T7 ligase, and buffer at 37° C. for 60 min, 16° C. for 60 min, and 80° C. for 20 min | 0/4 |

Example 3: Recombinatorial Target Nucleic Acid Library

An enzyme of interest having an activity to be improved is selected. Specific amino acid residues relevant to enzyme activity and stability are identified. The nucleic acid sequence encoding the enzyme is obtained. Bases corresponding to the specific amino acid residues are identified, and the nucleic acid is partitioned into fragments such that each fragment spans a single base position corresponding to a specific amino acid residue.

Target nucleic acid fragments are synthesized such that identified bases corresponding to the specific amino acid residues are indeterminate. Target nucleic acid fragments are amplified using a uridine primer and treated with a sequence adjacent nick enzyme and a uridine-specific nick enzyme. Cleaved end sequence is removed and target nucleic acid fragments are assembled to generate a target nucleic acid library. Aliquots of the library are sequenced to confirm success of the assembly, and aliquoted molecules of the library are individually cloned and transformed into a host cell for expression. Expressed enzymes are isolated and assayed for activity and stability.

Enzymes having increased stability due to single point mutations are identified. Enzymes having increased activity due to single point mutations are identified. Also identified are enzymes having increased stability and/or activity due to combinations of point mutations, each of which individually is detrimental to enzyme activity or stability, and which would be unlikely to be pursued by more traditional, 'one mutation at a time' approaches.

Example 4: De Novo Generation of a Target Nucleic Acid

A 3 kb double-stranded target gene of predetermined sequence is prepared using a de novo synthesis and assembly method described herein. The predetermined gene sequence is first analyzed to identify fragments which will be synthesized and assembled into the final gene product.

Determination of Gene Fragment Sequences

The target nucleic acid sequence is analyzed to identify sticky end motifs having an ANNNNT sequence (SEQ ID NO.: 2). Two of the identified motifs are selected according to their position in the sequence, so that the first identified motif is located at roughly 1 kb and the second identified motif is located at roughly 2 kb. The two selected motifs thus partition the target sequence into three, approximately 1 kb precursor fragments, denoted fragments 1, 2 and 3.

De Novo Synthesis of Precursor Fragments

Fragments 1, 2 and 3 are prepared by de novo synthesis and PCA assembly of oligonucleic acids. During this process, outer adaptor sequences are added to the 5' end of fragment 1 and the 3' end of fragment 3, and connecting adaptor sequences are added to the 3' end of fragment 1, the 5' and 3' ends of fragment 2, and the 5' end of fragment 3. The connecting adaptor sequences located at the 3' end of fragment 1 and the 5' end of fragment 2 comprise the sequence of the first identified ANNNNT motif (SEQ ID NO.: 2). The connecting adaptor sequences located at the 3' end of fragment 2 and the 5' end of fragment 3 comprise the sequence of the second identified ANNNNT motif (SEQ ID NO.: 2). Each connecting adaptor comprises, in order: a sequence of 1-10 bases (adaptor bases), a first nicking enzyme recognition site comprising a first nicking enzyme cleavage site on one strand, and a sticky end motif. The adaptor bases and first nicking enzyme cleavage site comprise the same bases for each connecting adaptor.

Fragment 1 prepared with adaptor sequence comprises, in 5' to 3' order: a first outer adaptor sequence; fragment 1 sequence; and a first connecting adaptor sequence comprising, in 5' to 3' order, the first ANNNNT motif (SEQ ID NO.: 2), the first nicking enzyme recognition site comprising the first nicking enzyme cleavage site on a first strand, and the sequence of adaptor bases. Fragment 2 prepared with adaptor sequence comprises, in 5' to 3' order: the first connecting adaptor sequence comprising, in 5' to 3' order, the sequence of adaptor bases, the first nicking enzyme recognition site comprising the first nicking enzyme cleavage site on a second strand, and the first ANNNNT motif (SEQ ID NO.: 2); fragment 2 sequence; and a second connecting adaptor sequence comprising, in 5' to 3' order, the second ANNNNT motif (SEQ ID NO.: 2), the first nicking enzyme recognition site comprising the first nicking enzyme cleavage site on a first strand, and the sequence of adaptor bases. Fragment 3 prepared with adaptor sequence comprises, in 5' to 3' order: the second connecting adaptor sequence comprising, in 5' to 3' order, the sequence of adaptor bases, the first nicking enzyme recognition site comprising the first nicking enzyme cleavage site on a second strand, the second ANNNNT motif (SEQ ID NO.: 2); fragment 3 sequence; and a second outer adaptor sequence.

Generation of Fragments with Two Nicking Enzyme Cleavage Sites

Each of the prepared fragments are amplified to incorporate a second nicking enzyme cleavage site on a single-strand of each fragment such that the second nicking enzyme cleavage site is located from 1 to 10 bases away from the first nicking enzyme cleavage site of each fragment and on a different strand from the first nicking enzyme cleavage site. The second nicking enzyme cleavage site comprises a non-canonical base. The non-canonical base is added to each fragment during PCR via a primer comprising the sequence of adaptor bases, the first nicking enzyme recognition site, a sticky end motif ANNNNT (SEQ ID NO.: 2), and the non-canonical base.

Fragment 1 comprises, in 5' to 3' order: the first outer adaptor sequence, fragment 1 sequence, the non-canonical base on the second strand, the first ANNNNT motif (SEQ ID NO.: 2), the first nicking enzyme recognition site comprising the first nicking enzyme cleavage site on the first strand, and the sequence of adaptor bases. Fragment 2 comprises, in 5' to 3' order: the sequence of adaptor bases, the first nicking enzyme recognition site comprising the first nicking enzyme cleavage site on the second strand, the first ANNNNT motif (SEQ ID NO.: 2), the non-canonical base on the first strand, fragment 2 sequence, the non-canonical base on the second strand, the ANNNNT motif (SEQ ID NO.: 2), the first nicking enzyme recognition site comprising the first nicking enzyme cleavage site on the first strand, and the sequence of adaptor bases. Fragment 3 comprises, in 5' to 3' order: the sequence of adaptor bases, the first nicking enzyme recognition site comprising the first nicking enzyme cleavage site on the second strand, the second ANNNNT motif (SEQ ID NO.: 2), the non-canonical base on the first strand, fragment 3 sequence, and a second outer adaptor sequence.

Cleavage of Fragments with Two Nicking Enzymes

Each of the three fragments comprising two nicking enzyme cleavage sites are treating with a first nicking enzyme and a second nicking enzyme. The first nicking enzyme creates a nick at the first nicking enzyme cleavage site by cleaving a single-strand of the fragment. The second nicking enzyme creates a nick by removing the non-canonical base from the fragment. The enzyme-treated fragments have an overhang comprising a sticky end motif ANNNNT (SEQ ID NO.: 2).

Enzyme-treated fragment 1 comprises, in 5' to 3' order: the first outer adaptor, fragment 1 sequence, and on the first strand, the first sticky end motif ANNNNT (SEQ ID NO.: 2). Enzyme-treated fragment 2 comprises, in 5' to 3' order: on the second strand, the first sticky end motif ANNNNT (SEQ ID NO.: 2); fragment 2 sequence; and on the first strand, the second sticky end motif ANNNNT (SEQ ID NO.: 2). Enzyme-treated fragment 3 comprises, in 5' to 3' order: on the second strand, the second sticky end motif ANNNNT (SEQ ID NO.: 2); fragment 3 sequence; and the second outer adaptor.

Assembly of Cleaved Fragments

The first sticky ends of fragments 1 and 2 are annealed and the second sticky ends of fragments 2 and 3 are annealed, generating a gene comprising, in 5' to 3' order: the first outer adaptor, fragment 1 sequence, the first sticky end motif, fragment 2 sequence, the second sticky end motif, fragment 3 sequence, and the second outer adaptor. The assembled product comprises the predetermined sequence of the target gene without any scar sites. The assembled product is amplified using primers to the outer adaptors to generate desired quantities of the target gene.

Example 5: Generation of Precursor Nucleic Acid Fragments Using Uracil as a Non-Canonical Base A double-stranded target gene of predetermined sequence is prepared using a de novo synthesis and assembly method described herein. The predetermined gene sequence is first analyzed to identify fragments which will be synthesized and assembled into the final gene product.

Determination of Gene Fragment Sequences

The target nucleic acid sequence is analyzed to identify sticky end motifs. Three of the identified motifs are selected according to their position in the sequence, so that the motifs partition the predetermined sequence in four fragments having roughly similar sequence lengths. The sticky end motifs are designated sticky end motif x, sticky end motif y, and sticky end motif z. The precursor fragments are designed fragment 1, fragment 2, fragment 3, and fragment 4. Accordingly, the predetermined sequence comprises, in order: fragment 1 sequence, sticky end motif x, fragment 2 sequence, sticky end motif y, fragment 3 sequence, sticky end motif z, and fragment 4 sequence.

De Novo Synthesis of Precursor Fragments

Fragments 1-4 are prepared by de novo synthesis and PCA assembly of oligonucleic acids. During this process connecting adaptor sequences are added to the 3' end of fragment 1, the 5' and 3' ends of fragments 2 and 3, and the 5' end of fragment 4. The connecting adaptor sequences located at the 3' end of fragment 1 and the 5' end of fragment 2 comprise sticky end motif x. The connecting adaptor sequences located at the 3' end of fragment 2 and the 5' end of fragment 3 comprise sticky end motif y. The connecting adaptor sequences located at the 3' end of fragment 3 and the 5' end of fragment 4 comprise sticky end motif z. Each connecting adaptor comprises, in order: a sequence of 1-10 bases (adaptor bases), a first nicking enzyme recognition site comprising a first nicking enzyme cleavage site on a first strand, a sticky end motif comprising a second nicking enzyme cleavage site on the 3' base of the second strand. The second nicking enzyme cleavage site comprises the non-canonical base uracil. The connecting adaptor sequences are positioned at the 5' and/or 3' end of a fragment such that the 3' uracil of the connecting adaptor is positioned directed next to the 5' and/or 3' end of the fragment. The adaptor bases and first nicking enzyme cleavage site comprise the same bases for each connecting adaptor.

Precursor fragment 1 comprises fragment 1 sequence and a first connecting adaptor comprising sticky end motif x. Precursor fragment 2 comprises the first connecting adaptor comprising sticky end motif x, fragment 2 sequence, and a second connecting adaptor comprising sticky end motif y. Precursor fragment 3 comprises the second connecting adaptor comprising sticky end motif y, fragment 3 sequence, and a third connecting adaptor comprising sticky end motif z. Precursor fragment 4 comprises the third connecting adaptor comprising sticky end motif z and fragment 4 sequence.

Cleavage of Fragments with Two Nicking Enzymes

Each of the four precursor fragments comprise one or two connecting adaptors, each connecting adaptor comprising: a first nicking enzyme recognition site comprising a first nicking enzyme cleavage site on a first strand, and uracil base on the second strand. The precursor fragments are treating with a first nicking enzyme which recognizes the first nicking enzyme recognition site to generate a nick at the first nicking enzyme cleavage site. The precursor fragments are treated with a second nicking enzyme, USER, which excises the uracil from the second strand, generating a nick where the uracil used to reside. USER comprises Uracil DNA glycosylase (UDG) and DNA glycosylase-lyase Endonuclease VIII (EndoVIII). Each precursor fragment now comprises an overhang consisting of a sticky end motif.

Precursor fragment 1 now comprises fragment 1 sequence and a 5' overhang consisting of sequence motif x. Precursor fragment 2 now comprises a 3' overhang consisting of sequence motif x, fragment 2 sequence, and a 5' overhang consisting of sequence motif y. Precursor fragment 3 now comprises a 3' overhang consisting of sequence motif y, fragment 3 sequence, and a 5' overhang consisting of sequence motif z. Precursor fragment 4 now comprises a 3' overhang consisting of sequence motif z and fragment 4 sequence.

Assembly of Cleaved Fragments

The sticky end motif x overhangs of precursor fragments 1 and 2 are annealed, the sticky end motif y overhangs of precursor fragments 2 and 3 are annealed, and the sticky end motif z overhangs of precursor fragments 3 and 4 are annealed, generating a gene comprising, in 5' to 3' order: fragment 1 sequence, sticky end motif x, fragment 2 sequence, sticky end motif y, fragment 3 sequence, sticky end motif z and fragment 4 sequence.

The product to be assembled comprises the predetermined sequence of the target gene without any scar sites. The assembled product is optionally amplified to generate desired quantities of the target gene. Alternatively, precursor fragments are generated at sufficient quantities such that amplification of the final gene is unnecessary. Such instances allow for the generation of large genes which are unable to be amplified using traditional amplification methods.

Example 6: Universal Primers to Introduce a Non-Canonical Base into a Precursor Nucleic Acid Fragment A population of precursor nucleic acid fragments are amplified using a set of universal primer pairs, wherein each universal primer introduces a non-canonical base uracil to a single-strand of a precursor nucleic acid.

Design of Universal Primers

A predetermined sequence of a target gene is analyzed to select sticky end motifs that partition the gene into precursor fragments of desired size. The sticky end motifs have the sequence ANNNNT (SEQ ID NO.: 2), where each selected sticky end motif has a different NNNN sequence. The NNNN sequence for each selected sticky end motif is noted.

Universal forward primers are synthesized to comprise, in 5' to 3' order: 1-20 forward adaptor bases, a nicking enzyme recognition site, and a sticky end motif comprising ANNNNU (SEQ ID NO.: 53). A subpopulation of forward primers is generated so that each subpopulation comprises a NNNN sequence of a different sticky end motif selected from the target gene.

Universal reverse primers are synthesized to comprise, in 5' to 3' order: 1-20 reverse adaptor bases, a nicking enzyme recognition site, and a sticky end motif comprising ANNNNU (SEQ ID NO.: 53). A subpopulation of reverse primers is generated so that each subpopulation comprises the reverse complement of a NNNN sequence of a different sticky end motif selected from the target gene.

The nicking enzyme recognition site sequence in the universal primers is designed such that when the universal primers are incorporated into precursor fragments during an amplification reaction, the reverse complement sequence of the nicking enzyme recognition site sequence in the universal primer comprises a nicking enzyme cleavage site. Accordingly, upon treating with a nicking enzyme specific for the nicking enzyme cleavage site, a nick is generated on a strand of the fragment not comprising the uracil base.

Amplification of Precursor Nucleic Acid Fragments with Universal Primers

Precursor fragments partitioned by the selected sticky end motifs are assembled from smaller, synthesized nucleic acids. The precursor fragments are amplified using the set of universal primers comprising the sticky end motif ANNNNT (SEQ ID NO.: 2), wherein the T is mutated with the non-canonical base uracil. The precursor fragments each comprise a nicking enzyme recognition site comprising a nicking enzyme cleavage site on one strand and a uracil base on the other strand.

Enzymatic Digestion of Precursor Fragments Amplified with Universal Primers

Precursor fragments amplified with universal primers are treated with a first nicking enzyme to create a nick at the nicking enzyme cleavage site and a second nicking enzyme comprising UDG and Endonuclease VIII activity to generate a nick at the uracil base site. The precursor fragments comprise overhangs with the sticky end motif ANNNNT (SEQ ID NO.: 2).

Assembly of Cleaved Fragments

Fragments comprising complementary overhangs are annealed to generate the target gene. The target gene comprises the predetermined sequence, with no extraneous scar sites.

Example 7: Assembly of a Target Gene Using Type II Restriction Endonucleases

A double-stranded target gene of predetermined sequence is prepared using a de novo synthesis and assembly method described herein. The predetermined gene sequence is first analyzed to identify fragments which will be synthesized and assembled into the final gene product.

Determination of Gene Fragment Sequences

The target nucleic acid sequence is analyzed to identify sticky end motifs having a Type II restriction endonuclease recognition sequence. Three of the identified motifs are selected according to their position in the sequence, so that the motifs partition the predetermined sequence in four fragments having roughly similar sequence lengths of about 200 kb. The sticky end motifs are designated sticky end motif x, sticky end motif y, and sticky end motif z. The precursor fragments are designed fragment 1, fragment 2, fragment 3, and fragment 4. Accordingly, the predetermined sequence comprises, in order: fragment 1 sequence, sticky end motif x, fragment 2 sequence, sticky end motif y, fragment 3 sequence, sticky end motif z, and fragment 4 sequence.

De Novo Synthesis of Precursor Fragments

Precursor fragments 1-4 are prepared by de novo synthesis and PCA assembly of oligonucleic acids. During this process connecting adaptor sequences are added to the 3' end of fragment 1, the 5' and 3' ends of fragments 2 and 3, and the 5' end of fragment 4. The connecting adaptor sequences located at the 3' end of fragment 1 and the 5' end of fragment 2 comprise sticky end motif x. The connecting adaptor sequences located at the 3' end of fragment 2 and the 5' end of fragment 3 comprise sticky end motif y. The connecting adaptor sequences located at the 3' end of fragment 3 and the 5' end of fragment 4 comprise sticky end motif z. Each connecting adaptor comprises a sequence of 1-10 adaptor bases and sticky end motif comprising a Type II restriction endonuclease recognition sequence. Also during preparation of precursor fragments 1-4, outer adaptors comprising 1-10 adaptor bases are added to the 5' and 3' ends of fragments 1 and 4, respectively. The adaptor bases comprise the same bases for each connecting adaptor and outer adaptor.

Precursor fragment 1 comprises outer adaptor sequence 1, fragment 1 sequence and a first connecting adaptor comprising sticky end motif x. Precursor fragment 2 comprises the first connecting adaptor comprising sticky end motif x, fragment 2 sequence, and a second connecting adaptor comprising sticky end motif y. Precursor fragment 3 comprises the second connecting adaptor comprising sticky end motif y, fragment 3 sequence, and a third connecting adaptor comprising sticky end motif z. Precursor fragment 4 comprises the third connecting adaptor comprising sticky end motif z, fragment 4 sequence, and outer adaptor sequence 2.

Cleavage of Fragments with Type II Restriction Enzymes

Each of the four precursor fragments comprise one or two connecting adaptors, each connecting adaptor having a sticky end motif comprising a Type II restriction endonuclease recognition sequence. The precursor fragments are treated with three Type II restriction enzymes, each enzyme specific for a Type II recognition sequence in sticky end motifs X-Z, to generate four precursor fragments with sticky ends.

Assembly of Cleaved Fragments

The sticky end motif x overhangs of precursor fragments 1 and 2 are annealed, the sticky end motif y overhangs of precursor fragments 2 and 3 are annealed, and the sticky end motif z overhangs of precursor fragments 3 and 4 are annealed, generating a gene comprising, in 5' to 3' order: fragment 1 sequence, sticky end motif x, fragment 2 sequence, sticky end motif y, fragment 3 sequence, sticky end motif z and fragment 4 sequence. The product to be assembled comprises the predetermined sequence of the target gene without any scar sites.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments described herein may be employed.

What is claimed is:

1. A method for nucleic acid assembly, the method comprising:

a) providing a predetermined nucleic acid sequence;

b) providing a plurality of precursor double-stranded nucleic acid fragments, each precursor double-stranded nucleic acid fragment having two strands, wherein each of the two strands comprises a sticky end sequence of 5'-A ($N^x$) T-3' (SEQ ID NO.: 1) or 5'-G ($N^x$)C-3' (SEQ ID NO.: 16), wherein N is a nucleotide, wherein x is the number of nucleotides between nucleotides A and T or between G and C, and wherein x is 1 to 10, and wherein no more than two precursor double-stranded nucleic acid fragments comprise the same sticky end sequence;

c) providing primers comprising a nicking endonuclease recognition site and a sequence comprising (i) 5'-A ($N^x$) U-3' (SEQ ID NO.: 80) corresponding to each of the different sticky end sequences of 5'-A ($N^x$) T-3'(SEQ ID NO.: 1) or (ii) 5'-G ($N^x$) U-3' (SEQ ID NO.: 81) corresponding to each of the different sticky end sequences of 5'-G ($N^x$)C-3' (SEQ ID NO.: 16);

d) performing a polynucleotide extension reaction to form a polynucleotide extension reaction product that is double-stranded nucleic acid fragments;
e) subjecting the polynucleotide extension reaction product to nicking and cleavage reactions to form double-stranded nucleic acid fragments with 3' overhangs; and
f) annealing the double-stranded nucleic acid fragments with 3' overhangs to form a nucleic acid encoding for the predetermined nucleic acid sequence that does not include the nicking endonuclease recognition site.

2. The method of claim 1, wherein x is 4, 5, or 6.

3. The method of claim 1, wherein the predetermined nucleic acid sequence is 1 kb to 100 kb in length.

4. The method of claim 1, wherein the plurality of precursor double-stranded nucleic acid fragments are each at least 100 bases in length.

5. The method of claim 1, wherein the sticky end sequences are each at least 4 bases long.

6. The method of claim 1, wherein step "c" further comprises providing (i) a forward primer comprising, in order 5' to 3': a first outer adaptor region and a nucleic acid sequence from a first terminal portion of the predetermined nucleic acid sequence; and (ii) a reverse primer, comprising, in order 5' to 3': a second outer adaptor region and a nucleic acid sequence from a second terminal portion of the predetermined nucleic acid sequence.

7. The method of claim 6, wherein the annealed double-stranded nucleic acid fragments comprise the first outer adaptor region and the second outer adapter region.

8. The method of claim 1, wherein the nicking and cleavage reactions comprise adding an enzyme that is a nicking endonuclease, N-glycosylase or AP-lyase.

9. The method of claim 8, wherein the enzyme is endonuclease VIII.

10. The method of claim 8, wherein the nicking endonuclease is Nb.BbvCI, Nb.BsmI, Nb.BsrDI, Nb.BtsI, Nt.AlwI, Nt.BbvCI, Nt.BsmAI, Nt.BspQI, Nt.BstNBI, or Nt.CviPII.

11. The method of claim 1, further comprising ligating the annealed double-stranded nucleic acid fragments.

12. The method of claim 1, wherein annealing comprises thermocycling between a maximum and a minimum temperature, thereby generating a first overhang from a first double-stranded DNA fragment and a second overhang from a second double-stranded DNA fragment, wherein the first and the second overhangs are complimentary, hybridizing the first and second overhangs to each other; and ligating.

13. The method of claim 1, wherein a polymerase lacking 3' to 5' proofreading activity is added during the polynucleotide extension reaction.

14. The method of claim 13, wherein the polymerase is a Family A polymerase or a Family B high fidelity polymerase engineered to tolerate base pairs comprising uracil.

15. The method of claim 1, wherein the plurality of precursor double-stranded nucleic acid fragments comprise an adaptor sequence comprising the nicking endonuclease recognition site.

16. The method of claim 1, wherein one or more of the plurality of precursor double-stranded nucleic acid fragments is a linear vector sequence.

17. A method for nucleic acid assembly, the method comprising:
a) providing a predetermined nucleic acid sequence;
b) synthesizing a plurality of precursor double-stranded nucleic acid fragments, each precursor double-stranded nucleic acid fragment having two strands, wherein each of the two strands comprises a sticky end sequence of 5'-A (Nx) T-3' (SEQ ID NO.: 1) or 5'-G (Nx)C-3' (SEQ ID NO.: 16), wherein N is a nucleotide, wherein x is the number of nucleotides between nucleotides A and T or between G and C, and wherein x is 1 to 10, and wherein no more than two precursor double-stranded nucleic acid fragments comprise the same sticky end sequence;
c) providing primers comprising a nicking endonuclease recognition site and a sequence comprising (i) 5'-A (Nx) M-3' (SEQ ID NO.: 82) corresponding to each of the different sticky end sequences of 5'-A (Nx) T-3' (SEQ ID NO.: 1) or (ii) 5'-G (Nx) M-3' (SEQ ID NO.: 83) corresponding to each of the different sticky end sequences of 5'-G (Nx)C-3' (SEQ ID NO.: 16), wherein M is a non-canonical base, wherein the primers are each 7 to 70 bases in length;
d) performing a polynucleotide extension reaction to form a polynucleotide extension reaction product that is double-stranded nucleic acid fragments;
e) subjecting the polynucleotide extension reaction product to nicking and cleavage reactions to form double-stranded nucleic acid fragments with 3' overhangs; and
f) annealing the double-stranded nucleic acid fragments with 3' overhangs to form a nucleic acid encoding for the predetermined nucleic acid sequence that does not include the nicking endonuclease recognition site.

18. The method of claim 17, wherein x is 4, 5, or 6.

19. The method of claim 17, wherein the non-canonical base is uracil, inosine, 5-fluorouracil, 5-bromouracil, 5-chlorouracil, 5-iodouracil, hypoxanthine, xanthine, acetylcytosine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N-6-isopentenyl adenine, 1-methylguanine, 1-methylinosine, 2,2-dimethylguanine, 1-methyladenine, 2-methyladenine, 2-methylguanine, 3-methylcytosine, 5-methylcytosine, 5-ethylcytosine, N6-adenine, N6-methyladenine, N,N-dimethyladenine, 8-bromoadenine, 7-methylguanine, 8-bromoguanine, 8-chloroguanine, 8-aminoguanine, 8-methylguanine, 8-thioguanine, 5-ethyluracil, 5-propyluracil, 5-methylaminomethyluracil, methoxyarninomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, 1-methylpseudouracil, queosine, 2-thiocytosine, 5-methyl-2-thiouracil, 2-thiouracil, 4-thiouracil, 5-hydroxymethyluracil, 5-methyluracil, uracil-5-oxyacetic acid methylester, uracil-S-oxyacetic acid, 5-methyl-2-thiouracil, 3-(3-amino-3-N-2-carboxypropyl) uracil, 5-(2-bromovinyl)uracil, 2-aminopurine, 6-hydroxyaminopurine, 6-thiopurine, or 2,6-diaminopurine.

20. The method of claim 17, wherein the non-canonical base is uracil.

21. The method of claim 17, wherein one of the plurality of precursor double-stranded nucleic acid fragments comprises a portion of linear vector.

22. The method of claim 17, wherein no more than two nucleotides from the Nx portion of the sticky end sequence have the same identity.

23. The method of claim 17, wherein the plurality of precursor double-stranded nucleic acid fragments comprise an adaptor sequence comprising the nicking endonuclease recognition site.

24. The method of claim 17, wherein the predetermined nucleic acid sequence is 1 kb to 100 kb in length.

25. The method of claim 17, wherein the sticky end sequences are each at least 4 bases long in each precursor nucleic acid.

* * * * *